(12) United States Patent
Bingaman et al.

(10) Patent No.: US 9,814,702 B2
(45) Date of Patent: Nov. 14, 2017

(54) OCULAR FORMULATIONS FOR DRUG-DELIVERY AND PROTECTION OF THE ANTERIOR SEGMENT OF THE EYE

(71) Applicant: PanOptica, Inc., Bernardsville, NJ (US)

(72) Inventors: David P. Bingaman, Weatherford, TX (US); Paul G. Chaney, Mount Arlington, NJ (US); Martin B. Wax, Far Hills, NJ (US)

(73) Assignee: PanOptica, Inc., Bernardsville, NJ (US)

( * ) Notice: Subject to any disclaimer, the term of this patent is extended or adjusted under 35 U.S.C. 154(b) by 0 days.

(21) Appl. No.: 14/857,758

(22) Filed: Sep. 17, 2015

(65) Prior Publication Data

US 2016/0074371 A1 Mar. 17, 2016

Related U.S. Application Data

(60) Provisional application No. 62/051,794, filed on Sep. 17, 2014.

(51) Int. Cl.
| | |
|---|---|
| A61K 31/122 | (2006.01) |
| A61K 31/427 | (2006.01) |
| A61K 31/425 | (2006.01) |
| A61K 9/00 | (2006.01) |
| A61K 31/00 | (2006.01) |
| A61K 9/08 | (2006.01) |
| A61K 31/455 | (2006.01) |
| A61K 47/26 | (2006.01) |
| A61K 47/32 | (2006.01) |
| A61K 9/10 | (2006.01) |
| A61K 47/38 | (2006.01) |

(52) U.S. Cl.
CPC .......... *A61K 31/425* (2013.01); *A61K 9/0048* (2013.01); *A61K 9/08* (2013.01); *A61K 9/10* (2013.01); *A61K 31/00* (2013.01); *A61K 31/122* (2013.01); *A61K 31/427* (2013.01); *A61K 31/455* (2013.01); *A61K 47/26* (2013.01); *A61K 47/32* (2013.01); *A61K 47/38* (2013.01)

(58) Field of Classification Search
CPC ... A61K 31/425; A61K 31/427; A61K 31/455
See application file for complete search history.

(56) References Cited

U.S. PATENT DOCUMENTS

| | | | |
|---|---|---|---|
| 6,235,764 B1 | 5/2001 | Larson et al. | |
| 2005/0074497 A1 | 4/2005 | Schultz et al. | |
| 2011/0039900 A1 | 2/2011 | Viswanath et al. | |
| 2012/0277180 A1* | 11/2012 | Marini | A61K 9/2004 |
| | | | 514/52 |
| 2014/0303219 A1 | 10/2014 | Bingaman et al. | |

FOREIGN PATENT DOCUMENTS

| | | |
|---|---|---|
| WO | WO 2012/012404 A1 | 1/2012 |
| WO | WO 2013/126799 A1 | 8/2013 |

OTHER PUBLICATIONS

Fleisher, D. et al.; "Improved oral drug delivery: solubility limitations overcome by the use of prodrugs", Advanced Drug Delivery Reviews, vol. 19, (1996), pp. 115-130.
Stella V. et al., "Cyclodextrins", Toxicologic Pathology, vol. 36, (2008), pp. 30-42.
Robinson R. et al., "Discovery of the Hemifumarate and ($\alpha$-L-Alanyloxy)methyl Ether as Prodrugs of an Antirheumatic Oxindole: Prodrugs for the Enolic OH Group", J. Med. Chem., vol. 39, (1996), pp. 10-18.
U.S. Appl. No. 14/775,357, dated Sep. 11, 2015, Bingaman et al.

* cited by examiner

*Primary Examiner* — Zohreh Fay
(74) *Attorney, Agent, or Firm* — Cooley LLP; Heidi A. Erlacher; Chen Chen

(57) ABSTRACT

The present application relates to topical formulations comprising Compound-I

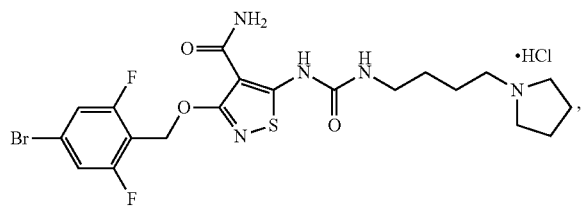

or its free base, and a second active agent selected from nicotinic acid, nicotinamide, and vitamin K, and a combination thereof, for treating ocular neovascularization. The present application also relates to pharmaceutical compositions comprising particles of Compound-I or its free base, and suspension formulations comprising the particle compositions of Compound-I or its free base.

18 Claims, 14 Drawing Sheets

Figure 6A
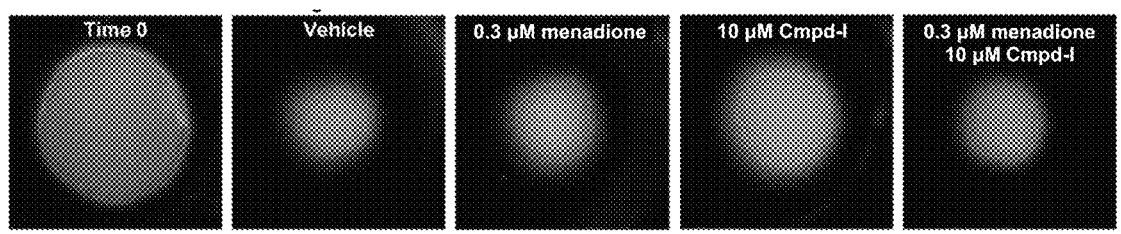
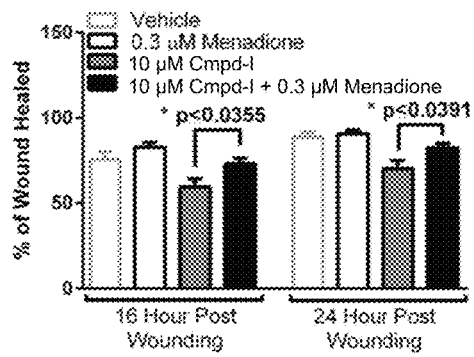
Figure 6B
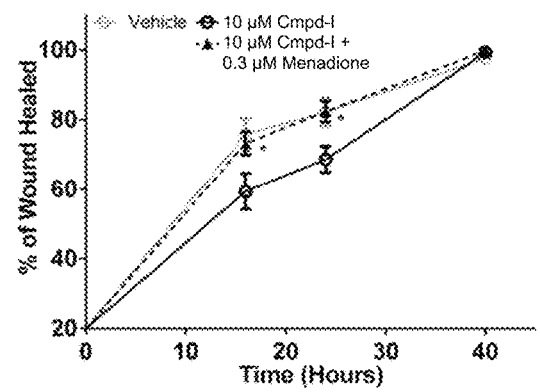
Figure 6C

OCULAR FORMULATIONS FOR DRUG-DELIVERY AND PROTECTION OF THE ANTERIOR SEGMENT OF THE EYE

RELATED APPLICATION

This application claims priority to, and the benefit of, U.S. Ser. No. 62/051,794, filed on Sep. 17, 2014, the contents of which are incorporated by reference in their entirety.

FIELD OF THE APPLICATION

Embodiments disclosed herein are generally directed to topical administration of a combination of a first active agent, e.g., a pharmaceutical compound or a salt thereof, and a second active agent, to treat ocular diseases or conditions. The embodiments disclosed include ocular formulations comprising a first active agent or a salt thereof and a second active agent, where the formulation is a solution or a suspension. The solution or suspension may further comprise a solubilizing agent, and is suitable for delivering the first active agent or a salt thereof, to the posterior segment of the eye while protecting the anterior segment of the eye of a subject.

BACKGROUND

Treatment of diseases or disorders of the posterior segment of the eye with topically applied active agents has not been effective because of inefficient delivery of the active agent to the target site. The vast majority of topical drugs penetrate via the cornea. However, the cornea is not equally permeable to all topically applied active agents, since the basic structure of the cornea dictates the relative penetration of active agent. Effectively, the greatest barrier to active agent penetration is the corneal epithelium which is rich in cellular membranes and is therefore more susceptible to penetration by lipophilic agents. In contrast, since the corneal stroma is largely constituted of water, active agents pass through more readily if they are hydrophilic. The endothelium represents a monolayer that, once more, is lipophilic. Active agents which are lipophilic or amphiphilic, in that they can behave as either charged or non-charged, penetrate the cornea best. Similar to the cornea, the conjunctival epithelium and blood vessels within or under the conjunctival epithelium may be penetrated by the same type of lipophilic or biphasic agents. However, because of the nature of the lipophilic membranes in the conjunctive and its inherent vasculature, most active agents typically do not penetrate through the conjunctiva and into the eye. Agents with limited penetration into the vascular tissues in the conjunctival and subconjunctival regions are drained into the systemic circulation.

Because of the limited permeability of many topical drops to the corneal and conjunctival barriers, one major disadvantage of topical drops may be the need for high concentration of active agents in the topical formulation in order to achieve meaningful therapeutic drug levels in internal ocular tissues. Depending on the active agent, the molecule itself or high concentrations thereof, a topical formulation may be toxic to the anterior segment of the eye, including the conjunctiva, cornea and/or lens, causing various injuries to the ocular surface, such as corneal epithelial defects and erosions.

Ocular side-effects observed following treatment with anti-EGFR drug therapies, e.g., anti-EGFR cancer therapies, have illuminated the essential role the EGFR signaling pathway plays in maintaining and restoring the health of the human corneal epithelium. Patients treated with anti-EGFR drug therapies can develop corneal changes, such as epithelial degeneration and defects, ulceration, corneal epithelial thinning, erosions and/or corneal edema, keratitis as well as perforation while undergoing therapy or even after discontinuation of the anti-EGFR therapy. The important role of EGFR signaling in homeostasis and pathophysiology of the corneal epithelium is well established. EGFR activation is both necessary and sufficient for corneal epithelial migration, proliferation, and differentiation. Moreover, EGFR is the primary mediator of wound healing during in vitro experiments with immortalized human corneal epithelial cells. Therefore, treating ocular diseases or disorders (e.g., diseases or disorders of the posterior segment of the eye) would benefit from administration of an agent that maintains EGFR activity in addition to the administration of a formulation comprising an active agent (e.g., an active agent having toxic or anti-EGFR activity).

The present application provides novel formulations which circumvent the problems encountered in ocular delivery of existing topical therapeutic agents. The present application accomplishes the combined effects of decreasing corneal and anterior segment drug exposure and protecting corneal and anterior segment tissues, while increasing posterior segment bioavailability. By lowering corneal exposure, protecting corneal tissues, and increasing posterior segment bioavailability, the formulation of the present application improves ocular tolerability and increases the therapeutic index of the active agent.

SUMMARY

The present application relates to pharmaceutical formulations in the form of a solution and/or a suspension, which lower the exposure to a first active agent in the anterior segment of the eye, for example the ocular surface comprised of the cornea and conjunctiva, and protect the eye, for example, the anterior segment of the eye, through maintenance of EGFR activity. The pharmaceutical formulations of the application increase the bioavailability of the first active agent at the posterior segment of the eye, for example at the central choroid and/or the central retina, and protect and/or improve the health of the anterior segment of the eye.

The present application provides a formulation comprising a first active agent, and optionally a second active agent, in the form of a solution or a suspension, with superior characteristics compared to a composition formed as a gel. The present application provides that the first active agent and/or the second active agent can be formulated together as a solution and/or a suspension. Increased levels of the first active agent in the anterior segment of the eye limit ocular tolerability of topical drops containing the first active agent and may cause corneal epithelial defects and erosions. The presence of the second active agent can prevent damage that may be caused by exposure to the first active agent, treat any damage that may be caused by exposure to the first active agent, and/or improve the overall health of the ocular surface, specifically the corneal epithelium. The second active agent can be formulated together with the first active agent, or formulated as a separate formulation that is administered in combination with the formulation comprising the first active agent.

The formulations of the present application reduce exposure of the first active agent at the anterior segment of the eye, such as corneal or conjunctival surface, protect from and/or repair damages to the anterior segment of the eye, such as the corneal or conjunctival surface, and maintain adequate concentrations of a first active agent necessary to bind the relevant receptors at the target tissues and confer a therapeutic effect in the posterior segment of the eye, such as the choroid and the retina.

The present application relates to formulations and methods useful for treating pathological states that arise from or are exacerbated by ocular angiogenesis, neovascularization, and/or vascular leakage, for example, in diabetic retinopathy (including background diabetic retinopathy, proliferative diabetic retinopathy, and diabetic macular edema); age-related macular degeneration (AMD) (including neovascular (wet/exudative) AMD, dry AMD, and Geographic Atrophy); pathologic choroidal neovascularization (CNV) and vascular leakage from any mechanism (e.g., high myopia, trauma, sickle cell disease; ocular histoplasmosis, angioid streaks, traumatic choroidal rupture, drusen of the optic nerve, or some retinal dystrophies); pathologic retinal neovascularization and vascular leakage from any mechanism (e.g., sickle cell retinopathy, Eales disease, ocular ischemic syndrome, carotid cavernous fistula, familial exudative vitreoretinopathy, hyperviscosity syndrome, idiopathic occlusive arteriolitis, birdshot retinochoroidopathy, retinal vasculitis, sarcoidosis, or toxoplasmosis); uveitis; retinal vein occlusion (central or branch); ocular trauma; surgery induced edema; surgery induced neovascularization; cystoid macular edema; ocular ischemia; retinopathy of prematurity; Coat's disease; sickle cell retinopathy; and/or neovascular glaucoma. In one embodiment, the pathological state is AMD. In one embodiment, the pathological states arise from or are exacerbated by ocular angiogenesis and/or neovascularization.

The present application also relates to formulations and methods useful for preventing and/or treating corneal epithelium disruptions associated with a disease, including a systemic disease (e.g., cancer, diabetes, etc.) and an eye disease, or with a side effect from a locally or systemically administered drug (e.g., anti-EGFR agents or EGFR inhibitors). The formulation of the present application has, at least, one anti-angiogenic agent, anti-inflammatory agent, or anti-vascular permeability agent for use in treating angiogenic ocular disorders and an EGFR modulator (e.g., an agent that maintains the activity of or activates EGFR) for use in preventing and/or treating corneal epithelium disruptions.

According to embodiments of the application, the first active agent is an anti-angiogenic kinase inhibitor and the second active agent is a kinase modulator (e.g., activator). In one embodiment, the first active agent inhibits a kinase that is different from the kinase that is modulated (e.g., activity maintained or activated) by the second active agent. Examples of some kinase inhibitors that can be used to bring about beneficial therapeutic results include inhibitors of receptor tyrosine kinases, for example, without being limiting, VEGFR, FGFR, Tie-2, and Ephrin kinase receptors. Examples of kinase modulators that can be used to bring about beneficial therapeutic results include activators of ErbB receptor tyrosine kinase, for example, without being limiting, EGFR1/ErbB1/HER1, ErbB2/HER2/Neu, ErbB3/HER3, and ErbB4/HER. In one embodiment, the ErbB receptor tyrosine kinase is EGFR1. In one embodiment, the first active agent is a VEGFR inhibitor. In one embodiment, the second active agent is an EGFR modulator (e.g., activator). In a further embodiment, the second active agent is nicotinic acid, nicotinamide, or vitamin K, or a combination thereof. In a further embodiment, the second active agent is nicotinic acid or nicotinamide. In another embodiment, the second active agent vitamin K.

In some embodiments, a second active agent of the present application reduces or alleviates the inhibition of EGFR at the anterior segment of the eye caused by high concentrations of a first active agent of the present application (e.g., transient high concentrations of the first active agent after administration of the first active agent to the anterior segment of the eye).

The embodiments of the present application provide an ophthalmic formulation for treating ocular neovascularization comprising a first active agent of Formula I:

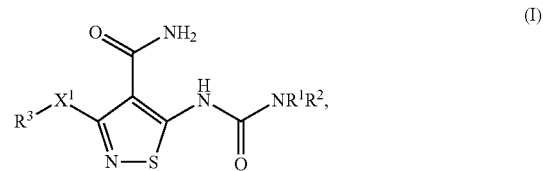

(I)

or a pharmaceutically acceptable salt thereof; a second active agent wherein the second active agent is an EGFR modulator (e.g., activator), such as nicotinic acid, nicotinamide, or vitamin K, or a combination thereof; and pharmaceutically acceptable excipients; the first active agent or the pharmaceutically acceptable salt is present in about 0.02% to about 1.2% w/v such that the formulation forms a solution or suspension, and wherein:

$X^1$ is O or S;

$R^1$ is H, $C_1$-$C_{10}$ alkyl, $C_2$-$C_{10}$ alkenyl, $C_2$-$C_{10}$ alkynyl, $C(O)(C_1$-$C_{10}$ alkyl), $(CH_2)_t(C_6$-$C_{10}$ aryl), $(CH_2)_t$ (4-10 membered heterocyclic), $C(O)(CH_2)_t(C_6$-$C_{10}$ aryl), or $C(O)(CH_2)_t$ (5-10 membered heterocyclic), wherein:

t is an integer from 0 to 5;

the alkyl group optionally includes 1 or 2 hetero moieties selected from O, S and $N(R^6)$ with the proviso that two O atoms, two S atoms, or an O and an S atoms are not attached directly to each other;

the aryl and heterocyclic groups are optionally fused with a $C_6$-$C_{10}$ aryl group, a $C_5$-$C_8$ saturated cyclic group, or a 5-10 membered heterocyclic group;

1 or 2 carbon atoms in the foregoing heterocyclic moieties are optionally substituted with an oxo (=O) moiety or an anion of oxygen;

the $(CH_2)_t$ moieties optionally include a carbon-carbon double or triple bond when t is an integer from 2 to 5; and the foregoing $R^1$ groups, except H, are optionally substituted with 1 to 3 $R^4$ groups;

$R^2$ is H;

$R^3$ is $(CH_2)_t(C_6$-$C_{10}$ aryl), wherein:

t is an integer from 0 to 5;

the aryl group is optionally fused with a $C_6$-$C_{10}$ aryl group, a $C_5$-$C_8$ saturated cyclic group, or a 5-10 membered heterocyclic group;

the $(CH_2)_t$ moieties optionally include a carbon-carbon double or triple bond when t is an integer from 2 to 5; and the foregoing $R^3$ groups are optionally substituted with 1 to 5 $R^4$ groups;

each $R^4$ is independently selected from $C_1$-$C_{10}$ alkyl, $C_2$-$C_{10}$ alkenyl, $C_2$-$C_{10}$ alkynyl, halo, cyano, nitro, trifluoromethyl, trifluoromethoxy, azido, $OR^5$, $C(O)R^5$, $C(O)OR^5$, $NR^6C(O)R^5$, $NR^6C(O)OR^5$, $OC(O)R^5$, $NR^6SO_2R^5$, $SO_2NR^5R^6$, $C(O)NR^5R^6$, $NR^5R^6$, $S(O)_jR^7$ where j is an integer from 0 to 2, $SO_3H$, $NR^5(CR^6R^7)_tOR^6$, $(CH_2)_t(C_6$-$C_{10}$ aryl), $SO_2(CH_2)_t(C_6$-$C_{10}$ aryl), $S(CH_2)_t(C_6$-$C_{10}$ aryl), O(CH$_2$)$_t$(C$_6$-C$_{10}$ aryl), (CH$_2$)$_t$ (5-10 membered heterocyclic), and (CR$^6$R$^7$)$_m$OR$^6$, wherein:

m is an integer from 1 to 5;

t is an integer from 0 to 5;

the alkyl group optionally includes 1 or 2 hetero moieties selected from O, S and N(R$^6$) with the proviso that two O atoms, two S atoms, or an O and an S atoms are not attached directly to each other;

the aryl and heterocyclic groups are optionally fused with a C$_6$-C$_{10}$ aryl group, a C$_5$-C$_8$ saturated cyclic group, or a 5-10 membered heterocyclic group;

1 or 2 carbon atoms in the foregoing heterocyclic moieties are optionally substituted with an oxo (=O) moiety or an anion of oxygen; and the alkyl, aryl and heterocyclic moieties of the foregoing R$^4$ groups are optionally substituted with 1 to 3 substituents independently selected from halo, cyano, nitro, trifluoromethyl, trifluoromethoxy, azido, NR$^6$SO$_2$R$^5$, SO$_2$NR$^5$R$^6$, C(O)R$^5$, C(O)OR$^5$, OC(O)R$^5$, NR$^6$C(O)R$^5$, C(O)NR$^5$R$^6$, NR$^5$R$^6$, (CR$^6$R$^7$)$_m$OR$^6$ where m is an integer from 1 to 5, OR$^5$, and the substituents listed in the definition of R$^5$; and R$^5$, R$^6$, and R$^7$ are each independently H or C$_1$-C$_6$ alkyl.

In one embodiment, R$^3$ is (CH$_2$)$_t$(C$_6$-C$_{10}$ aryl), wherein t is an integer from 1 to 3 and R$^3$ is optionally substituted with 1 to 4 R$^4$ groups.

In a further embodiment, R$^3$ is benzyl, optionally substituted with 1 to 4 substituents independently selected from halo and C$_1$-C$_4$ alkyl. In a further embodiment, R$^3$ is benzyl substituted with 1 to 4 substituents independently selected from methyl, fluoro, chloro and bromo.

In one embodiment, R$^1$ is (CH$_2$)$_t$ (5-10 membered heterocyclic), wherein t is an integer from 0 to 5, optionally substituted with 1 or 2 substituents independently selected from C$_1$-C$_4$ alkyl, hydroxy and hydroxymethyl.

The present application provides heterocyclic moiety of the R$^1$ group in Formula I selected from morpholino, pyrrolidinyl, imidazolyl, piperazinyl, piperidinyl, and 2,5-diaza-bicyclo[2.2.1]hept-2-yl, the t variable of the R$^1$ group ranges from 2 to 5, and the R$^1$ group is optionally substituted with one or more hydroxy groups.

For example, the heterocyclic moiety of the R$^1$ group in Formula I of the present application is pyrrolidine.

In a further embodiment of the present application, the first active agent is:

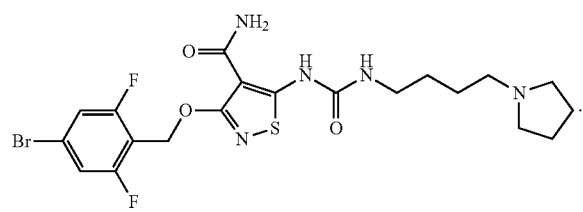

(II)

In a further embodiment of the present application, the first active agent is a hydrochloride salt of compound of Formula II, namely Compound-I:

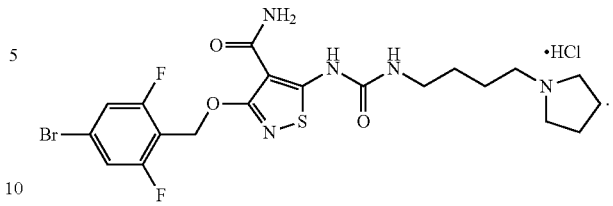

(Compound-I)

In one embodiment, the second active agent is an EGFR modulator (e.g., activator). In a further embodiment, the second active agent is nicotinic acid, nicotinamide, or vitamin K, or a combination thereof. In a further embodiment, the second active agent is vitamin K.

The embodiments of the present application provide formulations comprising about 0.005% to about 5.0% w/v of the first active agent of Formula I or II, or a pharmaceutically acceptable salt thereof, for example, Compound-I. In some embodiments, the concentration of Compound-I or its free base (Formula II) in the formulations is about 0.005%-about 0.01%, about 0.01%-about 0.05%, about 0.05%-about 0.1%, about 0.1%-about 0.2%, about 0.2%-about 0.3%, about 0.3%-about 0.4%, about 0.4%-about 0.5%, about 0.5%-about 0.6%, about 0.6%-about 0.7%, about 0.7%-about 0.8%, about 0.8%-about 0.9%, about 0.9%-about 1.0%, about 1.1-about 2.0%, about 2.1-about 3.0%, about 3.1-about 4.0%, or about 4.1-about 5.0% w/v for topical administration. In some embodiments, the concentration of Compound-I or its free base (Formula II) in the formulations is about 0.1%-about 1.2%, about 0.2%-about 1.2%, about 0.3%-about 1.2%, about 0.4%-about 1.2%, 0.1%-about 1.1%, about 0.2%-about 1.1%, about 0.3%-about 1.1%, about 0.4%-about 1.1%, 0.1%-about 1.0%, about 0.2%-about 1.0%, about 0.3%-about 1.0%, about 0.4%-about 1.0%, 0.1%-about 0.8%, about 0.2%-about 0.8%, about 0.3%-about 0.8%, about 0.4%-about 0.8%, 0.1%-about 0.6%, about 0.2%-about 0.6%, about 0.3%-about 0.6%, about 0.4%-about 0.6%, 0.1%-about 0.5%, about 0.2%-about 0.5%, about 0.3%-about 0.5%, about 0.4%-about 0.5%, 0.1%-about 0.4%, about 0.2%-about 0.4%, about 0.3%-about 0.4% w/v for topical administration. In some embodiments the formulations include about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of Compound-I or its free base (Formula II).

In some embodiments, the present application provides a solution of a first active agent (e.g., Compound-I) and a second active agent (e.g., nicotinic acid, nicotinamide, or vitamin K, or a combination thereof), which includes one or more solubilizing agents.

In some embodiments, the formulation comprises about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of Formula I or II, or a pharmaceutically acceptable salt thereof, for example, Compound-I, and a second active agent and a solubilizing agent.

In some embodiments, the solubilizing agent in the formulation may be cyclodextrin, for example, 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-

(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or a combination thereof.

In one embodiment, the solubilizing agent in the formulation is 2-hydroxypropyl-β-cyclodextrin or β-cyclodextrin sulfobutyl ether.

In one embodiment, the formulation may further comprise one or more of benzalkonium chloride (BAK), sodium chloride, and a pH adjusting agent.

In additional embodiments, the formulation comprises about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of a first active agent or a pharmaceutically acceptable salt thereof, and a buffer, for example, tromethamine. In one embodiment, the formulation comprises about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of the first active agent or a pharmaceutically acceptable salt thereof, and about 0.3%-about 1.0% w/v tromethamine, and optionally further comprises about 0.005% w/v benzalkonium chloride (BAK).

In some embodiments, the second active agent is an EGFR modulator (e.g., activator). For example, the second active agent includes, but is not limited to, nicotinic acid (or niacin/vitamin B3), nicotinamide, and vitamin K, or a combination thereof. "Vitamin K," as defined herein, includes one or more members of the vitamin K family and prodrugs thereof, naturally occurring or synthetic. The vitamin K family is comprised of vitamin $K_1$ (also known as phylloquinone, phytomenadione or phytonadione), vitamin $K_2$, and any vitamin $K_2$ homologues. The vitamin $K_2$ homologues are called menoquinones and are characterized by the number of isoprenoid residues in their sidechains. Synthetic vitamin K includes, but is not limited to vitamin $K_3$ (i.e., menadione), vitamin $K_4$, vitamin $K_5$. In one embodiment, the second active agent is nicotinic acid and/or and nicotinamide. In another embodiment, the second active agent is nicotinic acid. In another embodiment, the second active agent is nicotinamide. In yet another embodiment, the second active agent is vitamin K. In another embodiment, the second active agent is vitamin $K_1$. In yet another embodiment, the second active agent is vitamin $K_2$. In yet another embodiment, the second active agent is a vitamin $K_2$ homologue. In yet another embodiment, the second active agent is a synthetic vitamin K (e.g., vitamin $K_3$, vitamin $K_4$, or vitamin $K_5$). In one embodiment, the second active agent is vitamin $K_3$ (i.e., menadione).

In some embodiments, the concentration of the second active agent in the formulations is about 0.00001%-about 5.0% w/v for topical administration. In some embodiments, the concentration of the second active agent in the formulations is about 0.00001%-about 1.0%, about 0.00001%-about 0.1%, about 0.00001%-about 0.01%, about 0.00001%-about 0.001%, about 0.00001%-about 0.0002%, or about 0.00001%-about 0.0001% w/v for topical administration. In some embodiments, the concentration of the second active agent in the formulations is about 0.00001%-about 0.0001%, 0.000012%-about 0.0001%, 0.000014%-about 0.0001%, 0.000016%-about 0.0001%, 0.000018%-about 0.0001%, 0.00002%-about 0.0001%, 0.00003%-about 0.0001%, 0.00004%-about 0.0001%, 0.00005%-about 0.0001%, 0.00006%-about 0.0001%, 0.00007%-about 0.0001%, 0.00008%-about 0.0001%, 0.00009%-about 0.0001%, 0.000016%-about 0.00009%, 0.000018%-about 0.00009%, 0.00002%-about 0.00009%, 0.00003%-about 0.00009%, 0.00004%-about 0.00009%, 0.00005%-about 0.00009%, 0.00006%-about 0.00009%, 0.00007%-about 0.00009%, or 0.00008%-about 0.00009% w/v for topical administration. In some embodiments, the formulations include about 0.00001%, 0.00002%, 0.00003%, 0.00004%, 0.00005%, 0.00006%, 0.00007%, 0.00008%, 0.000081%, 0.000082%, 0.000083%, 0.000084%, 0.000085%, 0.000086%, 0.000087%, 0.000088%, or 0.000089% w/v of the second active agent, or a pharmaceutically acceptable salt thereof.

In some embodiments, the concentration of the second active agent in the formulations is about 0.5 µM, about 0.6 µM, about 0.7 µM, about 0.8 µM, about 0.9 µM, about 1 µM, about 2 µM, about 3 µM, about 4 µM, about 5 µM, about 6 µM, about 7 µM, about 8 µM, or about 9 µM. In some embodiments, the concentration of the second active agent is about 1 µM.

The present application provides a formulation having a pH value of about 4.5 to about 7.5 at or under about 40° C. In some embodiments, the pH value of the formulation is between about pH 5.0 to about 7.0. In one embodiment, the pH value of the formulation is about 6.0 at or under about 40° C.

In another embodiment, the present application provides use of a formulation comprising a first active agent (e.g., Formula I or Compound-I or its free base (Formula II)), and a second active agent (e.g., nicotinic acid, nicotinamide, or vitamin K, or a combination thereof), for the manufacture of a medicament for accessing posterior segment of the eye and/or for treating and/or ameliorating a posterior segment disease or a vasculopathic or inflammatory disease of the eye, as described herein, e.g., diabetic retinopathy (including background diabetic retinopathy, proliferative diabetic retinopathy and diabetic macular edema); age-related macular degeneration (AMD) (including neovascular (wet/exudative) AMD, dry AMD, and Geographic Atrophy); pathologic choroidal neovascularization (CNV) from any mechanism (e.g., high myopia, trauma, sickle cell disease; ocular histoplasmosis, angioid streaks, traumatic choroidal rupture, drusen of the optic nerve, and some retinal dystrophies); pathologic retinal neovascularization from any mechanism (e.g., sickle cell retinopathy, Eales disease, ocular ischemic syndrome, carotid cavernous fistula, familial exudative vitreoretinopathy, hyperviscosity syndrome, idiopathic occlusive arteriolitis; birdshot retinochoroidopathy, retinal vasculitis, sarcoidosis and toxoplasmosis); uveitis; retinal vein occlusion (central or branch); ocular trauma; surgery induced edema; surgery induced neovascularization; cystoid macular edema; ocular ischemia; retinopathy of prematurity; Coat's disease; sickle cell retinopathy and/or neovascular glaucoma. In one embodiment, the disease of the eye is AMD. In one embodiment, the diseases of the eye arise from or are exacerbated by ocular angiogenesis and/or neovascularization.

In another embodiment, the present application relates to a formulation for use in the manufacture of a medicament suitable for accessing the posterior segment of the eye and/or for treating and/or ameliorating a posterior segment disease or a vasculopathic or inflammatory disease of the eye. In one embodiment, the formulation comprises a first active agent and a second active agent. In one embodiment, the first active agent is a VEGFR inhibitor. In one embodiment, the first active agent is a compound of Formula I or a pharmaceutically acceptable salt thereof. In a further embodiment, the first active agent is a compound of Formula II or a pharmaceutically acceptable salt thereof. In a further embodiment, the first active agent is Compound-I. In one embodiment, the second active agent is an EGFR modulator (e.g., activator). In a further embodiment, the second active agent is selected from nicotinic acid, nicotinamide, and vitamin K, and a combination thereof. The formulation may further comprise one or more pharmaceutically acceptable excipients.

In another embodiment, the present application relates to a formulation for use in the manufacture of a medicament for treating and/or ameliorating a symptom of an ocular disease or disorder (e.g., a posterior segment or vasculopathic or inflammatory disease of the eye). In one embodiment, the formulation comprises a first active agent and a second active agent. In one embodiment, the first active agent is a VEGFR inhibitor. In one embodiment, the first active agent is a compound of Formula I or a pharmaceutically acceptable salt thereof. In a further embodiment, the first active agent is a compound of Formula II or a pharmaceutically acceptable salt thereof. In a further embodiment, the first active agent is Compound-I. In one embodiment, the second active agent is an EGFR modulator (e.g., activator). In a further embodiment, the second active agent is selected from nicotinic acid, nicotinamide, and vitamin K, and a combination thereof. The formulation may further comprise one or more pharmaceutically acceptable excipients.

In yet another embodiment, the present application relates to a formulation for use in a method for accessing posterior segment of the eye and/or for treating and/or ameliorating a posterior segment disease of the eye. In one embodiment, the formulation comprises a first active agent and a second active agent. In one embodiment, the first active agent is a VEGFR inhibitor. In one embodiment, the first active agent is a compound of Formula I or a pharmaceutically acceptable salt thereof. In a further embodiment, the first active agent is a compound of Formula II or a pharmaceutically acceptable salt thereof. In a further embodiment, the first active agent is Compound-I. In one embodiment, the second active agent is an EGFR modulator (e.g., activator). In one embodiment, the second active agent is selected from nicotinic acid, nicotinamide, and vitamin K, and a combination thereof. The formulation may further comprise one or more pharmaceutically acceptable excipients.

In yet another embodiment, the present application relates to a formulation for use in a method for treating and/or ameliorating a symptom of an ocular disease or disorder (e.g., a posterior segment vasculopathic or inflammatory disease of the eye). In one embodiment, the formulation comprises a first active agent and a second active agent. In one embodiment, the first active agent is a VEGFR inhibitor. In one embodiment, the first active agent is a compound of Formula I or a pharmaceutically acceptable salt thereof. In a further embodiment, the first active agent is a compound of Formula II or a pharmaceutically acceptable salt thereof. In a further embodiment, the first active agent is Compound-I. In one embodiment, the second active agent is an EGFR modulator (e.g., activator). In a further embodiment, the second active agent is selected from nicotinic acid, nicotinamide, and vitamin K, and a combination thereof. The formulation may further comprise one or more pharmaceutically acceptable excipients.

In another embodiment, the present application relates to a combinational therapy for accessing the posterior segment of the eye and/or for treating and/or ameliorating a posterior segment disease of the eye, wherein the therapy comprises administering a first active agent and a second active agent. In one embodiment, the first active agent is a VEGFR inhibitor. In one embodiment, the first active agent is a compound of Formula I or a pharmaceutically acceptable salt thereof. In a further embodiment, the first active agent is a compound of Formula II or a pharmaceutically acceptable salt thereof. In a further embodiment, the first active agent is Compound-I. In one embodiment, the second active agent is an EGFR modulator (e.g., activator). In a further embodiment, the second active agent is selected from nicotinic acid, nicotinamide, and vitamin K, and a combination thereof. In one embodiment, the first active agent is administered simultaneously with the second active agent. In another embodiment, the first active agent is administered prior to the administration of the second active agent. In another embodiment, the first active agent is administered after the administration of the second active agent.

In another embodiment, the present application relates to a combinational therapy for treating and/or ameliorating a symptom of an ocular disease or disorder (e.g., a posterior segment vasculopathic or inflammatory disease of the eye), comprising administering a first active agent and a second active agent. In one embodiment, the first active agent is a VEGFR inhibitor. In one embodiment, the first active agent is a compound of Formula I or a pharmaceutically acceptable salt thereof. In a further embodiment, the first active agent is a compound of Formula II or a pharmaceutically acceptable salt thereof. In a further embodiment, the first active agent is Compound-I. In one embodiment, the second active agent is an EGFR modulator (e.g., activator). In a further embodiment, the second active agent is selected from nicotinic acid, nicotinamide, and vitamin K, and a combination thereof. In one embodiment, the first active agent is administered simultaneously with the second active agent. In another embodiment, the first active agent is administered prior to the administration of the second active agent. In another embodiment, the first active agent is administered after the administration of the second active agent.

In some embodiments, the exposure time of the first active agent (e.g., Compound-I) and the second active agent is between 1 and 90 days or for longer than 90 days (e.g., 4 months, 6 months, 8 months, or 12 months). In some embodiments, the exposure time of the first active agent (e.g., Compound-I) and the second active agent is longer than 90 days (e.g., 4 months, 6 months, 8 months, or 12 months). In some embodiments, the dosage regimen involves several courses of topical ocular administration of a formulation comprising the first active agent (e.g., Compound-I) and a second active agent to a subject for between 1 and 90 days or for longer than 90 days (e.g., 4 months, 6 months, 8 months, or 12 months) or for longer than 90 days (e.g., 4 months, 6 months, 8 months, or 12 months) or for longer than 90 days. For example, the dosage regimen involves once daily, twice daily, three times daily or four times daily administration of the formulation for between 1 and 90 days or for longer than 90 days (e.g., 4 months, 6 months, 8 months, or 12 months) or for longer than 90 days (e.g., 4 months, 6 months, 8 months, or 12 months). For example, the dosage regimen involves once, twice, three times, or four times administration of the formulation on alternate days (i.e., on day 1, 3, 5, 7 etc.) for up to 90 days. For example, the dosage regimen involves administering once on day 1, once or twice on day 2 to day 90. For example, the dosage regimen involves administering once, twice, three times, or four times on day 1, followed by once daily for 2-90 days. For example, the dosage regimen involves administering once, twice, three times, four times on day 1, followed by once, twice, three times, or four times on alternate days (i.e., on day 1, 3, 5, 7 etc.) for up to 90 days. For example, one dosage regimen involves administering once or twice per day for 1, 2, 3, 4, or 5 consecutive days. For twice or three daily dosage regimen, subjects receive a topical ocular dose of a first active agent (e.g., Compound-I) and a second active agent formulation on days 1 and 4 approximately about 4, 6, or 8 hours apart. In another embodiment, subjects receive topical ocular doses of a first active agent (e.g., Compound-I) and a second active agent formulation approximately about 4, 6, or 8 hours apart for four consecutive days. In some embodiments, subjects receive one or two topical ocular doses of a first active agent (e.g., Compound-I) and a second active agent formulation per day for 5 consecutive days. In yet other embodiments, subjects receive one or two topical ocular dose of a first active agent (e.g., Compound-I) and a second active agent formulation for 5-90 consecutive days. In some embodiments, subjects receive one or two topical ocular doses of a first active agent (e.g., Compound-I) and a second active agent formulation for at least 25 consecutive days. In one embodiment, subjects receive one or two topical ocular doses for at least 90 consecutive days or more.

For example, a formulation comprising about 1 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months) or for longer than 90 days (e.g., 4 months, 6 months, 8 months, or 12 months). In some embodiments a formulation comprising about 1 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 1 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 1 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 2 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 2 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 2 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 2 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 3 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 3 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 3 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 3 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 4 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 4 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 4 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 4 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 5 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 5 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 5 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 5 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 6 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 6 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 6 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 6 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 7 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 7 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 7 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 7 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 8 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 8 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 8 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 8 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 9 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 9 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 9 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 9 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 10 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). The dosage regimen for between 1 and 90 days or for longer than 90 days (e.g., 4 months, 6 months, 8 months, or 12 months) may be any of the regimens involving consecutive or alternate days described in the paragraph above. In some embodiments, the formulation of the present application is administered QD or BID. In some embodiments, the formulation of the present application is administered QD, BID, TID, or QID when administered at low doses (e.g., 1 mg/mL, 2 mg/mL, 3 mg/mL, 4 mg/mL, or 5 mg/mL), and QD or BID at high doses (e.g., 6 mg/mL, 7 mg/mL, 8 mg/mL, 9 mg/mL, or 10 mg/mL).

In some embodiments, the formulation of a first active agent (e.g., Formula II or Compound-I) and a second active agent is administered to one eye or both eyes of a subject. For example, about 0.2%-about 1.0% (w/v) of the compound of Formula II or about 0.1%-1.2% (w/v) of Compound-I and a second active agent comprising formulation of the present application is administered once a day (QD), twice a day (BID), three times a day (TID), or four times a day (QID) to one eye or both eyes of a subject for between 1 and 90 days or for longer than 90 days (e.g., 4 months, 6 months, 8 months, or 12 months). In some embodiments, Formula II compound or Compound-I is complexed with a complexing agent, e.g., cyclodextrin (e.g., hydroxypropyl-β-cyclodextrin (HP-β-CD, KLEPTOSE® HPB) (%)) in ratio of about 1:8, in which about 2%-13% (w/v) cyclodextrin (e.g., KLEPTOSE® HPB (%)) is added to the formulation. The formulation may further comprise about 0.1%-about 0.2% buffer, e.g., 10 mM phosphate buffer. The desired osmolality of the formulation may be about 200-about 300 mOsm, achieved by adding quantity sufficient to achieve the osmolality with a salt, e.g., sodium chloride. The pH of the formulation may be about 6.0.

The present application relates to a pharmaceutical composition comprising particles of an active agent of the present application (e.g., a first active agent (e.g., Formula II or Compound-I) and/or a second active agent), or a pharmaceutically acceptable salt thereof, wherein the particles have a mean diameter of between 100 nm and 100 μm.

The present application relates to a suspension formulation comprising a pharmaceutical composition, wherein the pharmaceutical composition comprises particles of an active agent of the present application (e.g., a first active agent (e.g., Formula II or Compound-I) and/or a second active agent), or a pharmaceutically acceptable salt thereof, as described herein.

treated with varying concentrations of a first active agent of the present application either alone, or after treatment with vitamin $K_3$ (50 μM), nicotinic acid (10 μM), or nicotinamide (10 μM) (first row: immunoblotting of total EGFR, second row: immunoblotting showing phosphorylation of tyrosine 1068 of EGFR, third row: immunoblotting showing phosphorylation of tyrosine 1045 of EGFR).

Figure 3A:
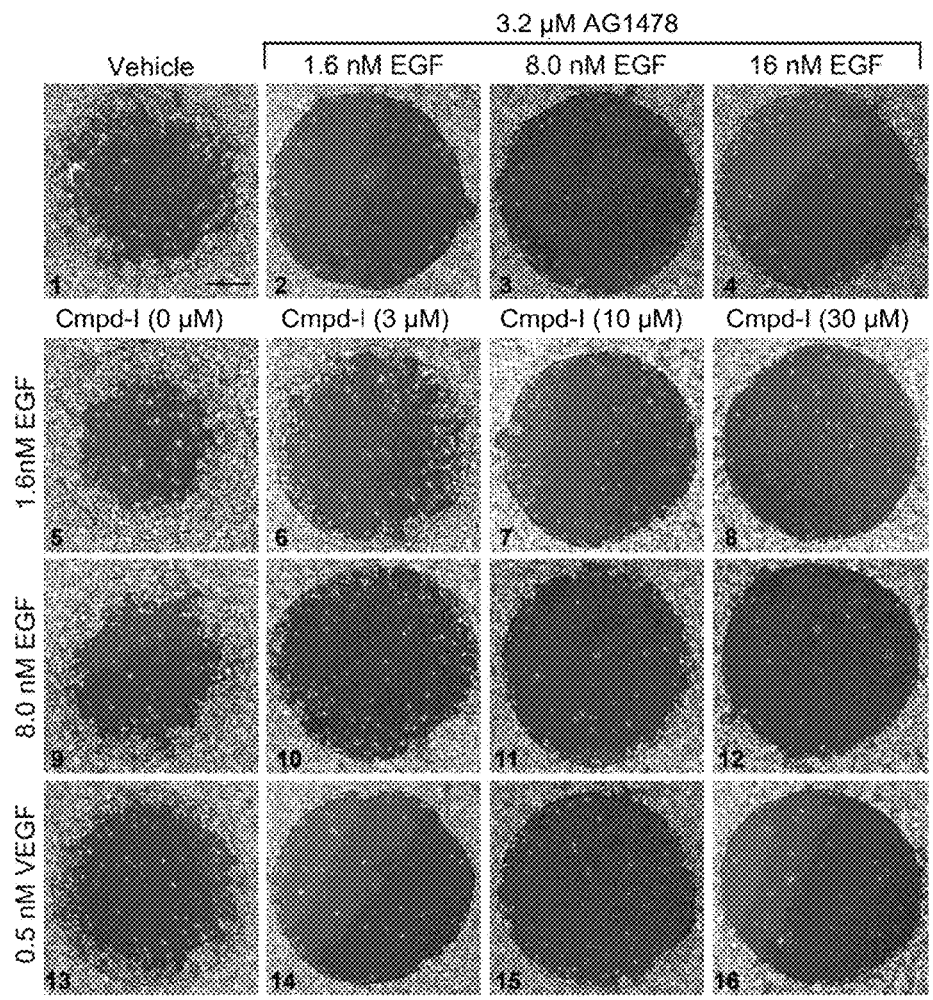
Figure 3B:
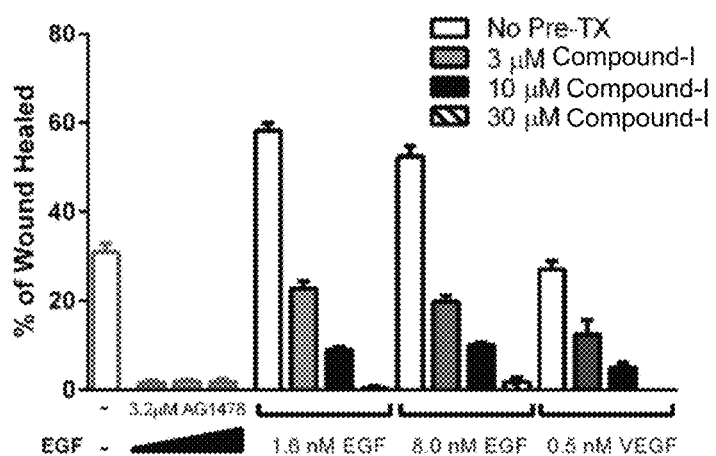

FIG. 3A is a series of micrographs showing the migration/proliferation of immortalized corneal epithelial cells (hTCEpi cells) treated for 30 minutes with the indicated concentrations of a first active agent of the present application or a control (AG1478, an EGFR kinase inhibitor), followed by 16 hour treatment with the first active agent or control together with the indicated concentrations of EGF or VEGF. FIG. 3B is a series of bar graphs quantifying the migration/proliferation of hTCEpi cells in FIG. 3A.

Figure 4A:
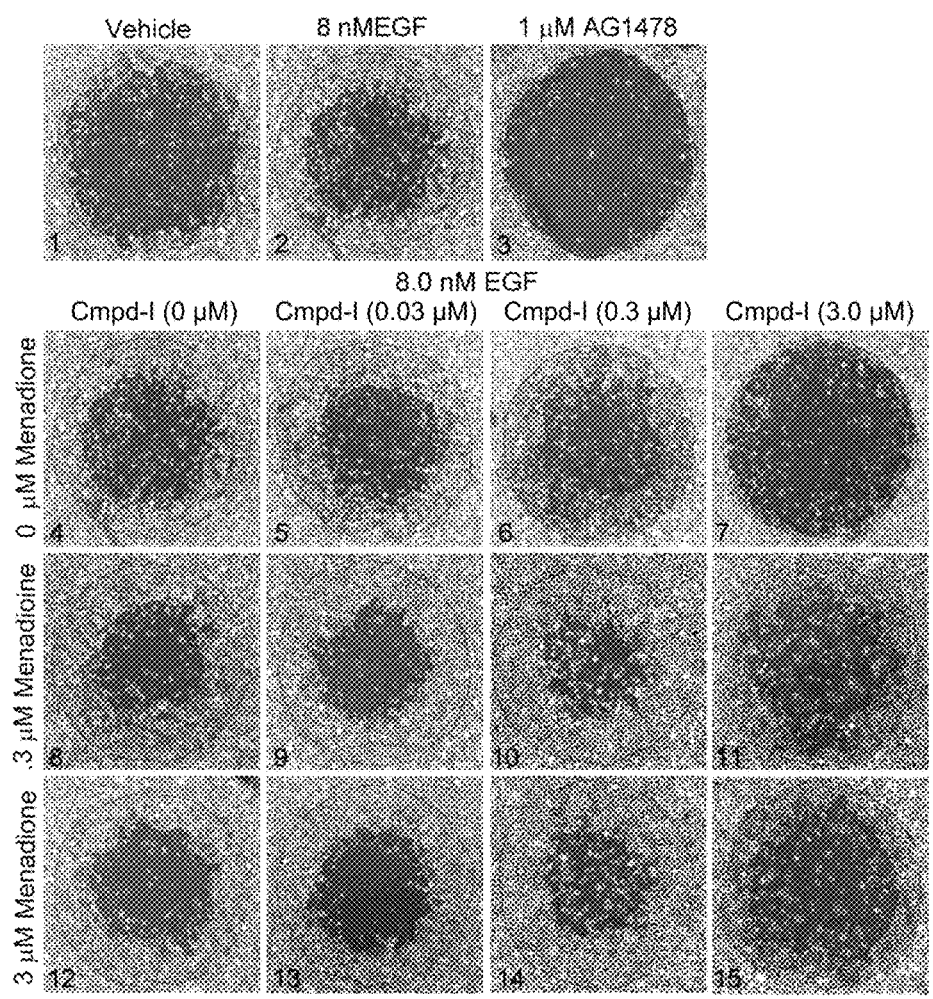
Figure 4B:
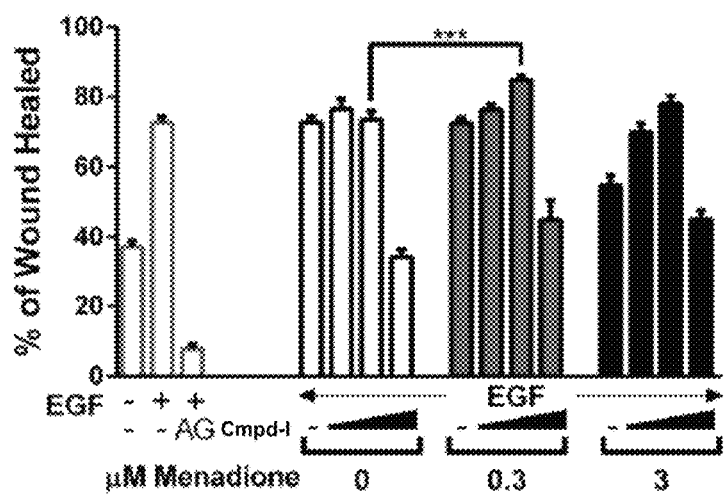

FIG. 4A is a series of micrographs showing the migration/proliferation of immortalized corneal epithelial cells (hTCEpi cells) treated with the indicated concentrations of vitamin $K_3$, menadione, for 4 hours, and then supplemented with varying concentrations of a first active agent of the present application, followed by treatment with vitamin $K_3$, the first active agent together with the EGF. FIG. 4B is a series of bar graphs quantifying the migration/proliferation of hTCEpi cells in FIG. 4A.

Figure 5A:
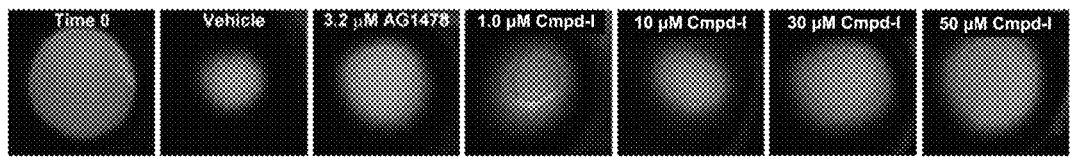
Figure 5B:
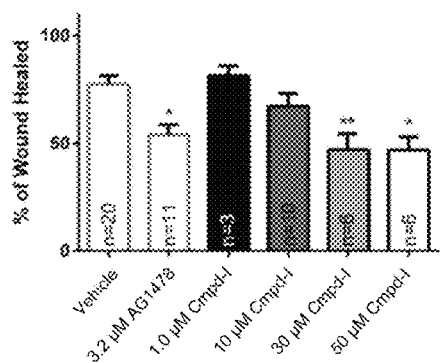
Figure 5C:
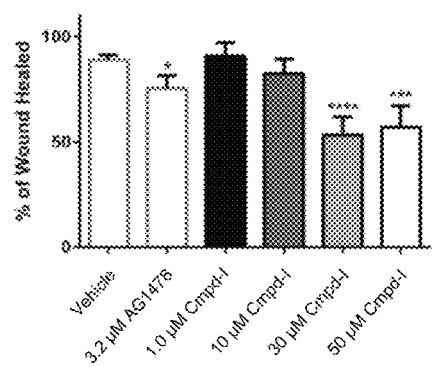
Figure 5D:
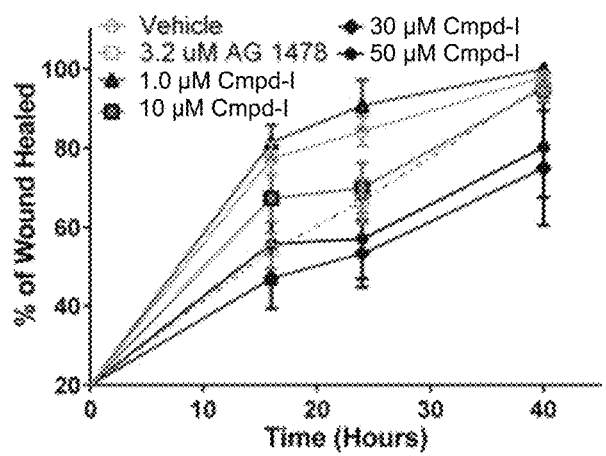

FIG. 5A is a series of images of epithelial wounds at the time of the initial wounding (0 hr) and post-wounding of corneas treated with vehicle, the indicated concentrations of a compound of Formula I or II, or AG1478. FIGS. 5B and 5C are a series of bar graphs quantifying the wound healing at 16 hours (FIG. 5B) or 24 hours (FIG. 5C) post wounding of corneas treated with vehicle, the indicated concentrations of a compound of Formula I or II, or AG1478. FIG. 5D is a graph showing the time-course wound healing of corneas treated with vehicle, the indicated concentrations of a compound of Formula I or II, or AG1478.

FIG. 6A is a series of images of epithelial wounds at the time of the initial wounding (0 hr) and post-wounding of corneas treated with vehicle, menadione, a compound of Formula I or II, or menadione in combination with a compound of Formula I or II. FIG. 6B is a series of bar graphs quantifying the wound healing at 16 hours or 24 hours post wounding of corneas treated with vehicle, menadione, a compound of Formula I or II, or menadione in combination with a compound of Formula I or II. FIG. 6C is a graph showing the time-course wound healing of corneas treated with vehicle, menadione, a compound of Formula I or II, or menadione in combination with a compound of Formula I or II.

Figure 7A:
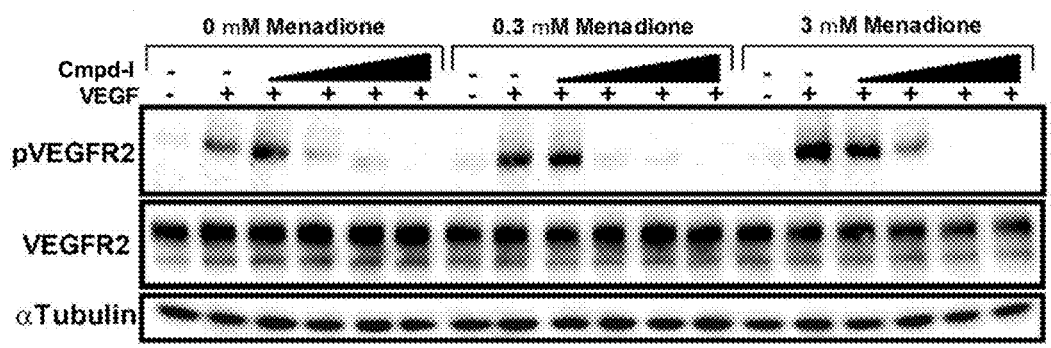
Figure 7B:
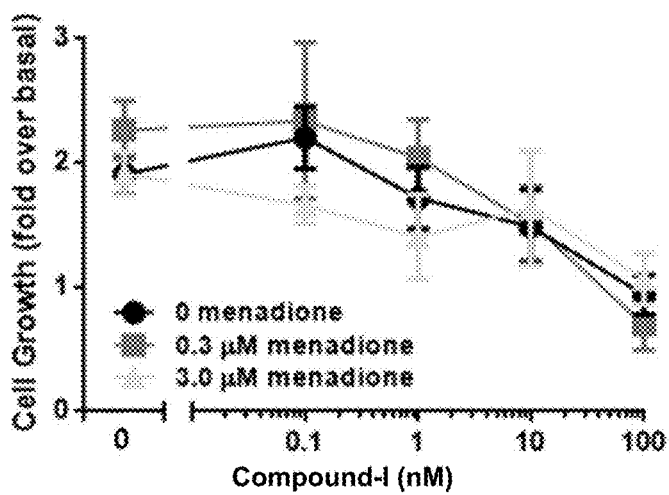

FIG. 7A is a series of immunoblots showing the total VEGFR2, phosphorylated VEGFR2, and α-tubulin (as loading control) in human retinal endothelial cells treated with the indicated concentrations of menadione for 4 hours, followed by 30 minutes treatment with varying concentrations of a compound of Formula I or II (1 nM, 10 nM, 100 nM, or 1 μM), and then 10 ng/ml VEGF. FIG. 7B is a graph quantifying growth of human retinal endothelial cells following treatment with the indicated concentrations of menadione for 4 hours, followed by 30 minutes treatment with varying concentrations of a compound of Formula I or II (0.1 nM, 1 nM, 10 nM, or 100 nM), and then 10 ng/ml VEGF overnight.

Figure 8:
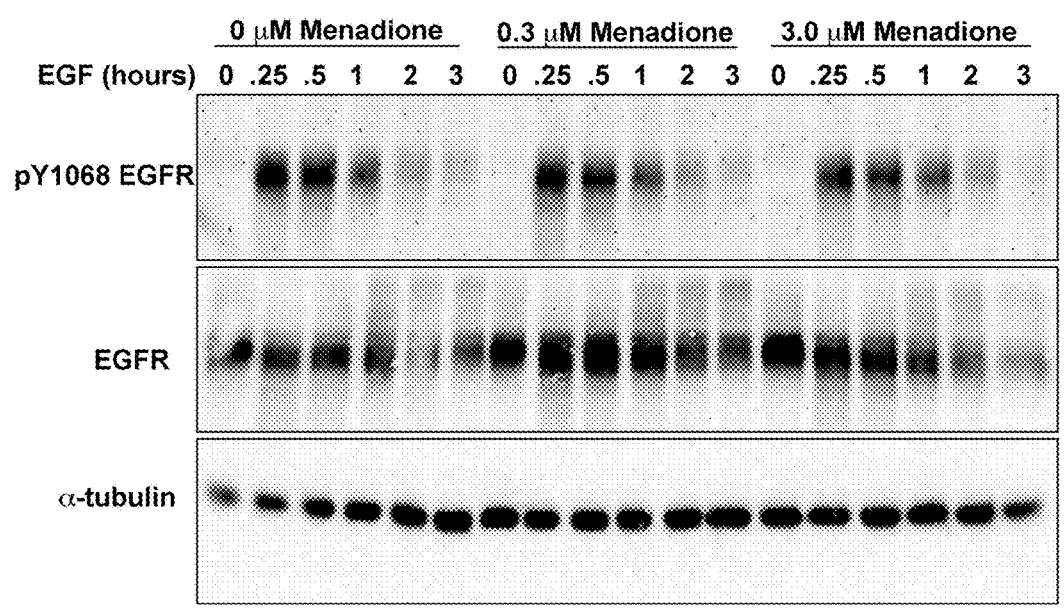

FIG. 8 is a series of immunoblots showing the total EGFR2, phosphorylated EGFR, and α-Tubulin (as loading control) in hTCEpi cells treated with the indicated concentrations of menadione for 4 hours, followed by incubation with 8.0 nM EGF for the indicated periods of time.

Figure 9A:
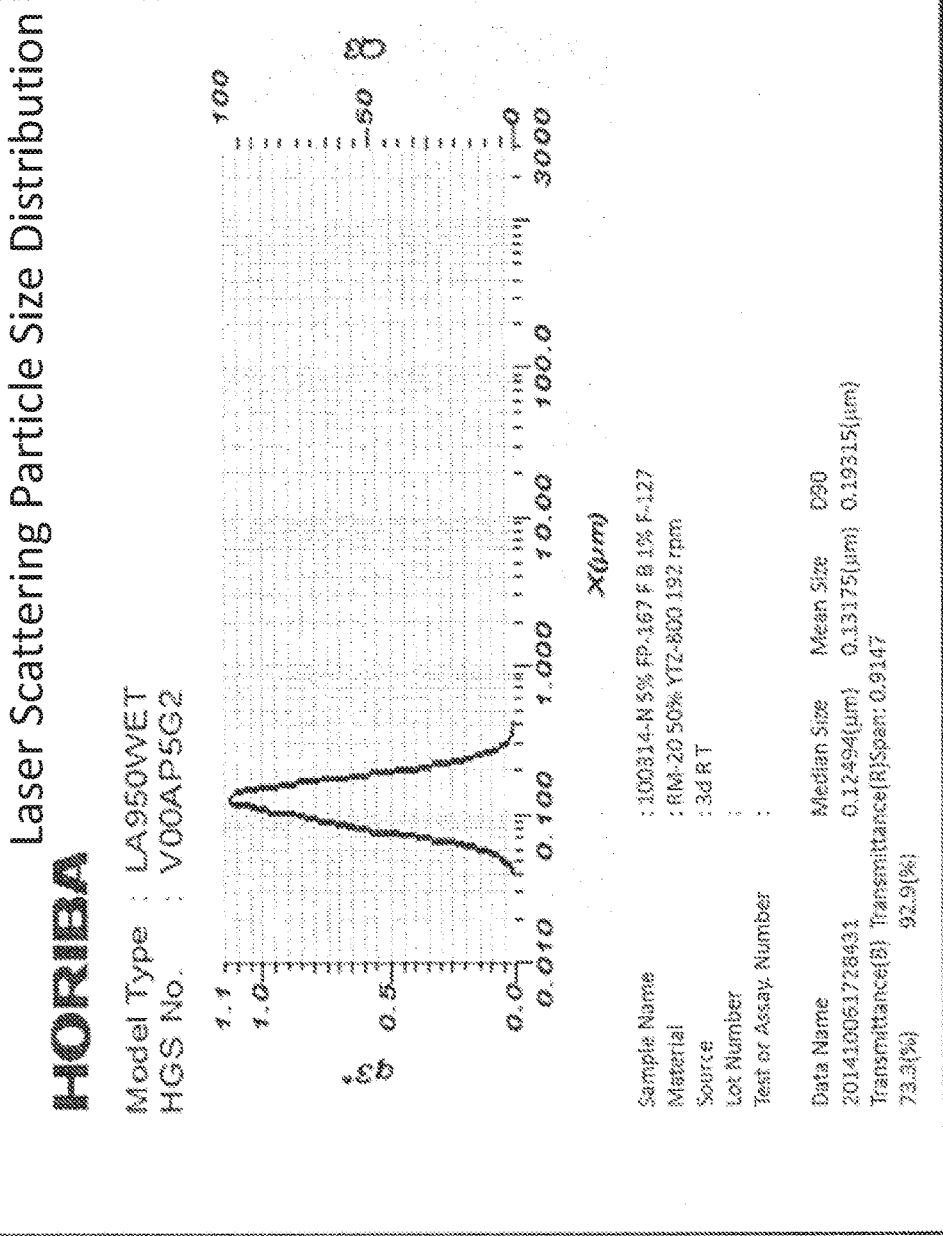
Figure 9B:
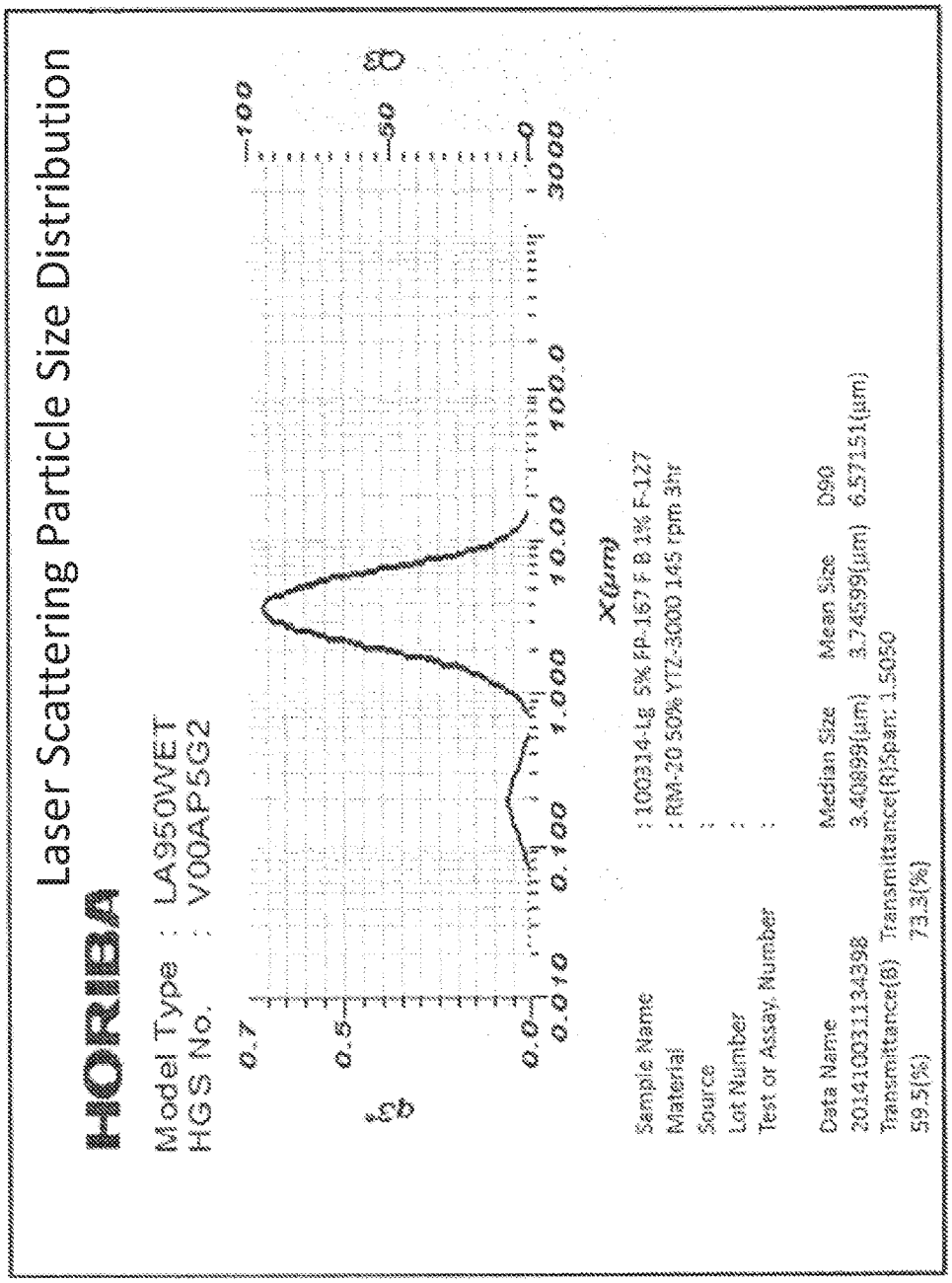
Figure 9C:
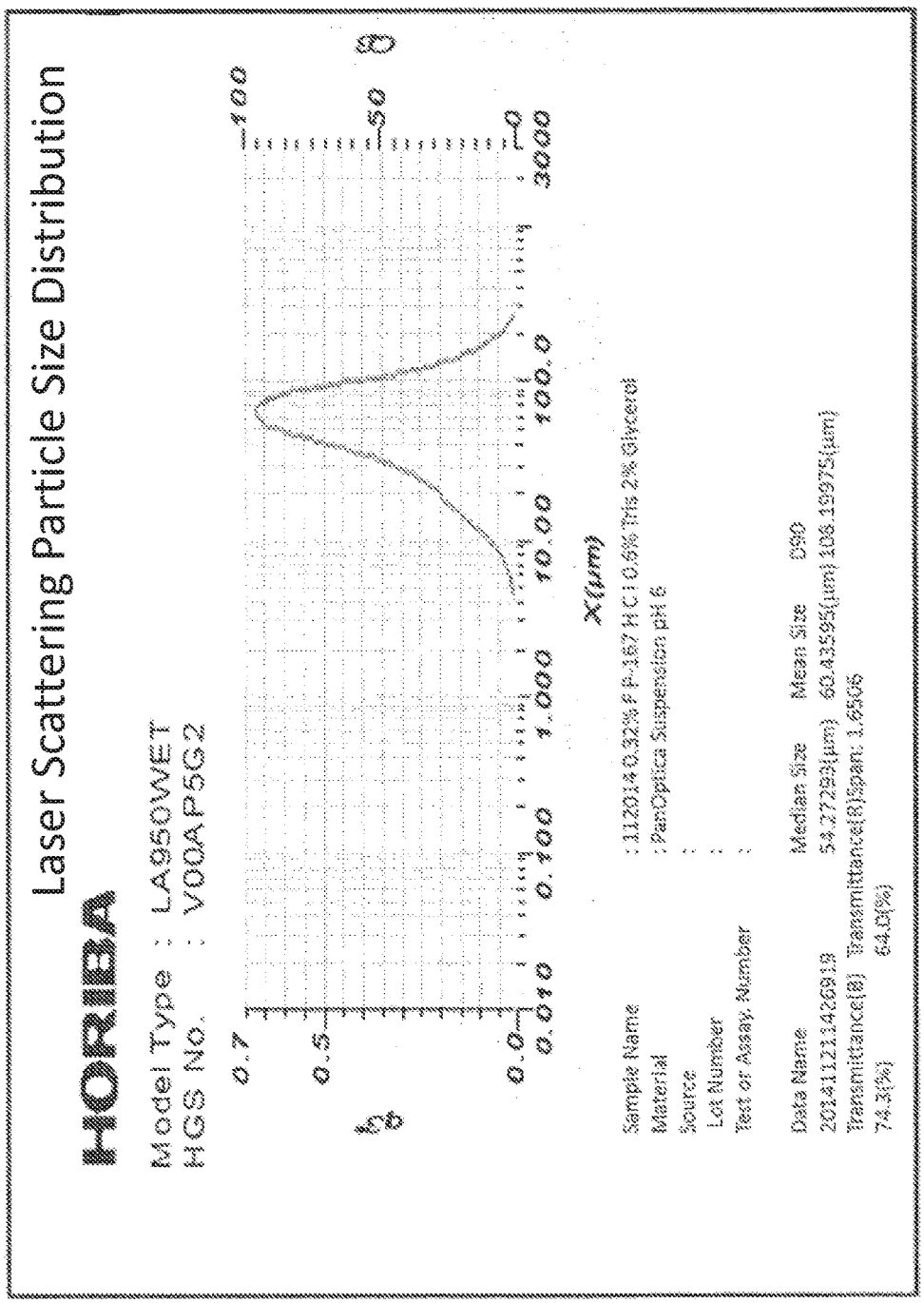
Figure 9D:
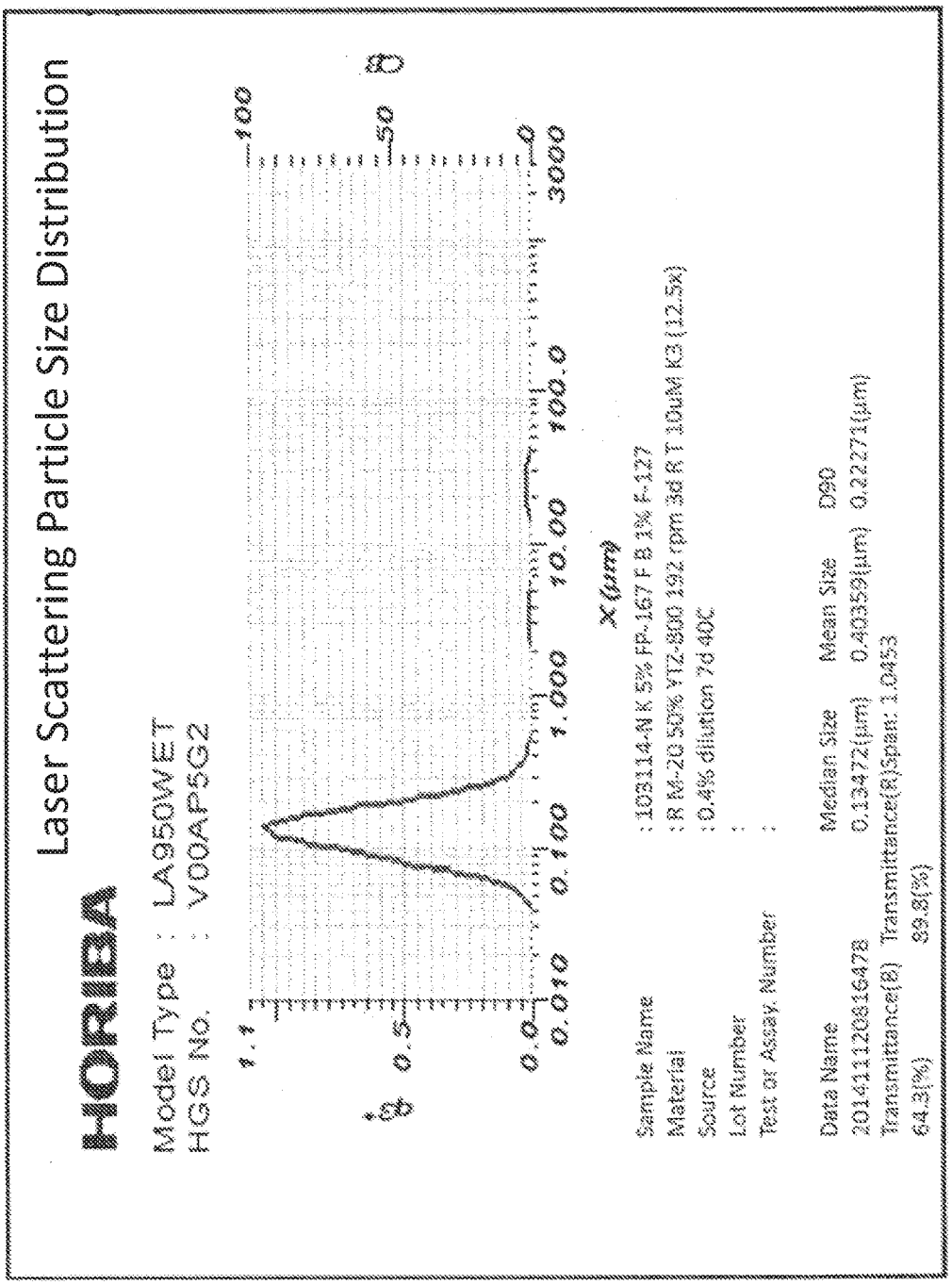

FIG. 9A shows the size distribution of the particles comprising 5% of a compound of Formula II and 1% Pluronic F-127 produced using small milling media for a long period of time at a high roller speed. FIG. 9B shows the size distribution of the particles comprising 5% of a compound of Formula II and 1% Pluronic F-127 produced using large milling media for a short period of time at a low roller speed. FIG. 9C shows the size distribution of the particles comprising 3% of Compound-I, 0.6% Tris HCl, and 2% glycerol produced without milling. FIG. 9D shows the size distribution of the particles comprising 0.4% of a compound of Formula II, 10 μM menadione, 0.08% Pluronic F-127, and 2.5% glycerol after storage at 40° C. for 7 days.

Figure 10:
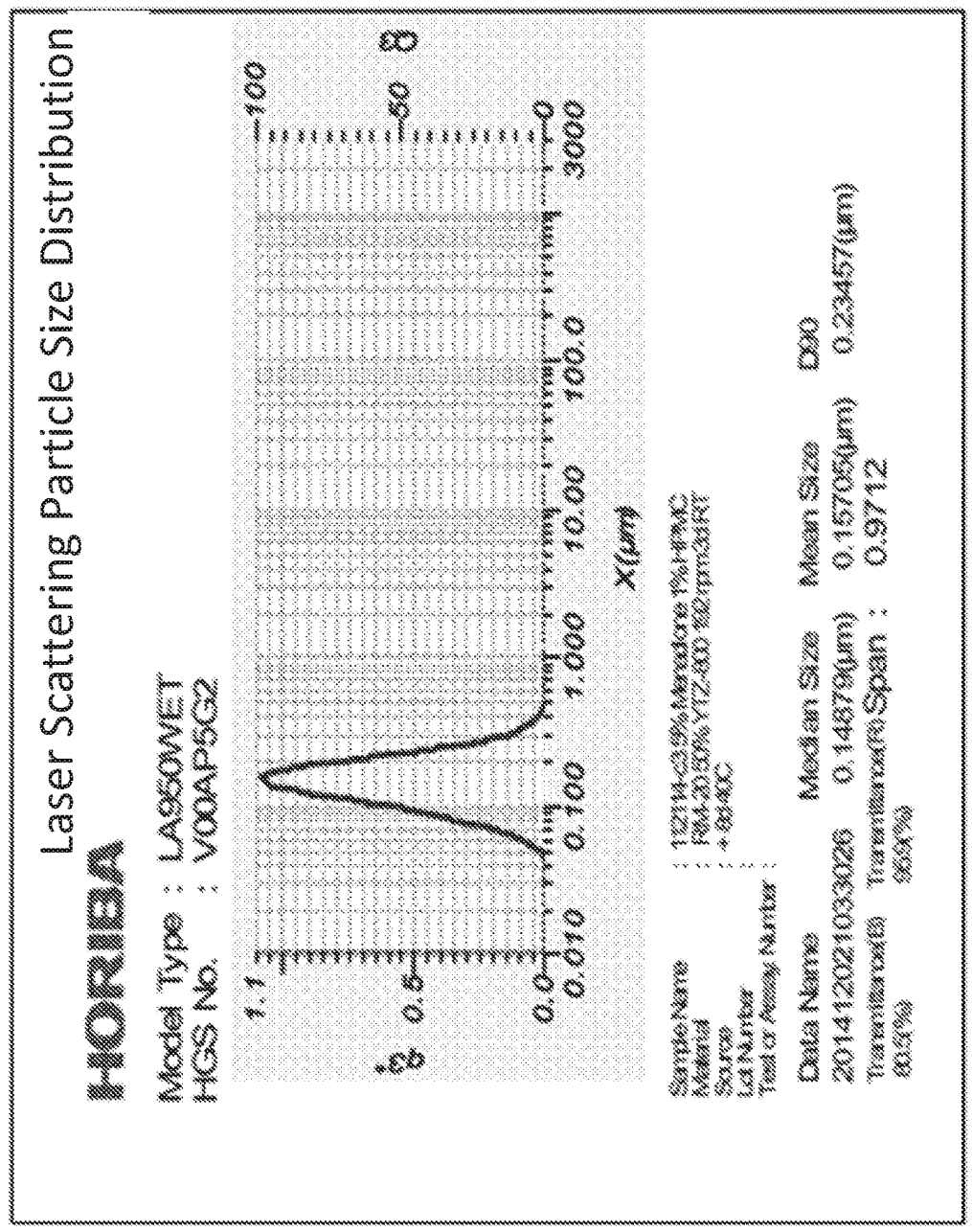

FIG. 10 shows the size distribution of the particles comprising 5% of menadione and 1% HPMC.

Figure 11A:
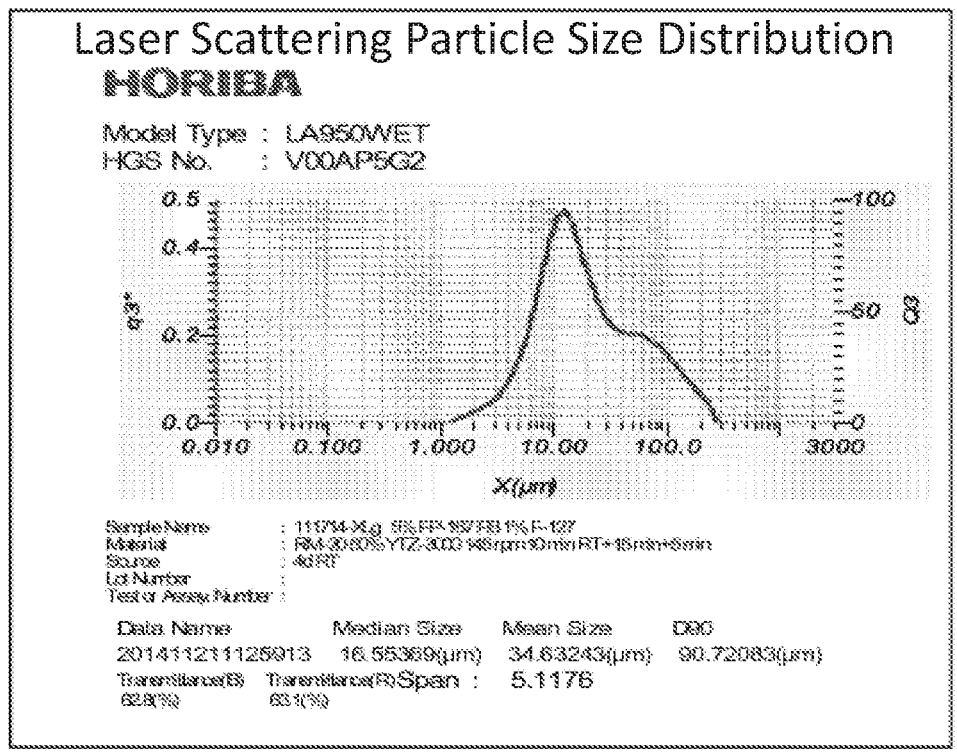
Figure 11B:
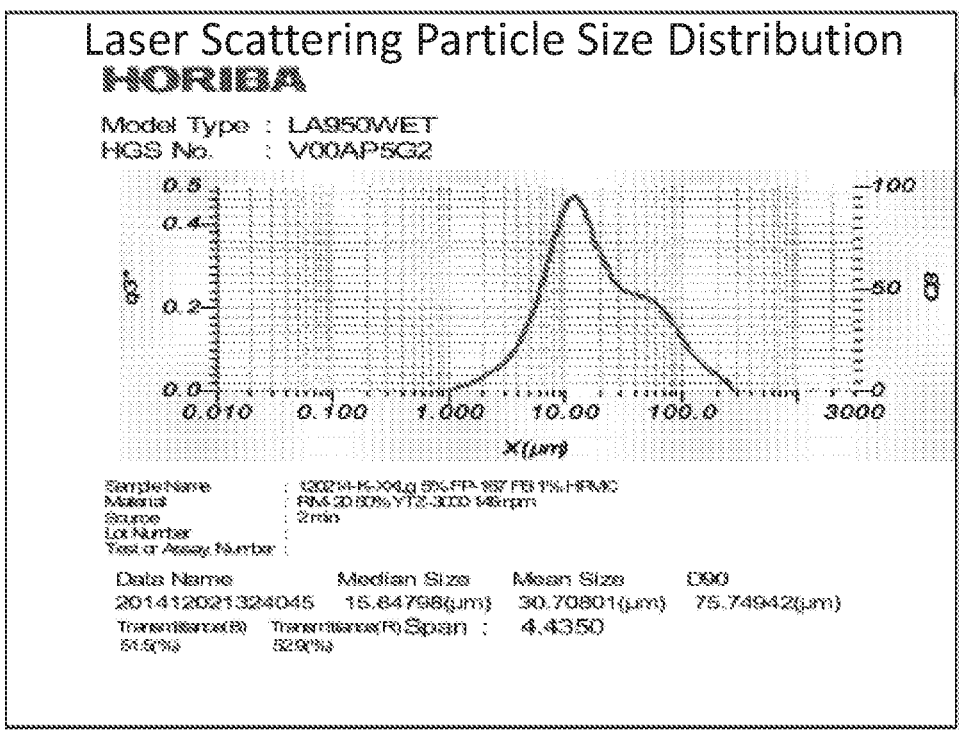

FIGS. 11A and 11B show the size distribution of the particles comprising 5% of a compound of Formula II and 1% Pluronic F-127 produced using large milling media for a short period of time at a low roller speed.

DETAILED DESCRIPTION

The materials, compounds, compositions, articles, and methods described herein may be understood more readily by reference to the following detailed description of specific aspects of the disclosed subject matter and the Examples included therein. Before the present materials, compounds, compositions, articles, devices, and methods are disclosed and described, it is to be understood that the aspects described below are not limited to specific methods or specific reagents, as such may vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

The present application provides compositions or formulations that contain a first active agent and/or a second active agent for use in the treatment of ocular disorders caused by endothelial cell proliferation, enhanced vascular permeability, inflammation, angiogenesis, or neovascularization, and a second active agent for use in the prevention and/or treatment of damage caused to the anterior of the eye by the first active agent, a systemic disease and/or an eye disease.

The present application also relates to a combination of a first active agent, e.g., a compound of Formula I or II, and a second active agent, e.g., nicotinic acid, nicotinamide, vitamin K, or a combination thereof. In one embodiment, a compound of Formula I or II, or a pharmaceutically acceptable salt thereof, and a second active agent or a pharmaceutically acceptable salt thereof, are administered simultaneously. Alternatively, a compound of Formula I or II, or a pharmaceutically acceptable salt thereof, is administered prior to administration of a second active agent, or a pharmaceutically acceptable salt thereof. In another embodiment, a compound of Formula I or II, or a pharmaceutically acceptable salt thereof, is administered after administration of a second active agent, or a pharmaceutically acceptable salt thereof.

The formulations of the application are useful in preventing or inhibiting neovascularization and vascular leakage associated with ocular disorders while preventing or inhibiting corneal diseases. In some cases, the formulations of the application cause regression of neovascularization. Briefly, within the context of the present application, the first active agents should be understood to be any molecule, either synthetic or naturally occurring, which acts to inhibit vascular growth, reduce vascular permeability, and/or decrease inflammation.

The formulations of the application are also useful in preventing and/or treating corneal epithelium disruptions caused by systemic diseases (e.g., cancer, diabetes, etc.), eye diseases, or a side effect from a locally or systemically administered drug (e.g., anti-EGFR agents, or compounds of Formula I or II having anti-EGFR activity). Briefly, within the context of the present application, the second active agents should be understood to be any molecule, either synthetic or naturally occurring, which acts to protect from and/or repair corneal edema, ulceration or any other corneal abnormality. In particular, the present application provides formulations comprising a first active agent and a second active agent each in a therapeutically effective amount.

General Definitions

In this specification and in the claims that follow, reference is made to a number of terms, which shall be defined to have the following meanings. All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition or formulation in which it is contained.

A weight percent of a component, unless specifically stated to the contrary, is based on the total weight of the formulation or composition in which the component is included.

By "effective amount" as used herein means "an amount of one or more of the disclosed compounds, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciate that the dosage regime may be altered to provide optimum therapeutic response. For example, several divided doses may be administered daily or the dose may be proportionally reduced as indicated by the exigencies of the therapeutic situation. In addition, the formulations of this disclosure can be administered as frequently as necessary to achieve a therapeutic amount.

The effective amount or effective dose in a human can be determined from that in an animal (e.g., an experimental animal). For example, the effective dose in a human may be calculated based on the conversion shown in the table below.

Conversion of animal doses to human-equivalent doses (HEDs) by using the exponent 0.67 for body surface area

| Species | HED from mg · kg$^{-1}$ dose in animal divide animal dose by | HED from mg · kg$^{-1}$ dose in animal multiply animal dose by |
| --- | --- | --- |
| Mouse | 12.3 | 0.081 |
| Hamster | 7.4 | 0.135 |
| Rat | 6.2 | 0.162 |
| Ferret | 5.3 | 0.189 |
| Guinea pig | 4.6 | 0.216 |
| Rabbit | 3.1 | 0.324 |
| Dog | 1.8 | 0.541 |
| Monkey | 3.1 | 0.324 |
| Marmoset | 6.2 | 0.162 |
| Squirrel monkey | 5.3 | 0.189 |
| Baboon | 1.8 | 0.541 |
| Micro-pig | 1.4 | 0.730 |
| Mini-pig | 1.1 | 0.946 |

"Excipient" is used herein to include any other compound that may be contained in or combined with one or more of the disclosed inhibitors that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients. For the purposes of the present application the term "excipient" and "carrier" are used interchangeably throughout the description of the present application and said terms are defined herein as, "ingredients which are used in the practice of formulating a safe and effective pharmaceutical composition."

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a primate or a human.

By "reduce" or other forms of the word, such as "reducing" or "reduction," is meant lowering of an event or characteristic (e.g., vascular leakage, or tissue swelling). It is understood that this is typically in relation to some standard or expected value, in other words it is relative, but that it is not always necessary for the standard or relative value to be referred to.

The term "treat" or other forms of the word such as "treated" or "treatment" is used herein to mean that administration of a compound or formulation of the present application mitigates a disease or a disorder in a host and/or reduces, inhibits, or eliminates a particular characteristic or event associated with a disorder (e.g., vascular leakage or corneal ulceration).

Insofar as the methods of the present application are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present application may occur prior to onset of a disease. The term does not imply that the disease state be completely avoided.

The term "ameliorating" or other forms of the word such as "ameliorate" is used herein to mean that administration of a therapeutic agent of the present application mitigates one or more symptoms of a disease or a disorder in a host and/or reduces, inhibits, or eliminates a particular symptom associated with the disease or disorder prior to and/or post administration of the therapeutic agent.

The disclosed first active agent compounds affect vascular leakage or pathological neovascularization by inhibiting a receptor tyrosine kinase. The disclosed second active agent compounds affect corneal epithelium disruptions by modulating (e.g., activating) a receptor tyrosine kinase.

Throughout the description and claims of this specification the word "comprise" and other forms of the word, such as "comprising" and "comprises," means including but not limited to, and is not intended to exclude, for example, other additives, or components.

As used in the description and the appended claims, the singular forms "a," "an," and "the" include plural referents unless the context clearly dictates otherwise.

"Optional" or "optionally" means that the subsequently described event or circumstance can or cannot occur, and that the description includes instances where the event or circumstance occurs and instances where it does not.

The term "about" refers to any minimal alteration in the concentration or amount of a therapeutic agent (e.g., a first active agent or a second active agent) that does not change the efficacy of the agent in preparation of a formulation and in treatment of a disease or disorder. For example, without being limiting, the concentration of a therapeutic agent would be effective if the concentration is varied between 0.005% to 5.0% (e.g., ±0.0005%). The term "about" with respect to concentration range of the therapeutic/active agents of the present application, e.g., first active agent or second active agent, also refers to any variation of a stated amount or range which would be an effective amount or range.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "halo", as used herein, unless otherwise indicated, includes fluoro, chloro, bromo or iodo. Preferred halo groups are fluoro, chloro and bromo.

The term "alkyl," as used herein, unless otherwise indicated, includes both branched and straight-chain saturated aliphatic hydrocarbon groups having the specified number of carbon atoms. For example, $C_{1-6}$alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl. In certain embodiments, a straight chain or branched chain alkyl has six or fewer carbon atoms in its backbone (e.g., $C_1$-$C_6$ for straight chain, $C_3$-$C_6$ for branched chain), and in another embodiment, a straight chain or branched chain alkyl has four or fewer carbon atoms. Likewise, cycloalkyls have from three to eight carbon atoms in their ring structure, and in other embodiments, cycloalkyls have five or six carbons in the ring structure.

Alkyl can be substituted by replacing hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above and additional substituents such as alkyl, alkenyl, and alkynyl. An "alkylaryl" or an "aralkyl" moiety is an alkyl substituted with an aryl (e.g., phenylmethyl (benzyl)).

The term "alkenyl," as used herein, unless otherwise indicated, includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has six or fewer carbon atoms in its backbone (e.g., $C_2$-$C_6$ for straight chain, $C_3$-$C_6$ for branched chain). Likewise, cycloalkenyl groups may have from three to eight carbon atoms in their ring structure, and in some embodiments, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms. Alkenyl can be substituted by replacing hydrogen on one or more hydrocarbon backbone carbon atoms. Such substituents can include, for example, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl", as used herein, unless otherwise indicated, includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. Alkynyl can be substituted by replacing hydrogen on one or more hydrocarbon backbone carbon atoms. Such substituents can include, for example, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkoxy," as used herein, unless otherwise indicated, includes O-alkyl groups wherein "alkyl" is as defined above.

The term "aryl," as used herein, unless otherwise indicated, includes 5- and 6-membered "unconjugated", or single-ring, aromatic groups, as well as "conjugated", or multicyclic, systems with at least one aromatic ring. Examples of aryl groups include benzene, phenyl, and the like. Furthermore, the term "aryl" includes multicyclic aryl groups, e.g., tricyclic, bicyclic, e.g., naphthalene.

Aryl groups having heteroatoms in the ring structure may be referred to as "aromatic heterocycles", "aryl heterocycles", "heterocycles," "heteroaryls" or "heteroaromatics".

The aryl or heteroaryl can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

The term "4-10 membered heterocyclic," as used herein, unless otherwise indicated, includes aromatic and non-aromatic heterocyclic groups containing one or more heteroatoms each selected from O, S and N, wherein each heterocyclic group has from 4-10 atoms in its ring system. Non-aromatic heterocyclic groups include groups having only 4 atoms in their ring system, but aromatic heterocyclic groups must have at least 5 atoms in their ring system. An example of a 4 membered heterocyclic group is azetidinyl (derived from azetidine). An example of a 5 membered heterocyclic group is thiazolyl and an example of a 10 membered heterocyclic group is quinolinyl.

Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl.

Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The foregoing groups, as derived from the compounds listed above, may be C-attached or N-attached where such is possible. For instance, a group derived from pyrrole may be pyrrol-1-yl (N-attached) or pyrrol-3-yl (C-attached). The "4-10 membered heterocyclic" moiety can be substituted.

The phrase "pharmaceutically acceptable salt(s)," as used herein, unless otherwise indicated, includes salts of acidic or basic groups which may be present in the compounds of first active agents (e.g., Formula I or II) or second active agents. The compounds of Formula I or II and the second active agents that are basic in nature are capable of forming a wide variety of salts with various inorganic and organic acids. The acids that may be used to prepare pharmaceutically acceptable acid addition salts of such basic compounds of Formula I or II and second active agents are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of first active agents (e.g., Formula I or II) and second active agents that are acidic in nature are capable of forming base salts with various pharmacologically acceptable cations. Examples of such salts include the alkali metal or alkaline earth metal salts and particularly, the sodium and potassium salts.

In some embodiments, the salt is an acid addition salt, e.g. HCl salt.

Certain compounds of Formula I or II and certain second active agents may have asymmetric centers and therefore exist in different enantiomeric forms. This application relates to the use of all optical isomers and stereoisomers of the compounds of Formula I or II and mixtures thereof and of the second active agents and mixtures thereof. The compounds of Formula I or II and the second active agents may also exist as E/Z geometric isomers or tautomers. This application relates to the use of all such geometric isomers and tautomers and mixtures thereof.

The subject application also includes isotopically-labeled compounds, and the pharmaceutically acceptable salts thereof, which are identical to those recited in Formula I or II, but for the fact that one or more atoms are replaced by an atom having an atomic mass or mass number different from the atomic mass or mass number usually found in nature. Examples of isotopes that can be incorporated into compounds of the application include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds of the Formula I or II, conjugates thereof, and pharmaceutically acceptable salts of said compounds or of said conjugates which contain the aforementioned isotopes and/or other isotopes of other atoms are within the scope of this application. Certain isotopically-labeled compounds of the present application (e.g., compounds of Formula I or II), for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$ isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula I or II of this application and esters or lipid conjugates thereof can generally be prepared by carrying out the procedures disclosed in the Schemes and/or in the Examples and Preparations below, by substituting a readily available isotopically labeled reagent for a non-isotopically labeled reagent.

This application also encompasses pharmaceutical formulations containing derivatives of compounds of the Formula I or II, or pharmaceutically acceptable salts thereof and of the second active agents, or pharmaceutically acceptable salts thereof. Compounds of Formula I or II, or pharmaceutically acceptable salts thereof, and second active agents, or pharmaceutically acceptable salts thereof, having free amino, or amido groups can be converted into conjugated derivatives, wherein an amino acid residue, or a polypeptide chain of two or more (e.g., two, three or four) amino acid residues is covalently joined through an amide or ester bond to a free amino group of compounds of Formula I or II, or pharmaceutically acceptable salts thereof, or of second active agents or pharmaceutically acceptable salts thereof. The amino acid residues include, but are not limited to, the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of derivatives are also encompassed. Amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, et al., ADVANCED DRUG DELIVERY REVIEWS (1996) 19, 115. Carbamate conjugates of hydroxy and amino groups are also included, as are carbonate conjugates and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Derivatives of this type are described in R. P. Robinson et al., J. MEDICINAL CHEMISTRY (1996) 39, 10.

The term "kinase" refers to any enzyme that catalyzes the addition of phosphate groups to a protein residue; for example, serine and threonine kinases catalyze the addition of phosphate groups to serine and threonine residues.

The terms "VEGFR kinase," and "VEGFR," refer to any of the vascular endothelial growth factor receptors.

The terms "VEGF signaling," and "VEGF cascade" refer to both the upstream and downstream components of the VEGF signaling cascade.

The terms "ErbB kinase," and "ErbB receptor," refer to any member of the ErbB family of receptor tyrosine kinases including EGFR (ErbB1 or HER1), HER2/c-neu (ErbB2), HER3 (ErbB3) and HER4 (ErbB4).

The terms "EGF signaling," and "EGF cascade" refer to both the upstream and downstream components of the EGF signaling cascade.

The term "pharmaceutically acceptable" refers to the fact that the carrier, diluent or excipient must be compatible with the other ingredients of the formulation and not deleterious to the recipient thereof.

The terms "administration of a compound" or "administering a compound" refer to the act of providing a compound of the application or pharmaceutical formulation to the subject in need of treatment.

The term "vasculostasis" refers to the maintenance of the homeostatic vascular functioning leading to the normal physiologic functioning.

The term "vasculostatic agents" refers to agents that seek to address conditions in which vasculostasis is compromised by preventing the loss of or restoring or maintaining vasculostasis.

In the present application "composition" and "formulation" are used interchangeably and refer to the conventional understanding, as known in the art, of a composition or formulation.

The present application relates to an ophthalmic formulation. In some embodiments, the ophthalmic formulation of the present application is a gel formulation or a semi-gel formulation, or both.

"Gel" according to the present application is a semi-solid dosage form of the present application, containing suspended particles. A semisolid is not pourable; it does not flow or conform to its container at room temperature. A semisolid does not flow at low shear stress and generally exhibits plastic flow behavior. A colloidal dispersion is a system in which particles of colloidal dimension (i.e., typically between 1 nm and 1 μm) are distributed uniformly throughout a liquid.

In some embodiments, "gel" is a semisolid system consisting either of suspensions of small inorganic particles or of organic molecules interpenetrated by a liquid. "Gels" are classed either as single-phase or two-phase systems. "Gels" also consist of a mesophase, or state of matter intermediate between a liquid and a solid that represents a partially ordered structure, which is the state for the active agents in the "Gel Drop" of the present embodiments. A two-phase gel consists of a network of small discrete particles. In a two-phase system, the gel mass sometimes is referred to as magma (e.g., Bentonite Magma) if the particle size of the suspended material is large. Both gels and magmas are thixotropic, forming semisolids on standing and becoming liquid on agitation. The semisolid formulations should be shaken before administration to ensure homogeneity and should be so labeled (see Suspensions). Single-phase gels consist of organic macromolecules uniformly distributed throughout a liquid in such a manner that no apparent boundaries exist between the dispersed macromolecules and the liquid. Single phase gels may also consist of organic low molecular weight (LMW) molecules where the component responsible for gelation is the actual active ingredient. These so called "LMW hydrogels" are different from traditional gelators of water such as high molecular weight synthetic polymers, polysaccharides, and proteins. High molecular weight gelators are highly ordered and uni-directional due to hydrogen bonding whereas the forces governing LMW hydrogels are largely non-directional van der Waals forces (hydrophobic) interactions. In practice LMW hydrogels are observed as highly anisotropic (typically fibrillar) structures that propagate throughout the liquid yielding a physically branched or entangled network. The gels can thus be non-ordered to slightly ordered showing some birefringence, liquid crystal character. Gels are administered topically or, after shaking, in the form of a hydrogel as an eye drop.

The semisolid "gel" according to the present application is a semisolid per USP definitions and literature referenced therein. The semisolid formulation apparent viscosity increases with concentration. The clinical dosage strength of the present formulation ranges from a low strength of ≤1 mg/mL (0.1%) to a high strength of ≤6 mg/mL (0.6%). Low strength doses are least viscous and fall under the category of a "solution," whereas higher strengths are more viscous and fit the definition of a gel.

"Jelly" according to the present application is a class of gels, which are semisolid systems that consist of suspensions made up either small inorganic particles or large organic molecules interpenetrated by a liquid, in which the structural coherent matrix contains a high portion of liquid, usually water.

"Solution" according to the present application is a clear, homogeneous liquid dosage form that contains one or more chemical substances dissolved in a solvent or mixture of mutually miscible solvents. A solution is a liquid preparation that contains one or more dissolved chemical substances in a suitable solvent or mixture of mutually miscible solvents. Because molecules of a drug substance in solution are uniformly dispersed, the use of solutions as dosage forms generally provides assurance of uniform dosage upon administration and good accuracy when the solution is diluted or otherwise mixed.

"Liquid" according to the present application is a dosage form consisting of a pure chemical in its liquid state. A liquid is pourable; it flows and conforms to its container at room temperature. Liquids display Newtonian or pseudoplastic flow behavior.

"Suspension" according to the present application is a liquid dosage form that contains solid particles dispersed in a liquid vehicle.

The compounds of first active agents (e.g., Formula I or II) and the second active agents are formulated into therapeutic formulations as natural or salt forms. Pharmaceutically acceptable non-toxic salts include the base addition salts (formed with free carboxyl or other anionic groups) which are derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts are formed as acid addition salts with any free cationic groups and generally are formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the application include amine salts formed by the protonation of an amino group with inorganic acids such as hydrochloric acid, hydrobromic acid, hydroiodic acid, sulfuric acid, phosphoric acid, and the like. Salts of the application also include amine salts formed by the protonation of an amino group with suitable organic acids, such as p-toluenesulfonic acid, acetic acid, and the like. Additional excipients which are contemplated for use in the practice of the present application are those available to those of ordinary skill in the art, for example, those found in the United States Pharmacopoeia Vol. XXII and National Formulary Vol. XVII, U.S. Pharmacopoeia Convention, Inc., Rockville, Md. (1989), the relevant contents of which is incorporated herein by reference. In addition, polymorphs of the application compounds are included in the present application.

The embodiments of the present application provide an ophthalmic composition or formulation for treating ocular neovascularization with a first active agent of Formula I:

(I)

or a pharmaceutically acceptable salt thereof; a second active agent or a pharmaceutically acceptable salt thereof, wherein the second active agent is nicotinic acid, nicotinamide, or vitamin K, or a combination thereof; and pharmaceutically acceptable excipients; the first active agent or the pharmaceutically acceptable salt is present in about 0.02% to about 1.2% w/v, wherein:

$X^1$ is O or S;

$R^1$ is H, $C_1$-$C_{10}$ alkyl, $C_2$-$C_{10}$ alkenyl, $C_2$-$C_{10}$ alkynyl, $C(O)(C_1$-$C_{10}$ alkyl), $(CH_2)_t(C_6$-$C_{10}$ aryl), $(CH_2)_t$ (4-10 membered heterocyclic), $C(O)(CH_2)_t(C_6$-$C_{10}$ aryl), or $C(O)(CH_2)_t$ (5-10 membered heterocyclic), wherein:
  t is an integer from 0 to 5;
  the alkyl group optionally includes 1 or 2 hetero moieties selected from O, S and $N(R^6)$ with the proviso that two O atoms, two S atoms, or an O and an S atoms are not attached directly to each other;
  the aryl and heterocyclic groups are optionally fused with a $C_6$-$C_{10}$ aryl group, a $C_5$-$C_8$ saturated cyclic group, or a 5-10 membered heterocyclic group;
  1 or 2 carbon atoms in the foregoing heterocyclic moieties are optionally substituted with an oxo (=O) moiety or an anion of oxygen;
  the $(CH_2)_t$ moieties optionally include a carbon-carbon double or triple bond when t is an integer from 2 to 5; and
  the foregoing $R^1$ groups, except H, are optionally substituted with 1 to 3 $R^4$ groups;

$R^2$ is H;

$R^3$ is $(CH_2)_t(C_6$-$C_{10}$ aryl), wherein:
  t is an integer from 0 to 5;
  the aryl group is optionally fused with a $C_6$-$C_{10}$ aryl group, a $C_5$-$C_8$ saturated cyclic group, or a 5-10 membered heterocyclic group;

the (CH$_2$)$_t$ moieties optionally include a carbon-carbon double or triple bond when t is an integer from 2 to 5; and each R$^4$ is independently selected from C$_1$-C$_{10}$ alkyl, C$_2$-C$_{10}$ alkenyl, C$_2$-C$_{10}$ alkynyl, halo, cyano, nitro, trifluoromethyl, trifluoromethoxy, azido, OR$^5$, C(O)R$^5$, C(O)OR$^5$, NR$^6$C(O)R$^5$, NR$^6$C(O)OR$^5$, OC(O)R$^5$, NR$^6$SO$_2$R$^5$, SO$_2$NR$^5$R$^6$, C(O)NR$^5$R$^6$, NR$^5$R$^6$, S(O)$_j$R$^7$ where j is an integer from 0 to 2, SO$_3$H, NR$^5$(CR$^6$R$^7$)$_t$OR$^6$, (CH$_2$)$_t$(C$_6$-C$_{10}$ aryl), SO$_2$(CH$_2$)$_t$(C$_6$-C$_{10}$ aryl), S(CH$_2$)$_t$(C$_6$-C$_{10}$ aryl), O(CH$_2$)$_t$(C$_6$-C$_{10}$ aryl), (CH$_2$)$_t$ (5-10 membered heterocyclic), and (CR$^6$R$^7$)$_m$OR$^6$, wherein:

m is an integer from 1 to 5;
t is an integer from 0 to 5;
the alkyl group optionally includes 1 or 2 hetero moieties selected from O, S and N(R$^6$) with the proviso that two O atoms, two S atoms, or an O and an S atoms are not attached directly to each other;
the aryl and heterocyclic groups are optionally fused with a C$_6$-C$_{10}$ aryl group, a C$_5$-C$_8$ saturated cyclic group, or a 5-10 membered heterocyclic group;
1 or 2 carbon atoms in the foregoing heterocyclic moieties are optionally substituted with an oxo (=O) moiety or an anion of oxygen; and
the alkyl, aryl and heterocyclic moieties of the foregoing R$^4$ groups are optionally substituted with 1 to 3 substituents independently selected from halo, cyano, nitro, trifluoromethyl, trifluoromethoxy, azido, NR$^6$SO$_2$R$^5$, SO$_2$NR$^5$R$^6$, C(O)R$^5$, C(O)OR$^5$, OC(O)R$^5$, NR$^6$C(O)R$^5$, C(O)NR$^5$R$^6$, NR$^5$R$^6$, (CR$^6$R$^7$)$_m$OR$^6$ where m is an integer from 1 to 5, OR$^5$, and the substituents listed in the definition of R$^5$; and
R$^5$, R$^6$, and R$^7$ are each independently H or C$_1$-C$_6$ alkyl.

In one embodiment, R$^3$ is (CH$_2$)$_t$(C$_6$-C$_{10}$ aryl), wherein t is an integer from 1 to 3 and R$^3$ is optionally substituted with 1 to 4 R$^4$ groups.

In a further embodiment, R$^3$ is benzyl, optionally substituted with 1 to 4 substituents independently selected from halo and C$_1$-C$_4$ alkyl. In a further embodiment, R$^3$ is benzyl substituted with 1 to 4 substituents independently selected from methyl, fluoro, chloro and bromo.

In one embodiment, R$^1$ is (CH$_2$)$_t$ (5-10 membered heterocyclic), wherein t is an integer from 0 to 5, optionally substituted with 1 or 2 substituents independently selected from C$_1$-C$_4$ alkyl, hydroxy and hydroxymethyl.

The present application provides heterocyclic moiety of the R$^1$ group in Formula I selected from morpholino, pyrrolidinyl, imidazolyl, piperazinyl, piperidinyl, and 2,5-diaza-bicyclo[2.2.1]hept-2-yl, the t variable of the R$^1$ group ranges from 2 to 5, and the R$^1$ group is optionally substituted with one or more hydroxy groups.

For example, the heterocyclic moiety of the R$^1$ group in Formula I of the present application is pyrrolidine.

In further embodiments of the present application, the first active agent is:

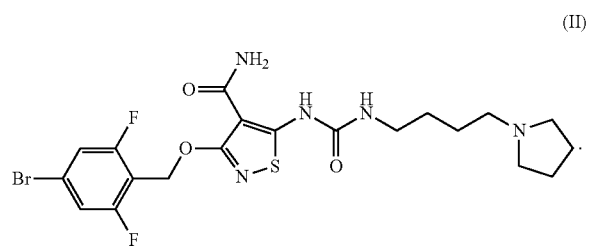 [SMILES: NC(=O)c1c(OCc2c(F)cc(Br)cc2F)nsc1NC(=O)NCCCCN1CCCC1]

(II)

A compound of the present application is 3-[(4-bromo-2,6-difluorophenyl)methoxy]-5-[[[[4-(1-pyrrolidinyl)butyl]amino]carbonyl]amino]-4-isothiazolecarboxamide hydrochloride, of molecular formula: C$_{20}$H$_{24}$BrF$_2$N$_5$O$_3$S.HCl, molecular weight: 568.86 g/mol, and with the property that the molecule does not contain an asymmetric center and is not chiral. A compound of the present application is represented by Compound-I:

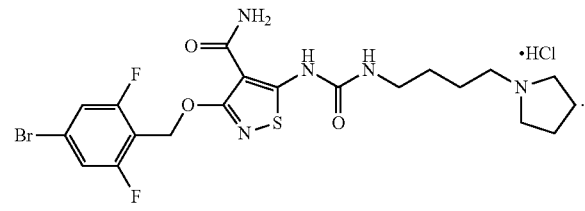

(Compound-I)

The Compound-I of the present application is an inhibitor of the tyrosine kinase activity of VEGFR-2, which blocks VEGF-stimulated auto-phosphorylation of this receptor as well as endothelial cell proliferation. It is selective (>500×) relative to the concentration required to inhibit the epidermal growth factor receptor (EGFR) and the insulin receptor (IR) tyrosine kinases. Compound-I is described in U.S. Pat. No. 6,235,764. In some embodiments, the compounds of Formula I or II are VEGFR-2 inhibitors.

The second active agents of the present application are EGFR modulators (e.g., activators) of the tyrosine kinase activity of EGFR.

The first active agent and the second active agent can be administered together as part of the same formulation comprising the first active agent, the second active agent, and a pharmaceutical excipient. The first active agent and the second active agent can also be administered separately. In one embodiment, the first active agent and the second active agent are administered separately as two formulations, wherein one formulation comprises the first active agent and a pharmaceutical excipient, and the second formulation comprises the second active agent and a pharmaceutical excipient.

In one embodiment, a compound of Formula I or II, or a pharmaceutically acceptable salt thereof, and the second active agent or a pharmaceutically acceptable salt thereof, are administered simultaneously. Alternatively, a compound of Formula I or II, or a pharmaceutically acceptable salt thereof, is administered prior to administration of the second active agent, or a pharmaceutically acceptable salt thereof. In another embodiment, a compound of Formula I or II, or a pharmaceutically acceptable salt thereof, is administered after administration of the second active agent, or a pharmaceutically acceptable salt thereof.

General Properties

Compound-I of the present application has the characteristics as shown in Table 1. The embodiments provide three formulations of Compound-I or its free base—the Formula II compound.

TABLE 1A

General Properties of Compound-I Drug Substance

| Property | Result |
| --- | --- |
| Chemical Name [CAS No] Codes: Compound-I | 3-[(4-bromo-2,6-difluorophenyl)methoxy]-5-[[[[4-(1-pyrrolidinyl)butyl]amino]carbonyl]amino]-4-isothiazolecarboxamide hydrochloride [252003-71-7] |
| Appearance (color, physical form) | White crystalline solid |
| Melting range | 222.2-224.8° C. |
| pKa (water) | 10.5 |
| Solubility (mg/mL) | Methanol: 4.3 |
| | Ethanol: 0.7 |
| | Acetonitrile: 0.04 |
| | Tetrahydrofuran: 0.02 |
| | Hexanes: <0.01 |
| | 0.1N NaOH: 0.05 |
| | pH 9.0 (0.05m $Na_2HPO_4$): 0.7 |
| | pH 7.5 (0.05M $NaH_2PO_4$): 1.0 |
| | 0.1N HCl: 0.04 |
| | Deionized water 0.5-1.2[b] |

The composition of Compound-I formulations are listed in Table 1B. The formulation materials are listed in Table 1C.

TABLE 1B

Compound-I formulations: Gel Drop, suspension, and solution.

| Formulation Forms | Composition |
| --- | --- |
| Ophthalmic gel drops | 0.05% Sodium Phosphate, Monobasic, Monohydrate<br>1.0-2.0% Glycerin<br>with or without 0.005% Benzalkonium Chloride, NF (BAK)<br>pH ~6.0-7.0 |
| Tris-based suspensions | 0.6% Tromethamine, USP (Tris)<br>1.0-2.0% Glycerin, USP<br>with or without 0.005% Benzalkonium Chloride, NF (BAK)<br>pH ~6.0-7.0 |
| Cyclodextrin-based solutions | 1% to 20% hydroxypropyl-β-cyclodextrin (HP-β-CD, KLEPTOSE ® HPB)<br>0.1% to 0.9% sodium chloride<br>pH ~6.0-7.0<br>or<br>1% to 20% sulfobutylether-β-cyclodextrin (SBE-β-CD, CAPTISOL ®)<br>with or without 0.122% Tromethamine (Tris)<br>0.1-0.2% sodium phosphate, dibasic, anhydrous<br>0%-0.6% sodium chloride<br>pH ~6.0-7.0<br>or<br>1% to 20% HP-β-CD (KLEPTOSE ® HPB or KLEPTOSE ® HP)<br>0.1-0.2% sodium phosphate, dibasic, anhydrous<br>0.50%-0.6% sodium chloride<br>pH ~6.0-7.0 |

TABLE 1C

Formulation materials

| Material | Function |
| --- | --- |
| Compound-I | Active Drug Substance |
| Sodium Chloride | Tonicity Modifier |
| Sulfobutyl ether-β-cyclodextrin (CAPTISOL ®, SβECD) 2-hydroxypropyl-β-cyclodextrin (KLEPTOSE ® HPB Parenteral Grade, HPβCD) | Solubilizing agents |
| Trometamol (Tris) Dibasic phosphate buffer | Buffer |
| 2.0N NaOH 0.1N HCl | Adjust pH |

The composition of the Compound-I formulations and a second active are listed in Table 1D. The formulation materials are listed in Table 1E.

TABLE 1D

Compound-I formulations: Gel Drop, suspension, and solution.

| Formulation Forms | Composition |
| --- | --- |
| Ophthalmic gel drops | 0.05% Sodium Phosphate, Monobasic, Monohydrate<br>1.0-2.0% Glycerin<br>with or without 0.005% Benzalkonium Chloride, NF (BAK)<br>pH ~6.0-7.0 |
| Tris-based suspensions | 0.6% Tromethamine, USP (Tris)<br>1.0-2.0% Glycerin, USP<br>with or without 0.005% Benzalkonium Chloride, NF (BAK)<br>pH ~6.0-7.0 |
| Cyclodextrin-based solutions | 1% to 20% hydroxypropyl-β-cyclodextrin (HP-β-CD, KLEPTOSE ® HPB)<br>0.1% to 0.9% sodium chloride<br>pH ~6.0-7.0<br>or<br>1% to 20% sulfobutylether-β-cyclodextrin (SBE-β-CD, CAPTISOL ®)<br>with or without 0.122% Tromethamine (Tris)<br>0.1-0.2% sodium phosphate, dibasic, anhydrous<br>0%-0.6% sodium chloride<br>pH ~6.0-7.0<br>or<br>1% to 20% HP-β-CD (KLEPTOSE ® HPB or KLEPTOSE ® HP)<br>0.1-0.2% sodium phosphate, dibasic, anhydrous<br>0.50%-0.6% sodium chloride<br>pH ~6.0-7.0 |

TABLE 1E

Formulation materials

| Material | Function |
| --- | --- |
| Compound-I | Active Drug Substance |
| Second active agent | Active Drug substance |
| Sodium Chloride | Tonicity Modifier |
| Sulfobutyl ether-β-cyclodextrin (CAPTISOL ®, SβECD) 2-hydroxypropyl-β-cyclodextrin (KLEPTOSE ® HPB Parenteral Grade, HPβCD) | Solubilizing agents |
| Trometamol (Tris) Dibasic phosphate buffer | Buffer |
| 2.0N NaOH 0.1N HCl | Adjust pH |

Ophthalmic Solutions

The present application provides formulations of a first active agent (e.g., Compound-I and/or its free base (Formula II compound)) and/or a second active agent, formed as a solution with viscosity similar to water. The solution includes pharmaceutically acceptable agents/excipients, for example, without being limiting, cyclodextrin. The solution thus formed is clear and colorless solution, suitable for topical administration to the eye.

The solutions of the present application reduce anterior segment exposure of the first active agent; thereby they allow increased concentration of the first active agent, e.g., a compound of Formula I or II, in the solution and increased frequency of delivery, thus, promoting maintained high concentration of the first active agent in the posterior segment of the eye.

The solutions of the application comprise about 0.005% to about 5.0% w/v of the first active agent of Formula I or II, or a pharmaceutically acceptable salt thereof, for example, Compound-I. In some embodiments, the concentration of Compound-I or its free base (Formula II) in the solutions is about 0.005%-about 0.01%, about 0.01%-about 0.05%, about 0.05%-about 0.1%, about 0.1%-about 0.2%, about 0.2%-about 0.3%, about 0.3%-about 0.4%, about 0.4%-about 0.5%, about 0.5%-about 0.6%, about 0.6%-about 0.7%, about 0.7%-about 0.8%, about 0.8%-about 0.9%, about 0.9%-about 1.0%, about 1.0-about 2.0%, about 2.0-about 3.0%, about 3.0-about 4.0%, or about 4.0-about 5.0% w/v for topical administration. In some embodiments, the concentration of Compound-I or its free base (Formula II) in the formulations is about 0.1%-about 1.2%, about 0.2%-about 1.2%, about 0.3%-about 1.2%, about 0.4%-about 1.2%, 0.1%-about 1.1%, about 0.2%-about 1.1%, about 0.3%-about 1.1%, about 0.4%-about 1.1%, 0.1%-about 1.0%, about 0.2%-about 1.0%, about 0.3%-about 1.0%, about 0.4%-about 1.0%, 0.1%-about 0.8%, about 0.2%-about 0.8%, about 0.3%-about 0.8%, about 0.4%-about 0.8%, 0.1%-about 0.6%, about 0.2%-about 0.6%, about 0.3%-about 0.6%, about 0.4%-about 0.6%, 0.1%-about 0.5%, about 0.2%-about 0.5%, about 0.3%-about 0.5%, about 0.4%-about 0.5%, 0.1%-about 0.4%, about 0.2%-about 0.4%, about 0.3%-about 0.4% w/v for topical administration. In some embodiments, the solutions include about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of Compound-I or its free base (Formula II).

The solutions of the application may further comprise about 0.00001%-about 5.0% w/v of a second active agent, or a pharmaceutically acceptable salt thereof, for example, nicotinic acid, nicotinamide, or vitamin K, or a combination thereof. The solutions of the application may further comprise is about 0.00001%-about 1.0%, about 0.00001%-about 0.1%, about 0.00001%-about 0.01%, about 0.00001%-about 0.001%, about 0.00001%-about 0.0002%, or about 0.00001%-about 0.0001% w/v of a second active agent, or a pharmaceutically acceptable salt thereof, for example, nicotinic acid, nicotinamide, or vitamin K, or a combination thereof. In some embodiments, the concentration of the second active agent in the solutions is about 0.00001%-about 0.0001%, 0.000012%-about 0.0001%, 0.000014%-about 0.0001%, 0.000016%-about 0.0001%, 0.000018%-about 0.0001%, 0.00002%-about 0.0001%, 0.00003%-about 0.0001%, 0.00004%-about 0.0001%, 0.00005%-about 0.0001%, 0.00006%-about 0.0001%, 0.00007%-about 0.0001%, 0.00008%-about 0.0001%, 0.00009%-about 0.0001%, 0.000016%-about 0.00009%, 0.000018%-about 0.00009%, 0.00002%-about 0.00009%, 0.00003%-about 0.00009%, 0.00004%-about 0.00009%, 0.00005%-about 0.00009%, 0.00006%-about 0.00009%, 0.00007%-about 0.00009%, 0.00008%-about 0.00009% w/v for topical administration. In some embodiments, the solutions include about 0.00001%, 0.00002%, 0.00003%, 0.00004%, 0.00005%, 0.00006%, 0.00007%, 0.00008%, 0.000081%, 0.000082%, 0.000083%, 0.000084%, 0.000085%, 0.000086%, 0.000087%, 0.000088%, or 0.000089% w/v of the second active agent.

The solutions of the application may further comprise about 0.5 µM, about 0.6 µM, about 0.7 µM, about 0.8 µM, about 0.9 µM, about 1 µM, about 2 µM, about 3 µM, about 4 µM, about 5 µM, about 6 µM, about 7 µM, about 8 µM, or about 9 µM of a second active agent, or a pharmaceutically acceptable salt thereof, for example, nicotinic acid, nicotinamide, or vitamin K, or a combination thereof. In some embodiments, the concentration of the second active agent is about 1 µM.

In some embodiments, the formulation comprises cyclodextrin for improving solubility of a first active agent (e.g., Compound-I). Cyclodextrin, an oligosaccharide made up of six to eight dextrose units joined through one or four bonds increases solubility of active agents that have poor or low solubility in water or aqueous solutions (e.g., in PBS buffer). Cyclodextrins form hydrophilic complexes with hydrophobic active agents.

One or more cyclodextrins may be used in the solution of the present application. Non-limiting examples of cyclodextrins for use in formulation of the present application are, for example: 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or a combination thereof.

In some embodiments, the solution of Formula II compound or Compound-I comprising cyclodextrin is a clear and colorless solution and has a viscosity similar to water. In some embodiments, the present application provides a solution comprising Compound-I, one or more cyclodextrin, and a second active agent for topical application and is topically applied to the eye.

The ophthalmic solution of the present application comprises cyclodextrin and pharmaceutical excipients chosen at or below concentrations optimal for ophthalmic solution. The excipients of the present application are, for example, benzalkonium chloride (BAK) and NaCl. In some embodiments, the ophthalmic solution comprises about 0.001-about 0.005% w/v Benzalkonium chloride (BAK). The BAK amount varies depending on the need of the application.

The ophthalmic solution comprises, for example, without being limiting, about 0.005%-5.0% Compound-I or its free base, about 2-about 25% cyclodextrin, e.g., without being limiting, Hydroxypropyl-β-cyclodextrin (HPβCD) or methylcyclodextrin (KLEPTOSE® HPB), and/or sulfobutyl ether-β-cyclodextrin (CAPTISOL®), about 0.1-about 0.7% salt, e.g., without being limiting, NaCl, and/or about 0.005% of an anti-microbial agent, for example, without being limiting, Benzalkonium chloride (BAK). The formulation comprises Compound-I or its free base to cyclodextrin ratio 1:2, 1:3, 1:4, 1:5, 1:6, 1:7, 1:8, 1:9, 1:10, or between 1:10 and 1:20. In some embodiments, the ophthalmic solution comprising cyclodextrin further comprises tromethamine (also known as Tris, Tris(Hydroxymethyl)aminomethane, or Tris buffer). In some embodiments, the ophthalmic solution comprises about 0.05%-1% Tris. In some embodiments, the ophthalmic solution comprises about 0.05%-0.5% Tris. In some embodiments, the ophthalmic solution comprises about 0.05%-0.2% Tris. In some embodiments, the ophthalmic solution comprises about 0.1%-0.15% Tris. In some embodiments, the ophthalmic solution comprises about 1% Tris. In some embodiments, the ophthalmic solution further comprises about 0.005%-5.0% second active agent.

Ophthalmic solutions of the present embodiments include, for example, without being limiting: about 0.3%-about 5.0% Compound-I (about 3 mg/mL-about 50.0 mg/mL), about 0.05% sodium phosphate monobasic monohydrate, about 2% glycerin; about 0.4% Compound-I, about 7% HPβCD, about 0.7% NaCl, about 0.005% BAK; about 0.4% Compound-I, about 4% HPβCD, about 0.7% NaCl, about 0.005% BAK; about 0.4% Compound-I, about 7% HPβCD, about 1% tromethamine, about 0.4% NaCl, about 0.005% BAK; and about 0.6% Compound-I, about 7% HPβCD, about 0.7% NaCl, about 0.005% BAK. For Compound-I of between about 0.005% to about 5.0% concentrations, cyclodextrin is present at a corresponding molar ratio. In some embodiments, the ophthalmic solution further comprises about 0.005%-5.0% second active agent.

Additional ophthalmic solutions include, for example, without being limiting: about 0.4% Formula II compound (free base), about 7.15% HPβCD, about 0.7% NaCl; about 0.1% Formula II compound (free base), about 1.79% HPβCD, about 0.85% NaCl; about 0.2% Formula II compound (free base), about 3.57% HPβCD, about 0.8% NaCl; about 0.6% Formula II compound (free base), about 10.72% HPβCD, about 0.6% NaCl; about 0.4% Formula II compound (free base), about 8.41% HPβCD, about 0.65% NaCl; about 0.4% Compound-I, about 10.51 HPβCD, about 0.65% NaCl; about 0.4% Formula II compound (free base), about 10.51% HPβCD, about 0.15% NaCl, about 1.0% tromethamine (Tris); and/or about 0.1% Formula II compound (free base), about 20.63% HPβCD, about 0.8% NaCl; about 0.6% Compound-I (as free base), about 15.77% HPβCD, about 0.37% NaCl. For Formula II of between about 0.005% to about 5.0% concentrations, cyclodextrin is present at a corresponding molar ratio. In some embodiments, the ophthalmic solution further comprises about 0.005%-5.0% second active agent.

In some embodiments, the ophthalmic solutions include between about 1.0%-about 25% cyclodextrin. For example, without being limiting, the Compound-I formulations include about 2.0%-about 3.0% HPβCD, about 3.0%-about 5.0% HPβCD, about 5.0%-about 10% HPβCD, or about 10%-about 25% HPβCD. In some embodiments, the ophthalmic solution further comprises about 0.005%-5.0% second active agent.

In additional embodiments, the ophthalmic solutions are formulated as, for example, without being limiting: about 8.41% KLEPTOSE® HPB and about 0.142% phosphate; about 8.9% KLEPTOSE® HPB and about 0.142% phosphate; about 4.88% CAPTISOL® and about 0.142 phosphate; and/or about 4.88% CAPTISOL® and about 0.122% phosphate.

In some embodiments, the ophthalmic solutions comprising cyclodextrins are clear and colorless, and are extremely viscous, moderately viscous, or have viscosity similar to water.

In some embodiments, the ophthalmic solution of the application has a pH value of about 4.5 to about 7.5 at or under about 40° C.

In some embodiments, the ophthalmic solution of the application has a pH value of about 5.0 to about 7.0 at or under about 40° C.

For example, the ophthalmic solution of the application has a pH value of about 6.0 at or under about 40° C.

The ophthalmic solutions of the present application may contain various additives incorporated ordinarily, such as buffering agents (e.g., phosphate buffers, borate buffers, citrate buffers, tartrate buffers, acetate buffers, amino acids, sodium acetate, sodium citrate and the like), tonicity agents (e.g., saccharides such as sorbitol, glucose and mannitol, polyhydric alcohols such as glycerin, concentrated glycerin, PEG and Propylene glycol, salts such as sodium chloride, etc.), preservatives or antiseptics (e.g., Benzalkonium chloride, Benzatkonium chloride, P-oxybenzoates such as Methyl p-oxybenzoate or Ethyl p-oxybenzoate, Benzyl alcohol, Phenethyl alcohol, Sorbic acid or its salt, Thimerosal, Chlorobutanol, etc.), solubilizing aids or particle stabilizing agents (e.g., water-soluble polymers such as polyvinyl pyrrolidone, surfactants such as tyloxapol, polysorbates, poloxamer, etc.), pH modifiers (e.g., Hydrochloric acid, Acetic acid, Phosphoric acid, Sodium hydroxide, Potassium hydroxide, Ammonium hydroxide and the like), thickening agents (e.g., HEC, Hydroxypropyl cellulose, Methyl cellulose, HPMC, Carboxymethyl cellulose and their salts), chelating agents (e.g., sodium edetate, sodium citrate, condensed sodium phosphate etc.), and second active agent stabilizers (e.g., EDTA, propyl gallate, and a combination thereof).

The ophthalmic solutions of the present application comprise cyclodextrin, and may further comprise additional excipients, for example, without being limiting, about 0.5%-about 3% surfactant and emulsifier, for example, without being limiting, polysorbate 80 or equivalent excipients thereof; about 0.05-about 0.4% nonionic liquid polymer of the alkyl aryl polyether alcohol type, for example, without being limiting tyloxapol; and/or about 0.05%-about 0.6% hydrophilic non-ionic surfactant, for example, without being limiting, poloxamer, such as poloxamer 407.

In some embodiments, the ophthalmic solution comprises about 0.01-about 0.5%, about 0.02-about 0.5%, about 0.04-about 0.5%, about 0.06-about 0.5%, about 0.08-about 0.5%, about 0.08-about 0.4%, about 0.08-about 0.3%, about 0.08-about 0.2%, about 0.08-about 0.18%, about 0.08-about 0.16%, about 0.08-about 0.14%, or about 0.08-about 0.12% EDTA. In some embodiments, the ophthalmic solution comprises about 0.04%, about 0.06%, about 0.08%, about 0.1%, about 0.12, about 0.14%, about 0.16%, about 0.18%, or about 0.2% EDTA. In some embodiments, the ophthalmic solution comprises about 0.1% EDTA.

In some embodiments, the ophthalmic solution comprises about 0.001-about 0.5%, about 0.002-about 0.5%, about 0.005-about 0.5%, about 0.01-about 0.5%, about 0.02-about 0.5%, about 0.03-about 0.5%, about 0.04-about 0.5%, about 0.01-about 0.4%, about 0.01-about 0.3%, about 0.01-about 0.2%, about 0.01-about 0.1%, about 0.01-about 0.08%, about 0.01-about 0.06% propyl gallate. In some embodiments, the ophthalmic solution comprises about 0.01%, about 0.02%, about 0.03%, about 0.04%, about 0.05%, about 0.06%, about 0.07%, about 0.08%, about 0.09% propyl gallate. In some embodiments, the ophthalmic solution comprises about 0.05% propyl gallate.

Concentration in Various Ocular Tissues—Delivered as an Ophthalmic Solution

The ocular solution comprising cyclodextrin improves bioavailability of the first active agents of the present application at the posterior segment of the eye. Without being bound by theory, in an embodiment, the formulation comprising cyclodextrin forms a clear and colorless solution, which lowers corneal exposure of the active agent, for example, exposure of Compound-I, by about 5-15 fold compared to the corneal exposure to with an equimolar Gel Drop formulation.

Without being bound by theory, in one embodiment, an ophthalmic solution comprising cyclodextrin increases the therapeutic index of Compound-I during topical ocular administration. Upon administration, the hydrophilic complex of cyclodextrin-Compound-I is pharmacologically inert at the cornea. Without being bound by theory, in some embodiments, the cyclodextrin-Compound-I complex increases corneal tolerability of Compound-I. Without being bound by theory, in some embodiments, spontaneous dissociation of cyclodextrin from Compound-I at the peripheral vasculature increases bioavailability at the target tissue, e.g., at the choroid or retina.

Unlike other formulations of Compound-I, which in some embodiments contribute to corneal toxicity, the cyclodextrin-based ophthalmic solution comprising similar concentration of Compound-I lower corneal exposures and, thereby increase the therapeutic index and corresponding benefits to patients. In one embodiment, the use of cyclodextrin-based solution of Compound-I provides approximately 10× reduction in corneal exposure, as compared to equimolar concentrations of Gel Drop. In some embodiments, the cyclodextrin-based solution of Compound-I reduces corneal exposure of Compound-I by 5×, 20×, 30×, 40×, or 50×. In one embodiment, 1-90 days or 3-9 months of topical ocular dosing of about 0.005%-about 5.0% Compound-I as a cyclodextrin-based solution does not have any adverse or toxic effect at the cornea, choroid, and/or the retina. In yet another embodiment, 1-90 days of topical ocular dosing of about 0.6%-about 5.0% Compound-I as a cyclodextrin-based solution does not have any adverse or toxic effect at the cornea, choroid, and/or the retina.

The lowering of the corneal exposure is correlated with increasing bioavailability and therapeutic index of the active agent at the posterior segment, for example, at the retina or choroid, of the eye. For example, no toxic effect attributable to the first active agent or a suitable carrier is observed to the cornea or other parts of the eye when about 0.1%-about 5.0% Compound-I formulation comprising cyclodextrin is administered topically administered to the eye for at least 30 days or more than 60 days.

In one embodiment, when a formulation comprising about 0.4% (about 4 mg/mL) of Compound-I or its free base, and cyclodextrin, when administered topically to the eye, the central choroid concentration is between about 0.2 $\mu$M-about 0.9 $\mu$M, central retina concentration of the active agent is between about 0.02 $\mu$M-about 0.4 $\mu$M, aqueous humor concentration of the active agent is about 0.003 $\mu$M-about 0.009 $\mu$M, and corneal concentration of the active agent is between 6 $\mu$M-40 $\mu$M. The cyclodextrin used in the formulation is, for example, without being limiting example, KLEPTOSE® HPB or CAPTISOL®.

In some embodiments, a cyclodextrin-based solution of Compound-I or its free base increases the bioavailability of the active agent at the central choroid and the central retina, while reducing concentration at the cornea. In some embodiments, topical delivery of Compound-I or its free base formulated in the presence of cyclodextrin reduces the corneal concentration by about 5-about 15 fold over the corneal concentration of equimolar Gel Drop.

Without being bound by theory, in some embodiments, the combined effects of decreasing corneal drug exposure so as to avoid poor ocular tolerability while increasing posterior segment bioavailability increase the therapeutic index and corresponding benefits to patients.

In some embodiments, the exposure time of Compound-I and the second active agent is between 1 and 90 days or for longer than 90 days (e.g., 4 months, 6 months, 8 months, or 12 months). In some embodiments, the dosage regimen involves several courses of topical ocular administration of a formulation comprising Compound-I and a second active agent, wherein the second active agent is administered as a separate formulation or as part of the Compound-I formulation, to a subject for between 1 and 90 days or for longer than 90 days (e.g., 4 months, 6 months, 8 months, or 12 months). For example, the dosage regimen involves once daily, twice daily, three times daily or four times daily administration of the formulation for between 1 and 90 days or for longer than 90 days (e.g., 4 months, 6 months, 8 months, or 12 months). For example, the dosage regimen involves once, twice, three times, or four times administration of a compound of Formula I or II and a second active agent on alternate days (i.e., on day 1, 3, 5, 7 etc.) for up to 90 days. For example, the dosage regimen involves administering once on day 1, once or twice on day 2-day 90. For example, the dosage regimen involves administering once, twice, three times, or four times on day 1, followed by once daily for 2-90 days. For example, the dosage regimen involves administering once, twice, three times, four times on day 1, followed by once, twice, three times, or four times on alternate days (i.e., on day 1, 3, 5, 7 etc.) for up to 90 days. For example, one dosage regimen involves once per day or twice per day for 1, 2, 3, 4, or 5 consecutive days. For twice or three daily dosage regimen, subjects receive topical ocular dose of a Compound-I formulation and a second active agent on days 1 and 4 approximately about 4, 6, or 8 hours apart. In another embodiment, subjects receive topical ocular doses of a Compound-I formulation and a second active agent approximately about 4, 6, or 8 hours apart for four consecutive days. In some embodiments, subjects receive one or two doses of topical ocular dose of Compound-I formulation and a second active agent per day for 5 consecutive days. In yet other embodiments, subjects receive one or two doses of topical ocular dose of Compound-I and a second active agent formulation for 5-90 consecutive days. In some embodiments, subjects receive one or two doses of topical ocular dose of Compound-I formulation and a second active agent for at least 25 consecutive days. In one embodiment, subjects receive one or two topical ocular doses for at least 90 consecutive days or more. The second active agent can be administered separately or as part of the Compound-I formulation. When administered separately, the second active agent, or a pharmaceutical salt thereof, can be administered alone or as a formulation.

For example, a formulation comprising about 1 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 1 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 1 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 1 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 2 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 2 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 2 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 2 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 3 mg/mL BID of a first active agent (e.g., Compound-I) and/or a second active agent is administered to one eye or both eyes of a subject for between 1 and 90 days or for longer than 90 days (e.g., 4 months, 6 months, 8 months, or 12 months). In some embodiments a formulation comprising about 3 mg/mL QD of a first active agent (e.g., Compound-I) and/or a second active agent is administered to one eye or both eyes of a subject for between 1 and 90 days or for longer than 90 days (e.g., 4 months, 6 months, 8 months, or 12 months). In some embodiments a formulation comprising about 3 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 3 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 4 mg/mL BID of a first active agent (e.g., Compound-I) and/or a second active agent is administered to one eye or both eyes of a subject for between 1 and 90 days or for longer than 90 days (e.g., 4 months, 6 months, 8 months, or 12 months). In some embodiments a formulation comprising about 4 mg/mL QD of a first active agent (e.g., Compound-I) and/or a second active agent is administered to one eye or both eyes of a subject for between 1 and 90 days or for longer than 90 days (e.g., 4 months, 6 months, 8 months, or 12 months). In some embodiments a formulation comprising about 4 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 4 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 5 mg/mL BID of a first active agent (e.g., Compound-I) and/or a second active agent is administered to one eye or both eyes of a subject for between 1 and 90 days or for longer than 90 days (e.g., 4 months, 6 months, 8 months, or 12 months). In some embodiments a formulation comprising about 5 mg/mL QD of a first active agent (e.g., Compound-I) and/or a second active agent is administered to one eye or both eyes of a subject for between 1 and 90 days or for longer than 90 days (e.g., 4 months, 6 months, 8 months, or 12 months). In some embodiments a formulation comprising about 5 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 5 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 6 mg/mL BID of a first active agent (e.g., Compound-I) and/or a second active agent is administered to one eye or both eyes of a subject for between 1 and 90 days or for longer than 90 days (e.g., 4 months, 6 months, 8 months, or 12 months). In some embodiments a formulation comprising about 6 mg/mL QD of a first active agent (e.g., Compound-I) and/or a second active agent is administered to one eye or both eyes of a subject for between 1 and 90 days or for longer than 90 days (e.g., 4 months, 6 months, 8 months, or 12 months). In some embodiments a formulation comprising about 6 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 6 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 7 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 7 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 7 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 7 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 8 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 8 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 8 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 8 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 9 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 9 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 9 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 9 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 10 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). The dosage regimen for between 1 and 90 days or for longer than 90 days (e.g., 4 months, 6 months, 8 months, or 12 months) may be any of the regimens involving consecutive or alternate days described in the paragraph above. In some embodiments, the formulation of the present application is administered QD, BID, TID, or QID when administered at low doses (e.g., 1 mg/mL, 2 mg/mL, 3 mg/mL, 4 mg/mL, or 5 mg/mL), and QD or BID at high doses (e.g., 6 mg/mL, 7 mg/mL, 8 mg/mL, 9 mg/mL, or 10 mg/mL).

In some embodiments, a 1 mg/mL BID of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 1 mg/mL QD of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 2 mg/mL BID of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 2 mg/mL QD of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 3 mg/mL BID of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 3 mg/mL QD of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 4 mg/mL BID of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 4 mg/mL QD of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 5 mg/mL BID of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 5 mg/mL QD of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 6 mg/mL BID of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 6 mg/mL QD of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 7 mg/mL BID of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 7 mg/mL QD of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 8 mg/mL BID of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 8 mg/mL QD of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 9 mg/mL BID of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 9 mg/mL QD of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 10 mg/mL BID of a first active agent (e.g., Compound-I) formulation and a second active agent is administered to one eye or both eyes of a subject for between 1 and 90 days or for longer than 90 days (e.g., 4 months, 6 months, 8 months, or 12 months). In some embodiments, a 10 mg/mL QD of a first active agent (e.g., Compound-I) formulation and a second active agent is administered to one eye or both eyes of a subject for between 1 and 90 days or for longer than 90 days (e.g., 4 months, 6 months, 8 months, or 12 months). The dosage regimen for between 1 and 90 days or for longer than 90 days (e.g., 4 months, 6 months, 8 months, or 12 months) may be any of the regimens involving consecutive or alternate days described in the paragraph above.

The present application provides cyclodextrin-based solutions containing hydroxypropyl-beta-cyclodextrin (HP-β-CD, KLEPTOSE® HPB) or CAPTISOL® that are well tolerated when administered topically for 30-90 days or for 4-6 months. In some embodiments, once or twice daily administration of at about 0.005%-about 5.0% w/v Compound-I or its free base and a second active agent in a solution containing about 1.0%-about 25% HP-β-CD or CAPTISOL® is well tolerated by the subject.

In some embodiments, the formulation of Formula II or Compound-I and a second active agent is administered to one eye or both eyes of a subject. For example, about 0.2%-about 1.0% (w/v) of the compound of Formula II or about 0.1%-1.2% (w/v) of Compound-I formulation and a second active agent comprising formulation of the present application is administered once a day (QD), twice a day (BID), three times a day (BID), or four times a day (QID) to one eye or both eyes of a subject for between 1 and 90 days or for longer than 90 days (e.g., 4 months, 6 months, 8 months, or 12 months). In some embodiments, the Formula II or Compound-I formulation and a second active agent are administered to one eye or both eyes of a subject. For example, about 0.2%-about 1.0% (w/v) of the compound of Formula II or about 0.1%-1.2% (w/v) of Compound-I formulation and a second active agent is administered once a day (QD), twice a day (BID), three times a day (BID), or four times a day (QID) to one eye or both eyes of a subject for between 1 and 90 days or for longer than 90 days (e.g., 4 months, 6 months, 8 months, or 12 months).

In some embodiments, Formula II compound or Compound-I is complexed with a complexing agent, e.g., cyclodextrin (e.g., KLEPTOSE® HPB (%)) in ratio of about 1:8, in which about 2%-13% (w/v) cyclodextrin (e.g., KLEPTOSE® HPB (%)) is added to the formulation. The formulation may further comprise about 0.1%-about 0.2% buffer, e.g., 10 mM phosphate buffer. The desired osmolality of the formulation is about 200-about 300 mOsm, achieved by adding quantity sufficient to achieve the osmolality with a salt, e.g., sodium chloride. The pH of the formulation is about 6.0 at or under about 40° C. The dosage regimen for between 1 and 90 days or for longer than 90 days (e.g., 4 months, 6 months, 8 months, or 12 months) may be any of the regimens involving consecutive or alternate days described in the paragraph above.

Ophthalmic Suspensions

The present application provides suspensions of a first active agent (e.g., Compound-I) comprising the agent and pharmaceutically acceptable excipients. The present application also provides suspensions of a first active agent (e.g., Compound-I) and a second active agent comprising the first active agent, the second active agent and pharmaceutically acceptable excipients. For example, Compound-I suspensions and second active agent suspensions may include, without being limiting, buffering agents, acids & bases, for example, without being limiting, HCl and NaOH. In one embodiment, suspensions of Compound-I or its free base may include a buffering agent, for example, without being limiting, tromethamine (Tris). In another embodiment, suspensions of Compound-I or its free base and a second active agent may include a buffering agent, for example, without being limiting, tromethamine (Tris). The tromethamine-based suspension of Formula II compound or Compound-I and a second active agent is useful for topical administration to the eye.

The suspensions of the application comprise about 0.005% to about 5.0% w/v of a first active agent of Formula I or II, or a pharmaceutically acceptable salt thereof, for example, Compound-I. In some embodiments, the concentration of Compound-I or its free base (Formula II) in the suspensions is about 0.005%-about 0.01%, about 0.01%-about 0.05%, about 0.05%-about 0.1%, about 0.1%-about 0.2%, about 0.2%-about 0.3%, about 0.3%-about 0.4%, about 0.4%-about 0.5%, about 0.5%-about 0.6%, about 0.6%-about 0.7%, about 0.7%-about 0.8%, about 0.8%-about 0.9%, about 0.9%-about 1.0%, about 1.0-about 2.0%, about 2.0-about 3.0%, about 3.0-about 4.0%, or about 4.0-about 5.0% w/v for topical administration. In some embodiments, the concentration of Compound-I or its free base (Formula II) in the formulations is about 0.1%-about 1.2%, about 0.2%-about 1.2%, about 0.3%-about 1.2%, about 0.4%-about 1.2%, 0.1%-about 1.1%, about 0.2%-about 1.1%, about 0.3%-about 1.1%, about 0.4%-about 1.1%, 0.1%-about 1.0%, about 0.2%-about 1.0%, about 0.3%-about 1.0%, about 0.4%-about 1.0%, 0.1%-about 0.8%, about 0.2%-about 0.8%, about 0.3%-about 0.8%, about 0.4%-about 0.8%, 0.1%-about 0.6%, about 0.2%-about 0.6%, about 0.3%-about 0.6%, about 0.4%-about 0.6%, 0.1%-about 0.5%, about 0.2%-about 0.5%, about 0.3%-about 0.5%, about 0.4%-about 0.5%, 0.1%-about 0.4%, about 0.2%-about 0.4%, about 0.3%-about 0.4% w/v for topical administration. In some embodiments, the suspensions include about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of Compound-I or its free base (Formula II).

The suspensions of the application may further comprise about 0.00001%-about 5.0% w/v of a second active agent, or a pharmaceutically acceptable salt thereof, for example, nicotinic acid, nicotinamide, or vitamin K, or a combination thereof. The suspensions of the application may further comprise about 0.00001%-about 1.0%, about 0.00001%-about 0.1%, about 0.00001%-about 0.01%, about 0.00001%-about 0.001%, about 0.00001%-about 0.0002%, or about 0.00001%-about 0.0001% w/v of a second active agent, or a pharmaceutically acceptable salt thereof, for example, nicotinic acid, nicotinamide, or vitamin K, or a combination thereof. In some embodiments, the concentration of the second active agent in the suspensions is about 0.00001%-about 0.0001%, 0.000012%-about 0.0001%, 0.000014%-about 0.0001%, 0.000016%-about 0.0001%, 0.000018%-about 0.0001%, 0.00002%-about 0.0001%, 0.00003%-about 0.0001%, 0.00004%-about 0.0001%, 0.00005%-about 0.0001%, 0.00006%-about 0.0001%, 0.00007%-about 0.0001%, 0.00008%-about 0.0001%, 0.00009%-about 0.0001%, 0.000016%-about 0.00009%, 0.000018%-about 0.00009%, 0.00002%-about 0.00009%, 0.00003%-about 0.00009%, 0.00004%-about 0.00009%, 0.00005%-about 0.00009%, 0.00006%-about 0.00009%, 0.00007%-about 0.00009%, or 0.00008%-about 0.00009% w/v for topical administration. In some embodiments, the suspensions include about 0.00001%, 0.00002%, 0.00003%, 0.00004%, 0.00005%, 0.00006%, 0.00007%, 0.00008%, 0.000081%, 0.000082%, 0.000083%, 0.000084%, 0.000085%, 0.000086%, 0.000087%, 0.000088%, or 0.000089% w/v of the second active agent.

The suspensions of the application may further comprise about 0.5 µM, about 0.6 µM, about 0.7 µM, about 0.8 µM, about 0.9 µM, about 1 µM, about 2 µM, about 3 µM, about 4 µM, about 5 µM, about 6 µM, about 7 µM, about 8 µM, or about 9 µM of a second active agent, or a pharmaceutically acceptable salt thereof, for example, nicotinic acid, nicotinamide, or vitamin K, or a combination thereof. In some embodiments, the concentration of the second active agent is about 1 µM.

The ophthalmic suspensions may contain various additives incorporated ordinarily, such as buffering agents (e.g., phosphate buffers, borate buffers, citrate buffers, tartrate buffers, acetate buffers, amino acids, sodium acetate, sodium citrate and the like), tonicity agents (e.g., saccharides such as sorbitol, glucose and mannitol, polyhydric alcohols such as glycerin, concentrated glycerin, PEG and propylene glycol, salts such as sodium chloride), preservatives or antiseptics (e.g., benzalkonium chloride, benzatkonium chloride, P-oxybenzoates such as methyl p-oxybenzoate or ethyl p-oxybenzoate, Benzyl alcohol, phenethyl alcohol, Sorbic acid or its salt, Thimerosal, Chlorobutanol and the like), solubilizing aids or particle stabilizing agents (e.g., cyclodextrins and their derivative, water-soluble polymers such as polyvinyl pyrrolidone, surfactants such as tyloxapol, polysorbates, poloxamer), pH modifiers (e.g., hydrochloric acid, acetic acid, phosphoric acid, sodium hydroxide, potassium hydroxide, ammonium hydroxide and the like), thickening agents (e.g., HEC, hydroxypropyl cellulose, methyl cellulose, HPMC, carboxymethyl cellulose and their salts), chelating agents (e.g., sodium edetate, sodium citrate, condensed sodium phosphate etc.), and second active agent stabilizers (e.g., EDTA, propyl gallate, and a combination thereof).

The ophthalmic suspension of the present application comprises pharmaceutical excipients chosen at or below concentrations optimal for ophthalmic solution. The excipients of the present application include, for example, without being limiting, sodium phosphate monohydrate, glycerin, and benzalkonium chloride (BAK).

In some embodiments, the ophthalmic suspension comprises about 0.01-about 0.5%, about 0.02-about 0.5%, about 0.04-about 0.5%, about 0.06-about 0.5%, about 0.08-about 0.5%, about 0.08-about 0.4%, about 0.08-about 0.3%, about 0.08-about 0.2%, about 0.08-about 0.18%, about 0.08-about 0.16%, about 0.08-about 0.14%, or about 0.08-about 0.12% EDTA. In some embodiments, the ophthalmic suspension comprises about 0.04%, about 0.06%, about 0.08%, about 0.1%, about 0.12, about 0.14%, about 0.16%, about 0.18%, or about 0.2% EDTA. In some embodiments, the ophthalmic suspension comprises about 0.1% EDTA.

In some embodiments, the ophthalmic suspension comprises about 0.001-about 0.5%, about 0.002-about 0.5%, about 0.005-about 0.5%, about 0.01-about 0.5%, about 0.02-about 0.5%, about 0.03-about 0.5%, about 0.04-about 0.5%, about 0.01-about 0.4%, about 0.01-about 0.3%, about 0.01-about 0.2%, about 0.01-about 0.1%, about 0.01-about 0.08%, about 0.01-about 0.06% propyl gallate. In some embodiments, the ophthalmic suspension comprises about 0.01%, about 0.02%, about 0.03%, about 0.04%, about 0.05%, about 0.06%, about 0.07%, about 0.08%, about 0.09% propyl gallate. In some embodiments, the ophthalmic suspension comprises about 0.05% propyl gallate.

In some embodiments, the ophthalmic suspension comprises about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of Formula I or II, or a pharmaceutically acceptable salt thereof, for example, Compound-I, and a second active agent, and may further comprise tromethamine (i.e., Tris). In some embodiments, the ophthalmic suspension comprises about 0.05%-1% Tris. In some embodiments, the ophthalmic suspension comprises about 0.2%-1.0% Tris. In some embodiments, the ophthalmic suspension comprises about 0.4%-0.8% Tris. The tromethamine-based suspension of Compound-I or its free base and/or a second active agent may comprise additional buffers and excipients, for example, without being limiting, phosphate buffer. The suspensions may further comprise one or more surfactant and emulsifier, for example, without being limiting, polysorbate 80 or equivalent excipients thereof; one or more nonionic liquid polymer of the alkyl aryl polyether alcohol type, for example, without being limiting tyloxapol; and/or one or more hydrophilic non-ionic surfactant, for example, without being limiting, poloxamer, such as poloxamer 407.

The present application provides suspensions of the agents of the present application formulated in the presence of excipients such as, without being limiting, Povidone, polysorbate 80 (PS80), polyethylene glycol (PEG) 400, tyloxapol, poloxamer, glycerin, and BAK in a Tris buffer.

In one embodiment the suspension of Compound-I or its free base comprises about 0.1-0.5% phosphate buffer. In another embodiment the suspension of Compound-I or its free base and the second active agent comprises about 0.1-0.5% phosphate buffer. In some embodiments, the pH of the tromethamine-based suspension is between pH 4-7, for example, pH 6.0. In some embodiments, the suspensions prepared in Tris further comprise about 0.5%-about 2% polysorbate 80; about 0.05-about 0.2% tyloxapol; and/or about 0.05%-about 0.4% poloxamer 407.

In some such embodiments, the suspensions of the application further comprise about 0.01-about 1%, or about 1-about 2.0% w/v glycerin. In a specific embodiment, the suspensions comprise about 2% w/v glycerin.

In some embodiments, the suspensions of the application further comprise about 0.001-about 0.005% w/v Benzalkonium chloride (BAK). The BAK amount may be varied depending on any observed adverse effects. BAK may be damaging to the cells on the ocular surface, and, therefore, the amount in the formulation may be varied to achieve an optimal level of ocular penetration of Compound-I, without compromising the ocular cell layer integrity and increased toxicity.

In some embodiments, the suspension optionally comprises buffers. Buffers when used, for example, can be sodium monophosphate basic, phosphoric acid and Tris buffer. Compound-I concentration in suspension is about 0.005%-about 5.0% w/v. The suspension prepared without additional buffer further comprises about 0.005% BAK and about 2% glycerin and with a pH 6.0. In another embodiment the suspension prepared without additional buffer comprises about 1% polysorbate 80, about 0.1% tyloxapol, about 0.2% Poloxamer 407, about 0.005% BAK, about 2.0% glycerin, and with a pH 6.0.

In suspensions prepared in phosphoric acid/Tris, the suspension comprises about 0.14% phosphoric acid, about 0.2% Tris base, about 1.0% polysorbate 80, about 0.005% BAK, about 2.0% glycerin and with a pH 6.0. In one embodiment, the suspension further comprises about 0.2% tyloxapol. The pH of the suspension varies between about pH 6.0 and 7.2.

The suspensions prepared in tromethamine (Tris) alone comprise about 1% polysorbate 80, about 0.1% tyloxapol, about 0.2% Poloxamer 407, about 0.6% Tris, about 0.005% BAK, and about 2.0% glycerin with pH 6.0. In another embodiment, a suspension prepared in Tris comprises, about 1% Tris, about 0.45% NaCl, about 0.025% EDTA, about 0.2% HPMC, about 0.1% polysorbate 80, about 0.005% BAK, with a pH 6.0. In these suspensions 1 N HCl and/or 1N NaOH are used for titration to appropriate pH.

The suspension of the application comprises about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% of an active agent of Formula I or II, or a pharmaceutically acceptable salt thereof, for example, Compound-I, and about 0.01%-about 0.05%, about 0.05-about 0.09%, or about 0.09-about 0.2% w/v sodium phosphate monobasic monohydrate and/or about 0.3%-about 1.0% of Tris. Alternatively, the suspension of the application comprises about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% of an active agent of Formula I or II, or a pharmaceutically acceptable salt thereof, for example, Compound-I, about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% of a second active agent, and about 0.01%-about 0.05%, about 0.05-about 0.09%, or about 0.09-about 0.2% w/v sodium phosphate monobasic monohydrate and/or about 0.3%-about 1.0% of Tris.

In a specific embodiment, the suspension comprises about 0.14% or about 0.2% w/v Tris-buffer. In additional embodiments, suspensions are prepared in about 0.6% Tris or about 1.0% Tris. Other equivalent buffer systems well known in the art are also used in the suspensions of the present application. In one embodiment, the Formula II compound or Compound-I is formulated as about 0.4% active agent, about 5% Cremophor RH40, about 2.0% glycerin, and about 0.005% BAK. In another embodiment, the Formula II compound or Compound-I is formulated as about 0.4% active agent, about 0.005% to about 5.0% of the second active agent, about 5% Cremophor RH40, about 2.0% glycerin, and about 0.005% BAK.

In some embodiments, the suspension of the application has a pH value of about 4.0 to about 7.5 at or under about 40° C.

In some embodiments, the suspension of the application has a pH value of about 5.0 to about 7.0 at or under about 40° C.

For example, the suspension of the application has a pH value of about 6.0 at or under about 40° C.

In some embodiments, the first active agent may be formulated as a solution according to the embodiments described herein, and the second active agent may be formulated as a suspension according to the embodiments described herein.

In other embodiments, the first active agent may be formulated as a suspension according to the embodiments described herein, and the second active agent may be formulated as a solution according to the embodiments described herein.

Concentration in Various Ocular Tissues—Delivered as an Ophthalmic Suspension

In some embodiments, a suspension of Compound-I or its free base provides similar concentration of the first active agent at the central choroid and the central retina compared to the concentration of the first active agent delivered in Gel Drop form (discussed infra).

In some embodiments, Tris-based suspension of Compound-I or its free base with or without a second active agent increases the bioavailability of the first active agent at the central choroid and the central retina, while reducing concentration at the cornea and preventing and/or treating corneal disruptions and or diseases (e.g., corneal edema, ulceration, abnormalities, etc.). In some embodiments, topical delivery of Compound-I or its free base formulated in Tris-base reduces corneal concentration of Compound-I by about 5-10×, 10-20×, 20-30×, 30-40×, or about 50-100× compared to the corneal concentration of equimolar Compound-I or its free base delivered as a Gel Drop.

The combined effects of decreasing corneal drug exposure so as to avoid poor ocular tolerability while maintaining or increasing posterior segment bioavailability so as to increase inhibition of receptor tyrosine kinase (RTK), for example, VEGFR, significantly increases the therapeutic index and corresponding benefits to patients. The additional prevention and/or treatment of disruptions to the anterior surface of the eye with a second active agent, such as an EGFR modulator (e.g., activator), further improves the therapeutic index and corresponding benefits to patients.

Once or twice daily administration of about 0.005%-about 5.0% w/v Compound-I suspension of the present application for 30-90 days or 4-6 months is well tolerated in the eye.

Gel Drop

In some embodiments the ophthalmic composition or formulation of the present application is formulated as a Gel Drop. The Gel Drop formulation includes no more than about 0.05% of sodium phosphate monobasic monohydrate to provide the required buffering capacity and free-flowing, filterable formulations at about 0.005%-about 2.0% Compound-I and/or at about 0.005%-about 5% of a second active agent without the need for surfactant additives.

The Gel Drop formulation of the application comprises about 0.005% to about 2.0% w/v of the first active agent of Formula I or II, or a pharmaceutically acceptable salt thereof, for example, Compound-I. The concentration of Compound-I or its free base (Formula II) in the Gel Drops may be about 0.005%-about 0.01%, about 0.01%-about 0.05%, about 0.05%-about 0.1%, about 0.1%-about 0.2%, about 0.2%-about 0.3%, about 0.3%-about 0.4%, about 0.4%-about 0.5%, about 0.5%-about 0.6%, about 0.6%-about 0.7%, about 0.7%-about 0.8%, about 0.8%-about 0.9%, about 0.9%-about 1.0%, or about 1.0%-about 2.0% w/v for topical administration. In some embodiments, the Gel Drops include about 0.005%, about 0.05%, about 0.1%, about 0.2%, about 0.3%, about 0.4%, about 0.5%, about 0.6%, about 0.7%, about 0.8%, about 0.9%, about 1.0%, or about 2% w/v of Compound-I or its free base (Formula II).

The Gel Drop formulation of the application may further comprise about 0.00001%-about 5.0% w/v of the second active agent, or a pharmaceutically acceptable salt thereof, for example, nicotinic acid, nicotinamide or vitamin K, or a combination thereof. The Gel Drop formulation of the application may further comprise about 0.00001%-about 1.0%, about 0.00001%-about 0.1%, about 0.00001%-about 0.01%, about 0.00001%-about 0.001%, about 0.00001%-about 0.0002%, or about 0.00001%-about 0.0001% w/v of the second active agent, or a pharmaceutically acceptable salt thereof, for example, nicotinic acid, nicotinamide or vitamin K, or a combination thereof. The concentration of the second active agent in the Gel Drops may be about 0.00001%-about 0.0001%, 0.000012%-about 0.0001%, 0.000014%-about 0.0001%, 0.000016%-about 0.0001%, 0.000018%-about 0.0001%, 0.00002%-about 0.0001%, 0.00003%-about 0.0001%, 0.00004%-about 0.0001%, 0.00005%-about 0.0001%, 0.00006%-about 0.0001%, 0.00007%-about 0.0001%, 0.00008%-about 0.0001%, 0.00009%-about 0.0001%, 0.000016%-about 0.00009%, 0.000018%-about 0.00009%, 0.00002%-about 0.00009%, 0.00003%-about 0.00009%, 0.00004%-about 0.00009%, 0.00005%-about 0.00009%, 0.00006%-about 0.00009%, 0.00007%-about 0.00009%, or 0.00008%-about 0.00009% w/v for topical administration. In some embodiments, the Gel Drops include about 0.00001%, 0.00002%, 0.00003%, 0.00004%, 0.00005%, 0.00006%, 0.00007%, 0.00008%, 0.000081%, 0.000082%, 0.000083%, 0.000084%, 0.000085%, 0.000086%, 0.000087%, 0.000088%, or 0.000089% w/v of the second active agent.

The Gel Drop formulation of the application may further comprise about 0.5 µM, about 0.6 µM, about 0.7 µM, about 0.8 µM, about 0.9 µM, about 1 µM, about 2 µM, about 3 µM, about 4 µM, about 5 µM, about 6 µM, about 7 µM, about 8 µM, or about 9 µM of a second active agent, or a pharmaceutically acceptable salt thereof, for example, nicotinic acid, nicotinamide, or vitamin K, or a combination thereof. In some embodiments, the concentration of the second active agent is about 1 µM.

In some embodiments, the Gel Drop ophthalmic compositions of the present application include glycerin as a tonicity agent. Some embodiments of the application provide ophthalmic composition including mannitol. The glycerin or mannitol content at an amount to prevent any changes in the solubility of Compound-I, and at a level of about 2.0-about 2.5%, glycerin provides an osmolality of about 225-about 300 mOsm/kg depending on the phosphate concentration. In additional embodiments, glycerin is about 2% and phosphate is about 0.05% of the gel drop ophthalmic composition. The concentrations of glycerin and phosphate of the present application is in an amount that the tonicity level of the ophthalmic composition is about 240 mOsm/kg.

The Gel Drop ophthalmic composition of the present application may further include Benzalkonium Chloride (BAK). In some embodiments, the BAK content is about 0.005%, sufficient for preservation of the ophthalmic composition against microbial contamination. In some embodiments of the present application, BAK is not required for use of ophthalmic composition in a sterile, single-use product.

In some embodiments, the Gel Drop ophthalmic formulation of Compound-I includes: about 0.005%-about 2.0% Compound-I or its free base, about 0.05% sodium phosphate, about 2% glycerin as the tonicity adjusting agent, about 0.005% BAK as a preservative, water (purified, i.e., distilled, or deionized) as a vehicle, and sodium hydroxide to adjust pH to 6.0. In one embodiment, no other excipients are added.

The Gel Drop of the application comprises about 0.005%-about 2.0% of the active agent of Formula I or II, or a pharmaceutically acceptable salt thereof, for example, Compound-I, and about 0.01%-about 0.05%, about 0.05-about 0.09%, or about 0.09-about 0.2% w/v sodium phosphate monobasic monohydrate. In a specific embodiment, the Gel Drop comprises about 0.05%, about 0.05-0.2%, or about 0.2% w/v sodium phosphate monobasic monohydrate buffer. Other equivalent buffer systems well known in the art are also used in the Gel Drop of the present application. In one embodiment, Compound-I or its free base is formulated as about 0.4%-about 2.0% first active agent, about 5% Cremophor RH40, about 2.0% glycerin, and about 0.005% BAK.

In one embodiment, the Gel Drop of Compound-I includes about 0.3%-about 2.0% (3-20 mg/mL) Compound-I, about 0.05%-about 0.2% Sodium Phosphate, and about 2% glycerin. The pH of the composition is between pH 5.0-7.0.

The Gel Drop ophthalmic formulation of Compound-I and a second active agent includes: about 0.005%-about 2.0% Compound-I or its free base, about 0.00001%-about 5% (e.g., about 0.00001%-about 0.0002%, or about 0.00001%-about 0.0001%) second active agent, about 0.05% sodium phosphate, about 2% glycerin as the tonicity adjusting agent, about 0.005% BAK as a preservative, water (purified, i.e., distilled, or deionized) as a vehicle, and sodium hydroxide to adjust pH to 6.0. In one embodiment, no other excipients are added.

The Gel Drop of the application comprises about 0.005%-about 2.0% of the active agent of Formula I or II, or a pharmaceutically acceptable salt thereof, for example, Compound-I, about 0.00001%-about 5% (e.g., about 0.00001%-about 0.0002%, or about 0.00001%-about 0.0001%) second active agent, and about 0.01%-about 0.05%, about 0.05-about 0.09%, or about 0.09-about 0.2% w/v sodium phosphate monobasic monohydrate. In a specific embodiment, the Gel Drop comprises about 0.05%, about 0.05-0.2%, or about 0.2% w/v sodium phosphate monobasic monohydrate buffer. Other equivalent buffer systems well known in the art are also used in the Gel Drop of the present application. In one embodiment, Compound-I or its free base is formulated as about 0.4%-about 2.0% first active agent, about 0.005%-about 5.0% second active agent, about 5% Cremophor RH40, about 2.0% glycerin, and about 0.005% BAK.

In one embodiment, the Gel Drop of Compound-I includes about 0.3%-about 2.0% (3-20 mg/mL) Compound-I, about 0.005%-about 5.0% second active agent, about 0.05%-about 0.2% Sodium Phosphate, and about 2% glycerin. The pH of the composition is between pH 5.0-7.0.

The present application provides Gel Drop of the agents (e.g., the first active agent and the second active agent) of the present application formulated in the presence of excipients such as, without being limiting example, Povidone, polysorbate 80 (PS80), polyethylene glycol (PEG) 400, tyloxapol, poloxamer, glycerin, and BAK in a phosphate buffer.

Eye Drops

Disclosed herein is a formulation, comprising a first active agent, e.g., a compound of Formula I or II, and/or a second active agent, e.g., nicotinic acid, nicotinamide, or vitamin K, or a combination thereof, as eye drops, a form of drug delivery that is pharmaceutically-acceptable to patients, convenient, safe, with an onset of action of several minutes. A standard eye drop used in therapy according to U.S. federal regulatory practice is sterile, have a pH of about 6.0-7.4, and, if to be used more than once, contains a preservative but has a limited shelf life after opening, usually one month. If the eye drops are packaged in a sterile, single use only unit-dose dispenser, the preservative can be omitted.

One method of eye drop formulation comprises the purest forms of the disclosed compound of Formula I or II (e.g., greater than 99% purity) and/or of the second active agent, and the compound and/or the second active agent are mixed with buffer and tonicity adjusters, to adjust for physiological pH and osmolarity. Examples of buffering agents to maintain or adjust pH include, but are not limited to, acetate buffers, citrate buffers, phosphate buffers and borate buffers. Examples of tonicity adjustors are sodium chloride, mannitol and glycerin. In some embodiments, other pharmaceutically acceptable ingredients are also added.

The formulated solution is then aliquoted into either a plurality of discrete, sterile disposable cartridges each of which is suitable for unit dosing, or a single cartridge for unit dosing. Such a single disposable cartridge is, for example, a conical or cylindrical specific volume dispenser, with a container having side-walls squeezable in a radial direction to a longitudinal axis in order to dispense the container contents therefrom at one end of the container.

The present application provides ophthalmic eye-drop solutions/suspensions packaged in multi-dose form or single dose form, for example, as a plastic bottle with an eye-dropper. In multi-dose form formulations, preservatives are required to prevent microbial contamination after opening of the container. Suitable preservatives include, but are not limited to: benzalkonium chloride, thimerosal, chlorobutanol, methyl paraben, propyl paraben, phenylethyl alcohol, edetate disodium, sorbic acid, polyquarternium-1, or other agents known to those skilled in the art, and all of which are contemplated for use in the present application. Such preservatives are typically employed at a level of from 0.001 to about 1.0% weight/volume.

Without wishing to be bound by theory, the formulation of the present application in an eye drop provides a pulse entry of the drug. The route by which Compound-I obtains access to the posterior segment is not by direct diffusion through the cornea with subsequent diffusion through the aqueous humor, vitreous humor, retina and ultimately the choroid. Rather, the Compound-I compound achieves notable bioavailability posteriorly following topical instillation using a circumferential route around, rather than through, the globe.

In certain clinical conditions, the eye drop solutions/suspensions can be formulated with other pharmaceutical agents, in order to attenuate the irritancy of the other ingredient and to facilitate clinical response. Such agents include, but are not limited to, a vasoconstrictor such as phenylephrine, oxymetazoline, napthazoline or tetrahydrozoline; a mast-cell stabilizer such as olopatadine; an antihistamine such as azelastine; an antibiotic such as tetracycline; a steroidal anti-inflammatory drug such as betamethasone; a non-steroidal anti-inflammatory drug such as diclofenac; an immunomodulator such as imiquimod or interferons; and antiviral agents such as valaciclovir, cidofovir and trifluridine. The doses used for the above described purposes vary, but are in an effective amount to suppress discomfort, itch, irritation, or pain in the eye. When the compositions are dosed topically, the "pharmaceutically effective amount" of a compound of Formula I or II can generally be in a concentration range of from 0.05 mg/mL to about 10 mg/mL and the "pharmaceutically effective amount" of the second active agent can generally be in a concentration range of from 0.05 mg/mL to about 10 mg/mL, with 1 to 4 drops of the composition administered as a unit dose 1 to 4 times per day. The most common method of ocular drug delivery is the instillation of drops into the cornea (i.e., "eye drops").

A key requirement is that the formulation be sterile and produced in a sterile environment. An ideal disclosed compound for use in ophthalmic solutions/suspensions should be soluble and/or miscible in aqueous media at normal ocular pH and tonicity. Moreover, the disclosed compounds should be stable, non-toxic, long acting, and sufficiently potent to counteract dilution of drug concentration by blinking and tearing.

Dosage Forms

The formulation of the present application may be suitable for ophthalmic use. In one embodiment the formulation is a solution. The solution of the present application may be a clear, colorless, sterile, isotonic, buffered aqueous free-flowing liquid preparation. The drug product (e.g., the first active agent and/or the second active agent) has a pH of approximately 6.0 and may be stored at +5° C. The drug product may be provided in a container closure system consisting of a semi-transparent ophthalmic dispenser bottle with a dropper tip and cap.

In some embodiments, the clinical concentration of Compound-I ophthalmic solution or suspension is equal to or less than about 0.1 mg/mL, equal to or less than about 0.2 mg/mL, about 0.2-about 1.0 mg/mL, about 0.3-about 1.0 mg/mL, about 0.4-about 1.0 mg/mL, about 0.5-about 1.0 mg/mL, about 0.6-about 1.0 mg/mL, about 0.7-about 1.0 mg/mL, about 0.8-about 1.0 mg/mL, about 0.9-about 1.0 mg/mL, about 1.0-about 2.0 mg/mL, about 2.0-about 3.0 mg/mL, about 3.0-about 4.0 mg/mL, about 4.0-about 5.0 mg/mL, about 5.0-about 6.0 mg/mL, about 5.0-about 10.0 mg/mL, about 10-about 20 mg/mL, about 20-about 30 mg/mL, about 30-about 40 mg/mL, or about 40-about 50 mg/mL.

In other embodiments, the clinical concentrations of Compound-I and the second active agent ophthalmic solution or suspension are independently equal to or less than about 0.1 mg/mL, equal to or less than about 0.2 mg/mL, about 0.2-about 1.0 mg/mL, about 0.3-about 1.0 mg/mL, about 0.4-about 1.0 mg/mL, about 0.5-about 1.0 mg/mL, about 0.6-about 1.0 mg/mL, about 0.7-about 1.0 mg/mL, about 0.8-about 1.0 mg/mL, about 0.9-about 1.0 mg/mL, about 1.0-about 2.0 mg/mL, about 2.0-about 3.0 mg/mL, about 3.0-about 4.0 mg/mL, about 4.0-about 5.0 mg/mL, about 5.0-about 6.0 mg/mL, about 5.0-about 10.0 mg/mL, about 10-about 20 mg/mL, about 20-about 30 mg/mL, about 30-about 40 mg/mL, or about 40-about 50 mg/mL.

In one embodiment of the present application the strength of the compound of Formula I or II is about 0.005%-about 5.0% (about 0.5-about 50 mg/mL). A desired pharmacologic activity (or concentration) of the formulation of the present application against pathologic choroidal and retinal neovascularization is achieved following ocular administration of formulations containing about 0.005%, about 0.05%, about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, or about 5.0% w/v of Compound-I. The present application provides that, following topical ocular administration with an optimal dose (for example, between about 0.005% and about 5.0%) the pharmacologically active concentration is achieved and maintained in the central choroid target tissue. In one embodiment the first active agent (Formula II or Compound-I) is formulated as about 0.005-about 5.0% w/v concentration, the second active agent (nicotinic acid, nicotinamide, or vitamin K, or a combination thereof) is formulated as about 0.005-about 5.0% w/v concentration, and the combination is dosed once or twice a day per eye for more than 60 consecutive days. The plasma concentrations observed following topical administration are substantially below the level expected to produce systemic toxicity.

TABLE 2

In vitro Summary of pharmacodynamic properties for Compound-I

| In Vitro Assay | $IC_{50}$ = nM (ng/mL) |
|---|---|
| Inhibition of recombinant VEGFR-2 tyrosine kinase using exogenous substrate | 10.55 (6) |

TABLE 2-continued

In vitro Summary of pharmacodynamic properties for Compound-I

| In Vitro Assay | IC$_{50}$ = nM (ng/mL) |
|---|---|
| Inhibition of recombinant FGFR-2 tyrosine kinase using exogenous substrate | 8.79 (5) |
| Inhibition of recombinant PDGFR tyrosine kinase using exogenous substrate | 2636.67 (1500) |
| Inhibition of recombinant EGFR tyrosine kinase using exogenous substrate | 5853.40 (3330) |
| Inhibition of recombinant IR tyrosine kinase using exogenous substrate | 10283.00 (5850) |
| Inhibition of VEGF-stimulated VEGFR-2 autophosphorylation in intact cells | 5.27 (3) |
| Inhibition of VEGF-stimulated mitogenesis in HUVECs | 14.06 (8) |

In some embodiments, Compound-I exhibits potent inhibition of tyrosine kinase activity for several proangiogenic growth factor receptors, with IC$_{50}$ of less than about 100 nM (see Table 3). Compound-I also blocks the high-affinity VEGF receptors, e.g., VEGFR-1/Flt-1, but with lower potency (with IC$_{50}$ of about 122 nM (69.41 ng/mL)).

TABLE 3

In Vitro Inhibition of Tyrosine Kinases using a 10-point Titration Curve (257 nM-5000 nM) for Compound-I

| Kinase | IC$_{50}$ – nM (ng/mL) for Compound-I |
|---|---|
| AURKB (Aurora B) | 207 (117.76) |
| FGFR-1 | 8.50 (4.84) |
| FGFR-2 | 3.08 (1.75) |
| FGFR-3 | 33.9 (19.29) |
| FGFR4 | 500 (284.45) |
| FLT1 (VEGFR-1) | 122 (69.41) |
| FLT3 | 419 (238.37) |
| FLT4 (VEGFR-3) | 54.2 (30.83) |
| FYN | 161 (91.59) |
| KDR (VEGFR-2) | 1.27 (0.72) |
| PDGFRA (PDGFR alpha) | 3120 (1774.97) |
| PDGFRB (PDGFR beta) | 1860 (1058.16) |
| TEK (Tie2) | 10.1 (5.75) |
| RET | 11.1 (6.31) |

Although VEGFR inhibition appears to be essential for reducing vascular permeability and preventing further neovascular growth, the simultaneous inhibition of VEGF signaling with inhibition of other growth factor signaling pathways (e.g., PDGF and angiopoietins/Tie2) may be linked to unique therapeutic outcomes. The therapeutic outcomes of a broader inhibition of signaling pathways may contribute to the regression of newly established pathologic vessels in the posterior segment of the eye.

In some embodiments, about 300 nM (about 170.67 ng/mL) of Compound-I inhibits VEGFR-2 kinase function (see Table 4). Substantial blockade of a similar set of proangiogenic growth factor receptors, including FGFRs1-3, Tie-2, and EphB-4 are also observed. An unexpected finding is that about 300 nM concentration of Compound-I inhibits the VEGFR-2 kinase function, which falls within the typical range found in the central choroid and retina following five days of topical ocular delivery.

TABLE 4

In Vitro Inhibition of Tyrosine Kinases by 300 nM (170.67 ng/mL) Compound-I

| Kinase | Mean % Inhibition at 300 nM Compound-I |
|---|---|
| EPHB-4 | 87 |
| FGFR-1 | 96 |
| FGFR-2 | 103 |
| FGFR-3 (K650E variant) | 104 |
| FLT4 (VEGFR-3) | 86 |
| KDR (VEGFR-2) | 104 |
| RET | 98 |
| RET (Y791F mutation) | 97 |
| TEK (Tie2) | 96 |

TABLE 5

In vitro Inhibition of Tyrosine Kinases by 1 µM (568.9 ng/mL) Compound-I

| Kinase | Mean % Inhibition at 1 µM Compound-I |
|---|---|
| ABL1 | 92 |
| ABL1 E255K | 90 |
| ABL1 G250E | 89 |
| ABL1 T315I | 101 |
| ABL1 Y253F | 93 |
| ACVR1B (ALK4) | 98 |
| AURKB (Aurora B) | 82 |
| BRAF V599E | 85 |
| EPHA-1 | 81 |
| EPHA-8 | 85 |
| EPHB-1 | 83 |
| EPHB-4 | 80 |
| FGFR-1 | 98 |
| FGFR-2 | 99 |
| FGFR-3 | 96 |
| FGFR-3 K650E | 100 |
| FGR | 91 |
| FLT-1 (VEGFR-1) | 86 |
| FLT-4 (VEGFR-3) | 95 |
| KDR (VEGFR-2) | 98 |
| LCK | 97 |
| LYN A | 81 |
| LYN B | 91 |
| MAP4K4 (HGK) | 100 |
| MAP4K5 (KHS1) | 94 |
| MAPK14 (p38 alpha) | 86 |
| MINK1 | 100 |
| PDGFRA T674I | 86 |
| PTK6 (Brk) | 88 |
| RET | 98 |
| RET Y791F | 94 |
| SNF1LK2 | 82 |
| SRC | 91 |
| SRC N1 | 83 |
| TEK (Tie2) | 99 |
| YES1 | 98 |

Overview of Drug Substance and Drug Product

Drug Product: Compound-I and/or second active agent ophthalmic formulations for clinical studies are manufactured in dosage strengths between 0.05%-1.0% of Compound-I and about 0.00001%-about 5% (e.g., about 0.00001%-about 0.0002%, or about 0.00001%-about 0.0001%) the second active agent. In some embodiments, Compound-I dosage in the formulation is 0.05%, 0.1%, 0.2%, 0.3%, 0.4%, 0.6%, 0.8%, or 1.0%. In some embodiments, second active agent dosage in the formulation is 0.05%, 0.1%, 0.2%, 0.3%, 0.4%, 0.6%, 0.8%, 1.0%, 2.0%, 3.0%, 4.0% or 5.0%. Compound-I and/or second active agent Ophthalmic Formulations (solutions or suspensions) are for daily, single use, topical administration to the eye in a clinical setting. In addition to the first and second active ingredients, in some embodiments the drug product may further contain about 0.005% BAK as a preservative, purified water as vehicle, and is pH-adjusted with sodium hydroxide to pH 6.0.

Sodium Phosphate-Based Gel Drop

The ophthalmic benefits of Compound-I in a sodium phosphate-based formulation (listed in Table 6) results from the self-gelling properties of the API in buffers, such as sodium phosphate. Spontaneous formation of self-forming, thixotropic gel of Compound-I from a clear solution is formed by increasing first active agent concentration in sodium phosphate. Once the first active agent concentration in the phosphate buffer reaches super-saturated state, insoluble particulates of Compound-I are observed within the gel.

The current state of the art predicts that application of a gel with increased viscosity to the surface of the eye would increase corneal residence time. Increased corneal residence time in turn facilitates ocular drug absorption. As a result, the intraocular drug concentrations of viscous gels would be increased in comparison to non-viscous formulations, such as water-like solutions. One way to increase viscosity is to use various viscosity-enhancing excipients, e.g., carboxymethylcellulose, which in effect achieves increased intraocular absorption of different drug substances following topical ocular administration. The present application provides a thixotropic gel of Compound-I and/or a second active agent formed in the absence of any viscosity-enhancing excipients. For example, when Compound-I or Compound-I and a second active agent are dissolved into a simple buffer, such as sodium phosphate, a thixotropic gel is formed. The thixotropic gel, which is formed without any viscosity-enhancing excipients, is formulated as a Gel Drop.

The present application provides dose-dependent and dose-frequency dependent delivery of Compound-I to the posterior segment eye tissues.

The Gel Drop formulations of the present application (listed in Table 6) differ among each other in several aspects, such as first active concentration, sodium phosphate concentration, presence or absence of tonicity (glycerin) or preservative (benzalkoniumchloride/BAK) agents, solubilizing surfactants (polysorbate 80, tyloxapol, and/or poloxamer), and pH.

Tromethamine-Based Suspension

The present application provides a suspension of Compound-I and/or a second active agent in a tromethamine-based formulation. In some embodiments, the suspension of Compound-I and/or the second active agent in a tromethamine-based formulation has equal to or more than 95% of the first active drug substance in an insoluble form. This characteristic is distinguishable from the soluble or semi-soluble state of Compound-I in the Gel Drop (the Gel Drop (gel), which is not an entirely soluble state as concentration of the first active agent increases) or in a Cyclodextrin-based formulation. Tromethamine-based formulations of Compound-I show increased turbidity with increasing first active agent concentration. Administering a topical drop of Compound-I and/or second active agent suspension to the eye, which is a combination of soluble and insoluble first active agent components, are beneficial with respect to both safety/tolerability and efficacy.

The present application provides Compound-I in the tromethamine-based suspension, delivered at concentrations to the target tissues between 10-1000× of the cellular $IC_{50}$ for the various pro-angiogenic RTKs. See, e.g., Table 7.

The corneal safety and tolerability of topical Compound-I is a direct consequence of the amount of soluble (as opposed to insoluble) first active agent applied to the corneal surface, and the resultant corneal tissue concentration. In some embodiments, subjects who receive topical ocular administration of the tromethamine-based suspension are able to tolerate up to higher level of the first active agent concentration in the formulation, as compared to equimolar formulations of the sodium phosphate-based Gel Drop. The corneal safety and tolerability of topical Compound-I is also a consequence of the administration of a second active agent, e.g., nicotinic acid, nicotinamide, or vitamin K, or a combination thereof, which is a modulator (e.g., activator) of EGFR that prevents or treats corneal disruptions or diseases caused by inhibition of EGFR.

TABLE 6

PK results with topical ocular formulation of Compound-I in Sodium Phosphate-based Gel Drop

| CD* mg/ml | pH | Phos % | BAK % | Gly % | PS80 % | Tylox % | Polox % | Osmo | Days Dosing | Dose x per Day | MEAN [choroid] nM | 5D [choroid] nM | Mean [retina] nM | SD [retina] nM | Mean [AH] nM | SD [AH] nM | [plasma] nM |
|---|---|---|---|---|---|---|---|---|---|---|---|---|---|---|---|---|---|
| 6 | 5.9 | 0.05 | 0.005 | 2 | 1 | 0.1 | 0.2 | 270 | 4 | 3x | 22.40 | | | | 222 | | 15.6 |
| 5 | 6 | 0.2 | 0.005 | 2 | | | | 273 | 5 | 3x | 1160 | | | | | | |
| 6 | 5.9 | 0.15 | | | | | | 80 | 4 | 3x | 823 | | | | 50.9 | | 12.5 |
| 6 | 6.1 | 0.05 | 0.005 | 2 | 1 | 0.1 | | 248 | 5 | 3x | 779 | | | | | | |
| 6 | 5.9 | 0.1 | 0.005 | 2 | | | 0.2 | 257 | 4 | 3x | 768 | | | | 55.4 | | 8.43 |
| 4 | 6.0 | 2 | 0.005 | 2 | 1 | 0.2 | | | 5 | 3x | 760 | 150 | 97.6 | 30.2 | 21.1 | 8.24 | 8.06 |
| 2 | 6.1 | 0.05 | 0.005 | 2 | 1 | 0.1 | | 239 | 5 | 3x | 660 | | | | | | |
| 5 | 6 | 0.2 | 0.005 | 2 | 1 | | 0.2 | 288 | 5 | 3x | 612 | | | | | | |
| 2 | 6.0 | 0.02 | 0.005 | 2 | 1 | 0.2 | | | 5 | 3x | 599 | 225 | 92.9 | 28.6 | 13.8 | 3.04 | 4.46 |
| 4 | 6.0 | 0.2 | 0.005 | 2 | | | | | 5 | 3x | 596 | 105 | 68.3 | 53.4 | 25 | 5.4 | 5.84 |
| 2 | 6 | | 0.005 | 2 | | | | 232 | 5 | 3x | 589 | | <LLoQ | | 30 | | 5.41 |
| 2 | 6 | 0.05 | 0.005 | 2 | 1 | | | 261 | 5 | 3x | 559 | | 126 | | 25.5 | | 4.15 |
| 1 | 6.1 | | 0.005 | 2 | | | | 230 | 5 | 3x | 537 | | | | | | |
| 2 | 6.0 | 0.2 | 0.005 | 2 | | | | | 5 | 3x | 532 | 238* | 34.8 | 69.5 | 14.8 | 1.81 | 4.47 |
| 2 | 6.0 | 0.05 | 0.005 | 2 | | | | | 5 | 3x | 528 | 106 | 113 | 42.7 | 32.2 | 11.3 | 5.79 |
| 2 | 6.0 | 0.1 | 0.005 | 2 | | | | | 5 | 3x | 525 | 51.3 | 42.9 | 50.5 | 18.9 | 5.69 | 5.71 |
| 1 | 6.0 | 0.2 | 0.005 | 2 | | | | | 5 | 3x | 519 | 44.4 | 90.9 | 20.8 | 20.6 | 4.16 | 3.97 |
| 2 | 6.1 | 0.15 | | | | | | 34 | 4 | 3x | 466 | | | | 13.7 | | 4.81 |
| 2 | 6.1 | | 0.005 | 2 | | | | 229 | 5 | 3x | 462 | | | | | | |
| 1 | 6.0 | 0.2 | 0.005 | 2 | 1 | 0.2% | | | 5 | 3x | 423 | 34.1 | 32.7 | 37.8 | 6.27 | 1.06 | 2.89 |
| 2 | 6 | 0.05 | 0.005 | 2 | | | | 244 | 5 | 3x | 422 | | 121 | | 27.8 | | 5.92 |

TABLE 6-continued

PK results with topical ocular formulation of Compound-I in Sodium Phosphate-based Gel Drop

| CD* mg/ml | pH | Phos % | BAK % | Gly % | PS80 % | Tylox % | Polox % | Osmo | Days Dosing | Dose x per Day | MEAN [choroid] nM | SD [choroid] nM | Mean [retina] nM | SD [retina] nM | Mean [AH] nM | SD [AH] nM | [plasma] nM |
|---|---|---|---|---|---|---|---|---|---|---|---|---|---|---|---|---|---|
| 1 | 6 | 0.05 | 0.005 | 2 | | | | | 5 | 3x | 398 | 81.6 | 101 | 30.1 | 16.4 | 6.08 | 4.45 |
| 2 | 5.9 | 0.05 | 0.005 | 2 | | | | 233 | 5 | 3x | 362 | | | | | | |
| 1 | 6 | | 0.005 | 2 | | | | 234 | 5 | 3x | 359 | | | | 17.1 | | |
| 2 | 6 | 0.2 | 0.005 | 2 | 1 | | | 281 | 5 | 3x | 357 | | 102 | | 19.7 | | 4.94 |
| 2 | 6.1 | 0.15 | | | | | | 22 | 5 | 3x | 356 | | | | | | |
| 2 | 6.0 | 0.05 | 0.005 | 2 | 1 | 0.2 | | | 5 | 3x | 349 | 44.1 | 85.7 | 19.6 | 18.2 | 6.91 | 4.36 |
| 1 | 6 | | 0.005 | 2 | 1 | 0.1 | 0.2 | 237 | 5 | 3x | 339 | | | | | | |
| 2 | 6 | 0 2 | 0.005 | 2 | | | | 257 | 5 | 3x | 316 | | <LLoQ | | 29.5 | | 5.26 |
| 1 | 6.0 | 0.05 | 0.005 | 2 | 0.01 | 0.2 | | | 5 | 3x | 295 | 48.7 | 46.8 | 54.1 | 9.09 | 0.989 | 3.49 |
| 1 | 6 | 0.05 | 0.005 | 2 | 1 | | | 254 | 5 | 3x | | | | | | | |

*CD: Compound 1

TABLE 7

PK results with topical ocular Compound-I in tromethamine-based suspension

| CD* mg/mL | pH | Phos % | Tris | BAK % | Gly % | PS80 % | Tylox % | Polox % | Osmo | Days Dosing | Dose x per Day | MEAN [choroid] nM | SD [choroid] nM | Mean [retina] nM | SD [retina] nM | Mean [AH] nM | SD [AH] nM | [plasma] nM |
|---|---|---|---|---|---|---|---|---|---|---|---|---|---|---|---|---|---|---|
| 10 | 6 | 0.14 | 1 | 0.005 | 2 | | | | 414 | 5 | 3x | 1520 | | | | 410 | | |
| 5 | 6.0 | 0.14 | ~0.20 | 0.005 | 2 | 1 | 0.2 | | | 5 | 3x | 1190 | 551 | 210 | 85.2 | 195 | 190 | 13.3 |
| 4 | 6.0 | 0.14 | ~0.20 | 0.005 | 2 | 1 | 0.2 | | | 5 | 3x | 1040 | 397 | 151 | 71.7 | 30.2 | 9.43 | 9.2 |
| 6 | 6 | | | 0.6 | 0.005 | 2 | | | 366 | 4 | 3x | 928 | | | | 68.4 | | 8.31 |
| 4 | 5.0 | 0.14% | ~0.20 | 0.005 | 2 | | | | | 5 | 3x | 915 | 203 | 139 | 34.7 | 40.4 | 6.73 | 8.18 |
| 4 | 7.0 | 0.14% | ~0.20 | 0.005 | 2 | | | | | 5 | 3x | 770 | 226 | 169 | 122 | 27.3 | 6.55 | 5.4 |
| 5 | 6 | 0.14 | 1 | 0.005 | 2 | | | | 380 | 5 | 3x | 758 | | | | 34.9 | | |
| 6 | 6 | | 1 | 0.005 | 2 | | | | 214 | 4 | 3x | 701 | | | | 22 | | 5.68 |
| 4 | 6.0 | 0.14% | ~0.20 | 0.005 | 2 | | | | | 5 | 3x | 680 | 217 | 129 | 57.8 | 55.3 | 39.5 | 10.2 |
| 5 | 6.0 | 0.14% | ~0.20 | 0.005 | 2 | | | | | 5 | 3x | 574 | 91.1 | 113 | 28.4 | 50.5 | 9.51 | 7.87 |
| 2 | 6.0 | 0.14% | ~0.20 | 0.005 | 2 | 1 | 0.2 | | | 5 | 3x | 456 | 55.4 | 79.8 | 64 | 14.1 | 0.535 | 4.99 |
| 2 | 6.1 | | | 0.6 | 0.005 | 2 | 1 | 0.1 | 0.2 | 321 | 5 | 3x | 416 | | | | | | |
| 2 | 6.0 | 0.14% | ~0.20 | 0.005 | 2 | | | | | 5 | 3x | 405 | 121 | 51.5 | 35.7 | 12.9 | 6.17 | 3.39 |
| 2 | 6 | 0.14 | ~0.20 | 0.005 | 2 | | | | 276 | 5 | 3x | 352 | | <LLoQ | | 19.9 | | 5.4 |
| 2 | 6 | | | 0.6 | 0.005 | 2 | | | 312 | 5 | 3x | 321 | | | | | | |
| 1 | 6.0 | 0.14% | ~0.20 | 0.005 | 2 | | | | | 5 | 3x | 286 | 64.6 | 31.5 | 36.4 | 15.7 | 4.32 | 2.61 |
| 1 | 6.0 | 0.14% | ~0.20 | 0.005 | 2 | 1 | 0.2 | | | 5 | 3x | 202 | 27.8 | 18.5 | 36.9 | 3.07 | 0.41 | 1.91 |

*CD: Compound-I

The present application provides ocular bioavailability of Compound-I in the posterior segment upon administration of a tromethamine-based suspension. The ocular bioavailability of Compound-I in the posterior segment is directly proportional to the total amount of drug, Compound-I, administered (insoluble plus soluble, see Table 7). Although the insoluble drug particulates are not readily available to anterior segment tissues; the inherent and unique physicochemical properties of Compound-I allow both insoluble and soluble components to gain entry to posterior segment tissues, such as the choroid and retina. Consequently, even higher drug concentrations than those achieved with Gel Drop formulations containing equivalent amounts of the first active agent are achieved with the tromethamine-based suspension. Thus, tromethamine-based suspension provide: a) improved corneal tolerability and b) maintained or increased bioavailability to the posterior segment, particularly to the choroid, the primary target tissue for treating neovascular (wet) AMD. In addition, a second active agent, e.g., nicotinic acid, nicotinamide, or vitamin K, or a combination thereof, which is a modulator (e.g., activator) of EGFR that prevents or treats corneal disruptions or diseases caused by inhibition of EGFR, prevents and/or treats corneal disruptions potentially associated with the administration of Compound-I, thereby increasing the therapeutic index of Compound-I.

Cyclodextrin-Based Solution

Cyclodextrins, which are cyclic oligosaccharides made up of six to eight dextrose units (α-, β-, and γ-CDs) joined through one to four bonds, are well-known for their ability to act as a solubilizing agent for relatively insoluble drugs. See Stella & He, Cyclodextrins, *Toxicol. Pathol.*, 36: 30-42 (2008).

In some embodiments, 2-hydroxypropyl-β-cyclodextrin (HP-β-CD, also known as KLEPTOSE® HPB) at equal to or more than 1:6 molar ratio or Sulfobutylether-β-cyclodextrin (SBE-β-CD, also known as CAPTISOL®) at equal to or more than 1:2 ratio in the proposed clinical formulation, Compound-I or its free base and a second active agent Ophthalmic Solution, provide solubility that meets clinical dose strengths of 0.1-1.2% Compound-I.

In some embodiments, cyclodextrin-based solutions of Compound-I or its free base and/or a second active agent not only have improved solubility of the first active agent into a uniform solution, but, upon topical ocular administration, also have a novel and previously unobserved characteristic of significantly increased therapeutic index of the first active agent at the posterior segment of the eye. The solutions of Compound-I and/or the second active agent of the present application reduce anterior segment exposure of Compound-I, thereby increasing the concentration of the first active in the solution and increasing the frequency of its delivery in order to maintain high posterior segment concentrations. Both of these beneficial characteristics are related to the known property of cyclodextrin to form hydrophilic complexes with hydrophobic drugs. See Stella & He, Cyclodextrins, *Toxicol. Pathol.*, 36: 30-42 (2008). The administration of the second active agent as a combination with the first active agent prevents corneal disruptions or diseases caused by inhibition of EGFR by systemic diseases (e.g., cancer, diabetes), eye diseases, or administration of the first active agent, e.g., a compound of Formula I or II, thereby increasing the therapeutic index of the first active agent, e.g., Compounds of Formula I or II.

When formulated with Compound-I or its free base and/or a second active agent, cyclodextrin can form a clear, colorless solution which exhibits water-like viscosity. Following topical ocular administration, Compound-I/cyclodextrin complex has the appearance of being pharmacologically inactive and metabolically inert. The Compound-I/cyclodextrin complex confers corneal tolerability until cyclodextrin spontaneously dissociates from the first active agent, thus making available high concentration of Compound-I at its intended site of action in the posterior segment of the eye, e.g., choroid and retina.

In some embodiments, cyclodextrin-based solutions of Compound-I lower corneal exposures of Compound-I compared to Gel Drop formulations at similar drug concentrations. The use of cyclodextrin-based solutions of Compound-I provides about 10× reduction in corneal concentrations, as compared to dosing with equimolar formulations of the Gel Drop. In some embodiments, after 20-30 days of topical ocular dosing of about 0.2-2.0%, e.g., about 0.6%, Compound-I as a cyclodextrin-based solution, no untoward findings are attributed to test-article or vehicle. The present application provides higher concentrations of Compound-I within the posterior segment target tissues, such as at the central choroid and the central retina, when cyclodextrin-based solution of Compound-I is topically applied. In some embodiments, the combined effects of decreasing corneal drug exposure so as to avoid poor ocular tolerability, while increasing posterior segment bioavailability so as to increase RTK inhibition, significantly increases the therapeutic index and corresponding benefit(s) to treated subjects. In other embodiments, the combined effects of decreasing corneal drug exposure so as to avoid poor ocular tolerability and preventing or treating of corneal disruptions or disease by the second active agent, while increasing posterior segment bioavailability so as to increase RTK inhibition can significantly increase the therapeutic index and corresponding benefit(s) to treated subjects.

The present application provides expansion of the therapeutic window for both suspension-based formulations (see Example 3) and the cyclodextrin formulations of Compound-I due to significantly reduced exposure (about 10-100× or 1-2 log reduction). The reduced exposure improves corneal safety/tolerability, which allows higher concentrations or frequency of dosing of Compound-I to be administered topically. The higher concentration enables Compound-I to achieve higher back of the eye target tissue concentration, which improves the therapeutic efficacy of Compound-I.

In some embodiments, topical ocular dosing of ophthalmic gel drops is associated with high corneal tissue exposure (≥100 uM) and corresponding untoward observations in the anterior segment, such as discomfort, corneal and conjunctival inflammation, corneal epithelial erosion and/or thinning and degeneration. In contrast, repeated topical ocular dosing of Compound-I ophthalmic solution produces corneal exposure that are roughly 5 to 10-fold lower than an equimolar dose of ophthalmic gel drops, and are free of untoward clinical or histopathologic findings. Topical ocular dosing with Compound-I ophthalmic solution also achieves equal or higher target therapeutic exposure in the central choroid in comparison to an equimolar dose of the ophthalmic gel drop. Overall, the combination of decreased corneal exposure and corresponding improved ocular tolerability, while simultaneously maintaining or promoting drug delivery to the posterior segment target tissues, along with improved physicochemical stability, provides greater benefit to subjects compared to the ophthalmic Gel Drop formulation.

1- to 5-Day PK Results with Topical Ocular Compound-I in Cyclodextrin-Based Solutions The present application provides ocular pharmacokinetics of various formulations and dose regimens of Compound-I following topical ocular administration. Three dosage strengths in nine (9) different topical ocular formulations of Compound-I are used for dosing either once per day (q.d.) or twice per day (b.i.d.) for 1, 2, 3, 4, or 5 consecutive days. Subjects each receive about 30 μL bilateral topical ocular dose of one of three (3) Compound-I formulations, or vehicle formulation, using a positive displacement pipette.

The composition of each Compound-I formulation is described in Table 8A. All doses were administered within ±1 hour of the scheduled dose time. On day 1, Groups 1, 2, 4-6, 8, 10, 11, 13, 15, and 17 receive one dose (q.d.) for either one (1) or four (4) days. On days 1 through 4, Groups 3, 7, 9, 12, 14, and 16 receive b.i.d. dosing approximately 8 hours apart at 7:00 μM and 3:00 μM for four (4) days. Some subjects receive b.i.d dosing of vehicle only formulations for five (5) consecutive days.

In some embodiments, ocular sampling is performed at about 0.5, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, or about 24 hours post-dose relative to the day 1 dose. Aqueous humor, cornea, central and peripheral retina, and central and peripheral choroid samples are collected to monitor effects of treatment. Aqueous humor, cornea, central retina, and central choroid samples are assayed.

Table 8A-C lists 1- to 5-day PK results with topical ocular Compound-I in Cyclodextrin-based solutions.

TABLE 8A

Ocular Formulations

| | |
|---|---|
| Composition: | 0.3% Compound-I (3 mg/mL Compound-I) |
| | 0.05% Sodium Phosphate, monobasic, monohydrate, USP |
| | 2.0% glycerin, USP |
| | pH 6 |

TABLE 8A-continued

Ocular Formulations

| | |
|---|---|
| Physical Description: | Clear and colorless, extremely viscous |
| Composition: | 0.3% Compound-I (3 mg/mL Compound-I) |
| | 0.05% Sodium Phosphate, monobasic, monohydrate, USP |
| | 2.0% glycerin, USP |
| | pH 5.5 |
| Physical Description: | Clear and colorless |
| Composition: | 0.4% Compound-I (4 mg/mL Compound-I) |
| | 7% Hydroxypropyl-β-cyclodextrin (HPβCD), 0.7% Sodium Chloride, |
| | USP, 0.005% Benzalkonium chloride (BAK), NF |
| | pH 7.0 |
| Physical Description: | Clear and colorless, viscous |
| Composition: | 0.4% Compound-I (4 mg/mL Compound-I) |
| | 4% Hydroxypropyl-β-cyclodextrin (HPβCD), |
| | 0.7% Sodium chloride, USP, 0.005% Benzalkonium chloride (BAK), NF |
| | pH 7.0 |
| Physical Description: | Clear and colorless, viscous |
| Composition: | 0.4% Compound-I (4 mg/mL Compound-I) |
| | 4% Hydroxypropyl-β-cyclodextrin (HPβCD), 0.7% Sodium Chloride, USP, 0.005% Benzalkonium chloride (BAK), NF |
| | pH 6 |
| Lot Number: | BCL532-052(5) ALG-001 |
| Physical Description: | Clear and colorless, extremely viscous |
| Composition: | 0.4% Compound-I (4 mg/mL Compound-I) |
| | 7% Hydroxypropyl-β-cyclodextrin (HPβCD), |
| | 1% Tromethamine, USP, 0.4% Sodium Chloride, USP, |
| | 0.005% Benzalkonium chloride (BAK), NF, |
| | pH 7.0 |
| Physical Description: | Clear and colorless |
| Composition: | 0.6% Compound-I (6 mg/mL Compound-I) |
| | 7% Hydroxypropyl-β-cyclodextrin (HPβCD), |
| | 0.7% Sodium Chloride, USP, 0.005% Benzalkonium chloride (BAK), NF |
| | pH 7.0 |
| Physical Description: | Clear and colorless, viscous |
| Composition: | 0.6% Compound-I (6 mg/mL Compound-I) |
| | 7% Hydroxypropyl-β-cyclodextrin (HPβCD), 0.7% Sodium Chloride, USP, 0.005% Benzalkonium chloride (BAK), NF, |
| | pH 6.0 |
| Physical Description: | Clear and colorless, viscous |
| Composition: | 0.4% Compound-I (4 mg/mL Compound-I) |
| | 5% Cremophor RH40, 2.0% glycerin, USP, |
| | 0.005% Benzalkonium chloride (BAK), NF, pH 6.0 |
| Physical Description: | Clear and colorless |

Table 8B lists average Compound-I concentrations in aqueous humor, retina, choroid, and cornea (LLOQ: Lower Limit of Quantitation; the LLOQ is the lowest analyte concentration that can be quantified with acceptable precision and accuracy).

TABLE 8B

| | | Average Concentration of Compound-I (μM) | | | | | |
|---|---|---|---|---|---|---|---|
| Group | Time Point | Aqueous Humor | Central Retina | Peripheral Retina | Central Choroid | Peripheral Choroid | Cornea |
| 1 | 0.5 hr | 0.00162 | 0.0404 | 0.0291 | <LLOQ | <LLOQ | 57.6 |
|  | 1 hr | 0.00206 | <LLOQ | 0.0548 | <LLOQ | *0.0856 | 33.7 |
|  | 2 hr | 0.0103 | 0.0368 | 0.0779 | <LLOQ | 0.0575 | 44.5 |
|  | 8 hr | 0.0128 | 0.0340 | 0.0356 | <LLOQ | 0.134 | 29.2 |
|  | 24 hr | 0.00303 | <LLOQ | 0.0151 | <LLOQ | 0.0880 | 6.94 |
| 2 | 1 hr | 0.00996 | 0.0363 | 0.0961 | *0.207 | 0.737 | 112 |
|  | 8 hr | 0.0165 | 0.0380 | 0.0508 | *0.237 | 0.687 | 32.7 |
|  | 24 hr | 0.00336 | <LLOQ | 0.380 | *0.205 | 1.14 | 29.2 |
| 3 | 1 hr | 0.0142 | 0.0407 | 0.108 | 0.255 | 0.765 | 151 |
|  | 24 hr | 0.00774 | 0.0292 | 0.0597 | 0.283 | 0.892 | 82.1 |
| 4 | 1 hr | 0.00996 | 0.0431 | 0.0883 | 0.196 | 0.629 | 78.7 |
| 5 | 0.5 hr | <LLOQ | <LLOQ | 0.0227 | <LLOQ | <LLOQ | 21.0 |
|  | 1 hr | 0.00108 | 0.0211 | 0.0253 | <LLOQ | 0.0473 | 16.9 |

TABLE 8B-continued

| Group | Time Point | Average Concentration of Compound-I (μM) | | | | | |
|---|---|---|---|---|---|---|---|
| | | Aqueous Humor | Central Retina | Peripheral Retina | Central Choroid | Peripheral Choroid | Cornea |
| | 2 hr | 0.00862 | 0.0354 | 0.0253 | <LLOQ | 0.0509 | 28.1 |
| | 4 hr | 0.00911 | 0.0299 | 0.0312 | <LLOQ | 0.0775 | 14.1 |
| | 8 hr | 0.00667 | 0.0304 | 0.0333 | <LLOQ | 0.0874 | 7.74 |
| | 24 hr | 0.00228 | <LLOQ | *0.0103 | <LLOQ | 0.116 | 2.43 |
| 6 | 1 hr | 0.00323 | 0.0463 | 0.0634 | 0.319 | 0.311 | 21.8 |
| | 8 hr | 0.00742 | 0.0537 | 0.0349 | <LLOQ | 0.257 | 9.10 |
| | 24 hr | 0.00122 | 0.0241 | 0.0533 | <LLOQ | 0.343 | 2.33 |
| 7 | 1 hr | 0.00648 | 0.0469 | 0.0819 | 0.514 | 0.744 | 35.3 |
| | 24 hr | 0.00260 | 0.0313 | 0.0293 | 0.439 | 0.653 | 13.0 |
| 8 | 1 hr | 0.00978 | 0.0490 | 0.0497 | 0.367 | 0.797 | 63.2 |
| | 24 hr | 0.00483 | 0.0193 | 0.0177 | 0.218 | 1.20 | 37.4 |
| 9 | 1 hr | 0.0246 | 0.0633 | N/A | 0.456 | N/A | 237 |
| 10 | 1 hr | 0.00867 | 0.0667 | N/A | 0.251 | N/A | 93.9 |

AH LLOQ = 0.000903 μM
Central Retina LLOQ = 0.0181 μM
Peripheral Retina LLOQ = 0.00873 μM (Grps 1-8); LLOQ = 0.00898 μM (Grps 12-16)
Central Choroid LLOQ = 0.175 μM
Peripheral Choroid LLOQ = 0.0349 μM (Grps 1-8); LLOQ = 0.0359 μM (Grp 12-16)
Cornea LLOQ = 0.0181 μM (Grp 1-5); LLOQ = 0.0453 μM (Grp 6-8, 10-13, 15, 16A17); LLOQ = 0.0873 μM (Grp 4, 9, 16B)
N/A = Not Applicable; Samples not assayed per study protocol.
*Average based on n = 1.

Table 8C lists the summary of average ocular tissue concentrations of Compound-I in aqueous humor, central and peripheral retina, central and peripheral choroid, and cornea for Groups 1 through 10. Any values <LLOQ were excluded from statistical calculations. When all values are <LLOQ for a given time point, <LLOQ are reported as the average.

TABLE 8C

| Group | Time Point | Average Concentration of Compound-I (μM) | | | | | |
|---|---|---|---|---|---|---|---|
| | | Aqueous Humor | Central Retina | Peripheral Retina | Central Choroid | Peripheral Choroid | Cornea |
| 11 | 1 hr | 0.00284 | 0.0397 | N/A | 0.193 | N/A | 20.7 |
| | 24 hr | *0.00205 | *0.0185 | N/A | *0.179 | N/A | 0.487 |
| 12 | 1 hr | 0.00651 | 0.0521 | 0.0842 | 0.528 | 0.560 | 27.4 |
| 13 | 1 hr | 0.0102 | 0.0934 | N/A | 0.372 | N/A | 123 |
| | 24 hr | 0.00518 | 0.0246 | N/A | 0.319 | N/A | 39.1 |
| 14 | 1 hr | 0.0209 | 0.0817 | 0.151 | 7.19 | 1.00 | 236 |
| 15 | 1 hr | 0.0114 | 0.0527 | N/A | 0.319 | N/A | 82.9 |
| 16 | 1 hr | 0.0179 | 0.0480 | 0.169 | 0.495 | 0.868 | 169 |
| 17 | 1 hr | 0.00445 | 0.0468 | N/A | 0.297 | N/A | 32.0 |

AH LLOQ = 0.000903 μM

Central Retina LLOQ = 0.0181 μM

Peripheral Retina LLOQ = 0.00873 μM (Grps 1-8); LLOQ = 0.00898 μM (Grps 12-16)

Central Choroid LLOQ = 0.175 μM

Peripheral Choroid LLOQ = 0.0349 μM (Grps 1-8); LLOQ = 0.0359 μM (Grp 12-16)

Cornea LLOQ = 0.0181 μM (Grp 1-5); LLOQ = 0.0453 μM (Grp 6-8, 10-13, 15, 16A17); LLOQ = 0.0873 μM (Grp 4, 9, 16B)

N/A = Not Applicable; Samples not assayed per study protocol.

*Average based on n = 1.

5-Day PK Results with Topical Ocular Compound-I in Cyclodextrin-Based Solutions

The present application provides ocular pharmacokinetics of various dose regimens of topical ocular solutions of Compound-I containing hydroxypropyl-β-cyclodextrin ("HDβCD") following ocular dose administration. Different topical ocular solutions of Compound-I are administered either once per day (q.d.) or twice per day (b.i.d.) for either 4 or 5 consecutive days. Subjects each receive a 30 μL bilateral topical ocular dose of one of four Compound-I dosage strengths.

All doses were administered with ±1 hour of the scheduled dose time, except some subjects receiving on day 1. Ocular sampling after administration of Compound-I is performed one hour following the first daily dose on day 5 for subjects, except in a few, where ocular sampling is performed 24 hours after the first daily dose on day 4.

Aqueous humor, cornea, central and peripheral retina, and central and peripheral choroid samples are collected. Cornea, central retina, and central choroid samples are assayed; aqueous humor, peripheral retina, and peripheral choroid samples are not assayed.

Table 9 (A-B) lists 5-day PK results with topical ocular Compound-I in cyclodextrin-based solutions.

TABLE 9A

Ocular Formulations

| | | |
|---|---|---|
| Formulation 1 (A) | Composition: | 0.4% Compound-I (as free base) 7.15% Hydroxypropyl-β-cyclodextrin 0.7% Sodium chloride pH 6.5 |
| | Physical Description: | Clear and colorless |
| Formulation 2 (B) | Composition: | 0.1% Compound-I (as free base) 1.79% Hydroxypropyl-β-cyclodextrin 0.85% Sodium chloride pH 6.5 |
| | Physical Description: | Clear and colorless |
| Formulation 3 (C) | Composition: | 0.2% Compound-I (as free base) 3.57% Hydroxypropyl-β-cyclodextrin 0.8% Sodium chloride pH 6.5 |
| | Physical Description: | Clear and colorless |
| Formulation 4 (D) | Composition: | 0.6% Compound-I (as free base) 10.72% Hydroxypropyl-β-cyclodextrin 0.6% Sodium chloride pH 6.5 |
| | Physical Description: | Clear and colorless |
| Formulation 5 (E) | Composition: | 0.4% Compound-I (as free base) 8.41% Hydroxypropyl-β-cyclodextrin 0.65% Sodium chloride pH 6.5 |
| | Physical Description: | Clear and colorless |
| Formulation 6 (F) | Composition: | 0.4% Compound-I (as free base) 10.51% Hydroxypropyl-β-cyclodextrin 0.65% Sodium chloride pH 6.5 |
| | Physical Description: | Clear and colorless |
| Formulation 7 (G) | Composition: | 0.4% Compound-I (as free base) 10.51% Hydroxypropyl-β-cyclodextrin 0.15% Sodium chloride 1.0% Tromethamine (Tris) pH 6.5 |
| | Physical Description: | Clear and colorless |
| Formulation 8 (H) | Composition: | 0.1% Compound-I (as free base) 2.63% Hydroxypropyl-β-cyclodextrin 0.8% Sodium chloride pH 6.5 |

TABLE 9A-continued

Ocular Formulations

| | | |
|---|---|---|
| | Physical Description: | |
| Formulation 9 (I) | Composition: | 0.6% Compound-I (as free base) 15.77% Hydroxypropyl-β-cyclodextrin 0.37% Sodium chloride pH 6.5 |
| | Physical Description: | Clear and colorless |

Table 9B lists a summary of average ocular tissue concentrations of Compound-I in central retina, central choroid, and cornea. Any values <LLOQ were excluded from statistical calculations. When all values were <LLOQ for a given time point, <LLOQ was reported as the average.

TABLE 9B

Average Compound-I concentrations in retina, choroid, and cornea.

| | | Average Concentration (μM) | | |
|---|---|---|---|---|
| Group | Time Point | Central Retina | Central Choroid | Cornea |
| 1 | 1 hr | 0.0670 | 0.308 | 35.1 |
| 2 | 1 hr | 0.0636 | 0.329 | 21.8 |
| 3 | 1 hr | 0.0579 | 0.313 | 18.2 |
| 4 | 1 hr | 0.0481 | 0.203 | 12.9 |
| 5a | 1 hr | 0.0403 | *0.199 | 12.8 |
| 5b | 24 hr | <LLOQ | 0.194 | 0.772 |
| 6a | 1 hr | 0.0469 | 0.309 | 10.6 |
| 6b | 24 hr | <LLOQ | *0.218 | 0.371 |
| 7 | 1 hr | 0.0332 | <LLOQ | 7.60 |
| 8 | 1 hr | 0.0376 | *0.210 | 5.41 |
| 9 | 1 hr | 0.0261 | *0.287 | 8.53 |
| 10 | 1 hr | 0.0534 | 0.264 | 16.7 |
| 11 | 1 hr | 0.0418 | 0.371 | 29.6 |
| 12 | 1 hr | 0.0464 | 0.210 | 16.3 |

Central Retina LLOQ = 0.0218 μM
Central Choroid LLOQ = 0.174 μM
Cornea LLOQ = 0.0174 μM
*Average based on n = 1

Concentrations of Compound-I (in μM) in Various Ocular Fluids and Tissues

In some embodiments, concentration of the first active agent in various tissues and fluids of the eye is measured upon topical ocular administration of a solution of about 0.4% (about 4 mg/mL) Compound-I and cyclodextrin. Average concentration of Compound-I is measured in the central choroid, central retina, aqueous humor, and cornea. Compound-I is in a solution (0.4% or 4 mg/mL) with 8.41% KLEPTOSE® and 0.142% phosphate buffer; 8.9% KLEPTOSE® HPB and 0.142% phosphate; 4.88% CAPTISOL® and 0.142% phosphate; or 4.88% CAPTISOL® and 0.122% phosphate. See Table 10A-B.

In some embodiments, upon topical ocular administration of a solution of about 0.4% (about 4 mg/mL) Compound-I and cyclodextrin, the central choroid concentration of Compound-I is between about 0.2 μM and about 0.8 μM. The central retina concentration of Compound-I is between about 0.05 μM-about 0.15 μM. In some embodiments, upon topical ocular administration of a solution of about 0.4% (about 4 mg/mL) Compound-I and cyclodextrin, the aqueous humor concentration of Compound-I is between about 0.003 μM-about 0.008 μM. And the corneal concentration of Compound-I is about 6.0 μM-about 40 μM. KLEPTOSE® HPB or CAPTISOL® is used in the solution of Compound-I administered topically to the eye.

In some embodiments, mean Compound-I ocular tissue concentrations following twice daily topical dosing with 0.3% Compound-I ophthalmic gel drop formulations with and without benzylalkonium chloride is highest in the cornea with between about 200 µM-about 350 µM in the cornea, between about 2.0 µM-about 5.0 µM in the peripheral choroid, between about 0.2 µM-about 0.7 µM in the central choroid, between about 0.05 µM-about 0.5 µM in the peripheral retina, and between about 0.01 µM-about 0.05 µM in the aqueous humor.

In some embodiments, Tris-based suspension formulations of Compound-I is well tolerated, without any corneal findings, and only with a few sporadic incidences of mild conjunctivitis. In some embodiments, mean Compound-I ocular tissue concentrations, assessed at 1 hour±15 minutes after the first daily topical ocular dose on day 30 for the twice daily topical dosing with 0.3% Compound-I Tris-based suspensions with and without benzylalkonium chloride, are highest in the cornea, for example, between about 2.00 µM-about 4.0 µM. The peripheral choroid concentration from the same dose is between about 0.7 µM-about 1.5 µM; the central choroid concentration is between about 0.3 µM-about 0.4 µM; the peripheral retina concentration is between about 0.08 µM-about 0.09 µM); central retina concentration is between about 0.04 µM-about 0.07 µM; and aqueous humor concentration is about 0.001 µM-about 0.002 µM.

The present application provides Cyclodextrin-based solutions (e.g., solutions comprising hydroxypropyl-beta-cyclodextrin (HP-β-CD, KLEPTOSE® HPB)) of Compound-I that were well tolerated when administered topically for up to 30 days, twice daily at about 0.1% Compound-I (in a solution with about 2.0%-about 2.5% HP-β-CD), twice daily at about 0.2% Compound-I (in a solution with about 4.0%-about 4.5% HP-β-CD), once or twice daily at about 0.4% Compound-I (in a solution with about 8.0%-about 8.5% HP-β-CD), and once or twice daily at about 0.6% Compound-I (in solution with up to about 14% HP-β-CD) in subjects. Moreover, in additional embodiments, cyclodextrin-based solutions of about 0.4% w/v Compound-I in KLEPTOSE® HPB, KLEPTOSE® HP, or CAPTISOL® are well-tolerated when dosed twice daily for up to 24 days.

The present application provides dose-limiting corneal toxicity observed with Compound-I ophthalmic Gel Drop formulations. In some embodiments, ophthalmic Gel Drop renders about five-fold to about fifteen-fold higher corneal concentrations of Compound-I compared to cyclodextrin based solution, and about fifty-fold to about hundred-fold higher corneal concentrations of Compound-I compared to Tris-based suspensions. Compound-I Tris-based suspensions and cyclodextrin-based solutions of the present application are well tolerated with no evidence of overt ocular toxicity. In some embodiments, once or twice daily administration for at least 30 days of about 0.005% to about 5.0% w/v of a cyclodextrin-based solution or a Tris-based suspension of Compound-I is well tolerated in subjects. The present application provides highest central choroid concentrations of Compound-I using Cyclodextrin-based solutions compared to equimolar doses of the gels and/or Tris-based formulations.

TABLE 10A

Average concentration of Compound-I in µM in various ocular fluids and tissues

| Group | Central Choroid | Central Retina | Aqueous Humor | Cornea |
|---|---|---|---|---|
| 8 | 0.769 | 0.124 | 0.00656 | 12.3 |
| 9 | 0.259 | 0.0741 | 0.00313 | 8.05 |
| 10 | 0.212 | 0.0531 | 0.00184 | 6.49 |
| 11 | 0.345 | 0.101 | 0.00403 | 30.0 |

Values <LLOQ were excluded from statistical calculations.
Choroid LLOQ = 0.184 µM
Retina LLOQ = 0.0229 µM
AH LLOQ = 0.000918 µM
Cornea LLOQ = 0.0918 µM

TABLE 10B

Study Design

| Group | Total Daily Dose* (mg/day) | Conc.* (% w/v) | Dose Volume (µL/dose) | Number of Doses per Day | Total Dose Volume (µL/day) | Number of Male Animals |
|---|---|---|---|---|---|---|
| Group 8. Compound-I in 8.41% KLEPTOSE ® HPB**, 0.142% phosphate | 0.48 | 0.4 | 30/eye | 2 | 120 | 2 |
| Group 9. Compound-I in 8.90% KLEPTOSE ® HPB, 0.142% phosphate | 0.48 | 0.4 | 30/eye | 2 | 120 | 2 |
| Group 10. Compound-I in 4.88% CAPTISOL ®***, 0.142% phosphate | 0.48 | 0.4 | 30/eye | 2 | 120 | 2 |
| Group 11. Compound-I in 4.88% CAPTISOL ®, 0.122% phosphate | 0.48 | 0.4 | 30/eye | 2 | 120 | 2 |

*Total daily dose and concentration are expressed as free base equivalent of Compound-I (Formula II).
**Hydroxypropyl-β-cyclodextrin (HPβCD) from Roquette.
***CAPTISOL ® is a polyanionic β-cyclodextrin derivative with a sodium sulfonate salt separated from the lipophilic cavity by a butyl ether spacer group, or sulfobutylether (SBE).

Table 11 shows the corneal and central choroidal concentrations of Compound-I formulations.

TABLE 11

| Compound-I w/v % | Formulation Type | Dosing Frequency & Duration | Cornea [Compound I] (μM) | Central Choroid [Compound I] (μM) |
|---|---|---|---|---|
| 0.3% | Ophthalmic Gel Drop | Twice Daily 29 days | 236.00 | 0.340 |
| 0.3% | Tris Suspension | Twice Daily 30 days | 2.69 | 0.319 |
| 0.4% | Ophthalmic Solution (CAPTISOL ®) | Twice Daily 24 days | 6.49 | 0.212 |
| 0.4% | Ophthalmic Solution (KLEPTOSE ® HP) | Twice Daily 24 days | 8.05 | 0.259 |
| 0.4% | Ophthalmic Solution (KLEPTOSE ® HPB) | Twice Daily 24 days | 12.30 | 0.769 |

Phase I Protocol for Dose-Escalation Study in Patients with Neovascular AMD

The present application provides a Phase I study involving a twelve-week, open-label, dose-escalating, multi-center trial to evaluate the safety, tolerability, and pharmacokinetics following topical ocular administration of Compound-I in patients with neovascular age-related macular degeneration (AMD). Up to 60 patients total are treated one to two times daily with topical ocular dosing of Compound-I ophthalmic solution for three months, where three dose-escalating monotherapy arms and one adjunct therapy arm using a single intravitreal injection of LUCENTIS® plus the maximally-tolerated monotherapy dose are planned (15 patients per treatment arm). Patients that meet pre-specified vision and CNV lesion criteria confirmed by an independent reading center are allowed to simultaneously discontinue topical ocular dosing and receive treatment with standard-of-care.

The present application provides 3 dosage strengths, ranging from 0.1% to 1.0% (w/v) (as Compound-I) ophthalmic solution for clinical studies. The strengths are about 0.1%, about 0.3%, about 0.6%, and about 1.0% (w/v) Compound-I HCl.

Formulation Preparation

Non-limiting examples of formulations of the present application are outlined in Table 12.

TABLE 12

Overview of product compositions tested in product screening studies

| Cyclodextrin Type and Ratio Range[a] | Cyclodextrin Conc. Range | Compound-I Conc. | pH | Buffer type and level |
|---|---|---|---|---|
| HPβCD[b] 1:4, 1:8, 1:10, 1:12 | 6.3 to 18.9% | 0.6% | 7 | None and Tris |
| HPβCD 1:6, 1:8, 1:10 | 1.58 to 15.6% | 0.1 and 0.6% | 6 | None and Tris |
| HPβCD 1:6, 1:10 | 1.58 to 2.63% | 0.1% | 6.5, 7 | None and Tris |
| SBECD 1:2, 1:3, 1:4, 1:6, 1:8, 1:10 | 0.81 to 19.5% | 0.1 and 0.6% | 6 | Phosphate |
| SBECD[c] | 1:3 | 0.1, 0.4% | 5.5, 6.5 | Phosphate, Tris |
| HPβCD | 1:8 | 0.1, 0.4% | 5.5, 6.5 | Phosphate, Tris |

[a]Molar ratio of Compound-I: cyclodextrin.
[b]KLEPTOSE ® HPB
[c]CAPTISOL ®

EGFR Tyrosine Phosphorylation Assay in Cells to Determine EGFR Activity of Compounds of Formula I or II An EGFR tyrosine assay in corneal epithelial cells is run to determine whether higher concentrations of EGF can overcome inhibition of EGFR kinase activity. Cells are serum starved and then are pre-treated with different concentrations of a compound of Formula I or II, e.g., Compound-I or a control for followed by treatment with EGF. Cells are then harvested and immunoblotted for determination of phosphorylated EGFR and total EGFR concentration which was used to determine receptor activity ($IC_{50}$).

EGFR Tyrosine Phosphorylation Assay in Cells to Determine EGFR Activity of a Combination of Compounds of Formula I or II, and a Second Active Agent An EGFR tyrosine assay in corneal epithelial cells is run to determine if Vitamin K or nicotinic acid/nicotinamide can overcome inhibition of EGFR and if there is an increase in EGFR activity. Cells are serum starved and then are pre-treated with a different concentration of a compound of Formula I or II, e.g., Compound-I and saturating concentrations of vitamin K or nicotinic acid/nicotinamide followed by treatment with EGF. Cells are harvested cells and immunoblotted for determination of phosphorylated EGFR (tyrosine 1068 and tyrosine 1045) and total EGFR concentration which was used to determine receptor activity ($IC_{50}$).

Determination of Effects of Varying Concentrations of Compounds of Formula I or II and EGF on Cell Migration/Proliferation in Cells (In Vitro Wound Healing)

Determination of cell migration/proliferation in corneal epithelial cells is run to determine cell migration/proliferation in the presence of varying concentrations of a compound of Formula I or II and EGF. Cells are plated with silicone plugs. The cells are then serum starved and pre-treated with varying concentrations of a compound of Formula I or II or a control. The silicone plugs are then removed to create the acellular area the cells are treated with EGF. Cell migration is quantified from micrographs.

Determination Cell Migration/Proliferation in Cells Treated with Compounds of Formula I or II and/or a Second Active Agent Determination of cell migration/proliferation in corneal epithelial cells is run to determine cell migration/proliferation in the presence of varying concentrations of a compound of Formula I or II, vitamin K, or nicotinic acid/nicotinamide. Cells are plated with silicone plugs. The cells are then serum starved and pre-treated with varying concentrations of a compound of Formula I or II or a control. The plugs are removed and the cells are treated with 1) EGF, 2) EGF and vitamin K or 3) EGF and nicotinic acid/nicotinamide. Cell migration is quantified from micrographs.

Determination of Effects of Compounds of Formula I or II on Basal and EGF-Mediated Corneal Wound Healing In Vivo Determination of the effects of a compound of Formula I or II on basal and ligand stimulated rates of corneal wound healing was determined in mice. Corneas of C57/Bl mice are wounded and then pre-treated with a compound of Formula I or II followed by addition of EGF. Wound size is monitored by fluorescein staining and fluorescent photography and quantified.

Determination of Effects of Compounds of Formula I or II and a Second Active Agent on Basal and EGF-Mediated Corneal Wound Healing In Vivo Determination of the effects of a compound of Formula I or II and/or a second active agent on corneal wound healing was determined in mice. Corneas of C57/Bl mice are wounded and then pre-treated with a compound of Formula I or II, followed by addition of EGF, vitamin K, or nicotinic acid/nicotinamide. Wound size and closure are monitored.

Doses of Treatment

The formulation of the present application is effective in treating (i.e., lesion stabilization or regression) or preventing choroidal and retinal neovascularization (NV) in the eye of a mammalian subject. The Compound-I of the present application, at a specific dose, inhibits a receptor tyrosine kinase and the second active agent at a specific dose, inhibits an ErbB receptor tyrosine kinase. In some embodiments, the Compound-I formulation, at a specific dose, inhibits receptor tyrosine kinase including, VEGFR, FGFRs, Tie2, and EphB-4. The inhibition of several RTKs by the formulation of the present application, at a specific dose, simultaneously has a synergistic effect, and is effective in the treatment or regression of NV in the posterior segment of the eye. In some embodiment, the second active agent modulates (e.g., activates) directly or indirectly an ErB receptor tyrosine kinase including, EGFR, HER2, HER3 and Erb4. The activation of several ErB receptor tyrosine kinases by the formulation of the present application, at a specific dose, simultaneously may have a synergistic effect, and is effective in the prevention or treatment of corneal disruptions or diseases.

In one embodiment, the present application provides a method of treating (i.e., lesion stabilization or regression) or preventing choroidal and retinal neovascularization (NV) in the eye by administering to the subject in need thereof a therapeutically effective amount of a compound of Formula I or II, or a pharmaceutically acceptable salt thereof, and a second active agent or a pharmaceutically acceptable salt thereof, wherein a compound of Formula I or II, or a pharmaceutically acceptable salt thereof, and the second active agent, or a pharmaceutically acceptable salt thereof, are administered simultaneously. Alternatively, a compound of Formula I or II, or a pharmaceutically acceptable salt thereof, is administered prior to administration of a second active agent, or a pharmaceutically acceptable salt thereof. In another embodiment, a compound of Formula I or II, or a pharmaceutically acceptable salt thereof, is administered after administration of a second active agent, or a pharmaceutically acceptable salt thereof. In another embodiment, the present application provides a method of treating (i.e., lesion stabilization or regression) or preventing choroidal and retinal neovascularization (NV) in the eye by administering to the subject in need thereof a therapeutically effective amount of a compound of Formula I or II, or a pharmaceutically acceptable salt thereof, prior to administering a therapeutically effective dose of a formulation described herein.

In another embodiment, the present application provides a method of treating (i.e., lesion stabilization or regression) or preventing choroidal and retinal neovascularization (NV) in the eye and preventing or treating a corneal disruption or disease by administering to the subject in need thereof a therapeutically effective amount of a compound of Formula I or II, or a pharmaceutically acceptable salt thereof, and a second active agent or a pharmaceutically acceptable salt thereof, wherein a compound of Formula I or II, or a pharmaceutically acceptable salt thereof, and the second active agent, or a pharmaceutically acceptable salt thereof, are administered simultaneously. Alternatively, a compound of Formula I or II, or a pharmaceutically acceptable salt thereof, is administered prior to administration of a second active agent, or a pharmaceutically acceptable salt thereof. In another embodiment, a compound of Formula I or II, or a pharmaceutically acceptable salt thereof, is administered after administration of a second active agent, or a pharmaceutically acceptable salt thereof. In another embodiment, the present application provides a method of treating (i.e., lesion stabilization or regression) or preventing choroidal and retinal neovascularization (NV) in the eye and preventing or treating a corneal disruption or disease by administering to the subject in need thereof a therapeutically effective amount of a compound of Formula I or II, or a pharmaceutically acceptable salt thereof, prior to administering a therapeutically effective dose of a formulation described herein.

In a further embodiment, the formulation of the present application is effective in treating NV and treating and/or preventing corneal disruption or disease caused by systemic disease, an eye disease or administration of a compound of Formula I or II when administered one, two, three, and four times daily by topical ocular delivery of about 0.005%-about 5.0% (about 0.05-about 50 mg/mL) of Compound-I and a second active agent. The formulation of Compound-I or its free base (Formula II) and a second active agent, for the treatment or regression of NV and the treatment and/or regression of corneal disruption or disease, is a solution comprising a second active agent, a compound of Formula I or II, and cyclodextrin or in a suspension comprising Tris. The solution or suspension when delivered to a subject exposed to atmospheric oxygen to induce oxygen induced retinopathy (OIR) or NV, for example, is able to effectively reduce the mean area of pre-retinal NV per retina with little or no corneal disruption or disease. The prevention or treatment of NV by Compound-I formulation and/or suspension is achieved via inhibition of several receptor tyrosine kinases (RTKs), including VEGFR-2. The prevention or treatment of corneal disruptions or disease by a second active agent is achieved via moculation (e.g., activation) of EGFR.

Any of the disclosed diseases or conditions described herein can be treated or prevented by achieving target tissue concentration of from about 200 nM-about 2 µM of the disclosed compounds or pharmaceutically acceptable salts, formulation and/or suspension thereof. One embodiment of this application relates to a method for treating pathologic angiogenesis in the posterior segment of the eye, achieving target tissue concentration of about of about 200 nM-about 2 µM of the disclosed compounds or pharmaceutically acceptable salts, and/or formulation thereof. Another iteration of this embodiment relates to achieving target tissue concentration of about 300 nM-about 2 µM of one or more of the disclosed compounds or pharmaceutically acceptable salts, and/or formulation thereof.

In an embodiment of the present application about 0.2-about 1.0% (about 2-about 10 mg/mL) of Compound-I formulated as a solution or suspension, upon administration, may effectively inhibit VEGFR-2 kinase function and provide substantial blockade of a set of proangiogenic growth factor receptors, including FGFRs1-3, Tie-2, and EphB-4. The 2-10 mg/mL concentration of the Compound-I in the formulation provides effective pharmacologically effective concentrations of drug to the central choroid and retina following 1-5 days of topical ocular delivery.

In some embodiments, the exposure time of Compound-I is between 1 and 90 days or for longer than 90 days (e.g., 4 months, 6 months, 8 months, or 12 months). In some embodiments, the dosage regimen involves several courses of topical ocular administration of a formulation comprising Compound-I to a subject for between 1 and 90 days or for longer than 90 days (e.g., 4 months, 6 months, 8 months, or 12 months). For example, the dosage regimen involves once daily, twice daily, three times daily or four times daily administration of the formulation for between 1 and 90 days or for longer than 90 days (e.g., 4 months, 6 months, 8 months, or 12 months). For example, the dosage regimen involves once, twice, three times, or four times administration of the formulation on every other day (i.e., on day 1, 3, 5, 7 etc.) for up to 90 days. For example, the dosage regimen involves administering once on day 1, once or twice on day 2-day 90. For example, the dosage regimen involves administering once, twice, three times, or four times on day 1, followed by once daily for 2-90 days. For example, the dosage regimen involves administering once, twice, three times, four times on day 1, followed by once, twice, three times, or four times on every other day (i.e., on day 1, 3, 5, 7 etc.) for up to 90 days. For example, one dosage regimen involves once per day or twice per day for 1, 2, 3, 4, or 5 consecutive days. For twice or three daily dosage regimen, subjects receive topical ocular dose of a Compound-I formulation on days 1 and 4 approximately about 4, 6, or 8 hours apart. In another embodiment, subjects receive topical ocular doses of a Compound-I formulation approximately about 4, 6, or 8 hours apart for four consecutive days. In some embodiments, subjects receive one or two doses of topical ocular dose of Compound-I formulation per day for 5 consecutive days. In yet other embodiments, subjects receive one or two doses of topical ocular dose of Compound-I formulation for 5-90 consecutive days. In some embodiments, subjects receive one or two doses of topical ocular dose of Compound-I formulation for at least 25 consecutive days. In one embodiment, subjects receive one or two topical ocular doses for at least 90 consecutive days or more.

In some embodiments, the present application provides a formulation of Compound-I or its free base and/or a second active agent administered topically to the anterior segment of the eye of the subject to treat AMD, pathologic CNV, and/or pathologic NV. For example, the formulation is administered to the eye of a subject 1, 2, 3, or 4 times daily. In specific embodiments, the formulation is administered to the eye of a subject 2 or 3 times daily. For example, the formulation is administered to one eye or both eyes of a subject. For example, about 1 mg/ml of a first active agent comprising formulation of the current disclosure is administered twice a day (BID) to one eye or both eyes of a subject. In some embodiments, about 1 mg/mL once a day (QD) or BID, about 2 mg/mL QD or BID, about 3 mg/mL QD or BID, about 4 mg/mL QD or BID, about 5 mg/mL QD or BID, about 6 mg/mL QD or BID, about 7 mg/mL QD or BID, about 8 mg/mL QD or BID, about 9 mg/mL QD or BID, or about 10 mg/mL QD or BID of is administered to one eye or both eyes of a subject.

For example, a formulation comprising about 1 mg/mL BID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 1 mg/mL QD of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 1 mg/mL TID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 1 mg/mL QID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 2 mg/mL BID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 2 mg/mL QD of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 2 mg/mL TID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 2 mg/mL QID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 3 mg/mL BID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 3 mg/mL QD of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 3 mg/mL TID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 3 mg/mL QID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 4 mg/mL BID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 4 mg/mL QD of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 4 mg/mL TID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 4 mg/mL QID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 5 mg/mL BID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 5 mg/mL QD of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 5 mg/mL TID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 5 mg/mL QID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 6 mg/mL BID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 6 mg/mL QD of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 6 mg/mL TID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 6 mg/mL QID of Compound-I and/or a second active agent is administered to one eye or both eyes of a subject for between 1 and 90 days or for longer than 90 days (e.g., 4 months, 6 months, 8 months, or 12 months). In some embodiments a formulation comprising about 7 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 7 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 7 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 7 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 8 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 8 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 8 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 8 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 9 mg/mL BID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 9 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 9 mg/mL TID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 9 mg/mL QID of a first active agent (e.g., Compound-I) and a second active agent is administered to one eye or both eyes of a subject for between 1 and 90 days or for longer than 90 days (e.g., 4 months, 6 months, 8 months, or 12 months). In some embodiments a formulation comprising about 10 mg/mL QD of a first active agent (e.g., Compound-I) and a second active agent is administered to one eye or both eyes of a subject for between 1 and 90 days or for longer than 90 days (e.g., 4 months, 6 months, 8 months, or 12 months). The dosage regimen for between 1 and 90 days or for longer than 90 days (e.g., 4 months, 6 months, 8 months, or 12 months) may be any of the regimens involving consecutive or alternate days described in the paragraph above. In some embodiments, the formulation of the present application is administered QD, BID, TID, or QID when administered at low doses (e.g., 1 mg/mL, 2 mg/mL, 3 mg/mL, 4 mg/mL, or 5 mg/mL), and QD or BID at high doses (e.g., 6 mg/mL, 7 mg/mL, 8 mg/mL, 9 mg/mL, or 10 mg/mL).

In other embodiment, a 1 mg/mL BID of Compound-I formulation and a second active agent is administered to one eye or both eyes of a subject for between 1 and 90 days or for longer than 90 days (e.g., 4 months, 6 months, 8 months, or 12 months). In some embodiments, a 1 mg/mL QD of Compound-I formulation and a second active agent is administered to one eye or both eyes of a subject for between 1 and 90 days or for longer than 90 days (e.g., 4 months, 6 months, 8 months, or 12 months). In some embodiments, a 2 mg/mL BID of Compound-I formulation and a second active agent is administered to one eye or both eyes of a subject for between 1 and 90 days or for longer than 90 days (e.g., 4 months, 6 months, 8 months, or 12 months). In some embodiments, a 2 mg/mL QD of Compound-I formulation and a second active agent is administered to one eye or both eyes of a subject for between 1 and 90 days or for longer than 90 days (e.g., 4 months, 6 months, 8 months, or 12 months). In some embodiments, a 3 mg/mL BID of Compound-I formulation and a second active agent is administered to one eye or both eyes of a subject for between 1 and 90 days or for longer than 90 days (e.g., 4 months, 6 months, 8 months, or 12 months). In some embodiments, a 3 mg/mL QD of Compound-I formulation and a second active agent is administered to one eye or both eyes of a subject for between 1 and 90 days or for longer than 90 days (e.g., 4 months, 6 months, 8 months, or 12 months). In some embodiments a 4 mg/mL BID of Compound-I formulation and a second active agent is administered to one eye or both eyes of a subject for between 1 and 90 days or for longer than 90 days (e.g., 4 months, 6 months, 8 months, or 12 months). In some embodiments, a 4 mg/mL QD of Compound-I formulation and a second active agent is administered to one eye or both eyes of a subject for between 1 and 90 days or for longer than 90 days (e.g., 4 months, 6 months, 8 months, or 12 months). In some embodiments, a 5 mg/mL BID of Compound-I formulation and a second active agent is administered to one eye or both eyes of a subject for between 1 and 90 days or for longer than 90 days (e.g., 4 months, 6 months, 8 months, or 12 months). In some embodiments a 5 mg/mL QD of Compound-I formulation and a second active agent is administered to one eye or both eyes of a subject for between 1 and 90 days or for longer than 90 days (e.g., 4 months, 6 months, 8 months, or 12 months). In some embodiments, a 6 mg/mL BID of Compound-I formulation and a second active agent is administered to one eye or both eyes of a subject for between 1 and 90 days or for longer than 90 days (e.g., 4 months, 6 months, 8 months, or 12 months). In some embodiments, a 6 mg/mL QD of Compound-I formulation and a second active agent is administered to one eye or both eyes of a subject for between 1 and 90 days or for longer than 90 days (e.g., 4 months, 6 months, 8 months, or 12 months). In some embodiments, a 7 mg/mL BID of Compound-I formulation and a second active agent is administered to one eye or both eyes of a subject for between 1 and 90 days or for longer than 90 days (e.g., 4 months, 6 months, 8 months, or 12 months). In some embodiments, a 7 mg/mL QD of Compound-I formulation and a second active agent is administered to one eye or both eyes of a subject for between 1 and 90 days or for longer than 90 days (e.g., 4 months, 6 months, 8 months, or 12 months). In some embodiments, a 8 mg/mL BID of Compound-I formulation and a second active agent is administered to one eye or both eyes of a subject for between 1 and 90 days or for longer than 90 days (e.g., 4 months, 6 months, 8 months, or 12 months). In some embodiments, a 8 mg/mL QD of Compound-I formulation and a second active agent is administered to one eye or both eyes of a subject for between 1 and 90 days or for longer than 90 days (e.g., 4 months, 6 months, 8 months, or 12 months). In some embodiments, a 9 mg/mL BID of Compound-I formulation and a second active agent is administered to one eye or both eyes of a subject for between 1 and 90 days or for longer than 90 days (e.g., 4 months, 6 months, 8 months, or 12 months). In some embodiments, a 9 mg/mL QD of Compound-I formulation and a second active agent is administered to one eye or both eyes of a subject for between 1 and 90 days or for longer than 90 days (e.g., 4 months, 6 months, 8 months, or 12 months). In some embodiments, a 10 mg/mL BID of Compound-I formulation and a second active agent is administered to one eye or both eyes of a subject for between 1 and 90 days or for longer than 90 days (e.g., 4 months, 6 months, 8 months, or 12 months). In some embodiments, a 10 mg/mL QD of Compound-I formulation and a second active agent is administered to one eye or both eyes of a subject for between 1 and 90 days or for longer than 90 days (e.g., 4 months, 6 months, 8 months, or 12 months). The dosage regimen for between 1 and 90 days or for longer than 90 days (e.g., 4 months, 6 months, 8 months, or 12 months) may be any of the regimens involving consecutive or alternate days described in the paragraph above.

The present application provides formulations as shown in Table 13 for administering to one eye or both eyes of a subject.

TABLE 13

| Dose/Day | Formula II (%) | Compound-I (%) | Formula II/Compound-I:CD | KLEPTOSE® HPB (%) | 10 mM Phosphate (%) | Sodium Chloride (%)* | pH |
|---|---|---|---|---|---|---|---|
| QD | 0.40 | 0.427 | 1:8 | 8.411 | 0.142 | QS to about 285 mOsm | 6 |
| QD | 0.60 | 0.641 | 1:8 | 12.626 | 0.142 | QS to about 285 mOsm | 6 |
| BID | 0.10 | 0.107 | 1:8 | 2.103 | 0.142 | QS to about 285 mOsm | 6 |
| BID | 0.20 | 0.214 | 1:8 | 4.205 | 0.142 | QS to about 285 mOsm | 6 |
| BID | 0.30 | 0.321 | 1:8 | 6.308 | 0.142 | QS to about 285 mOsm | 6 |
| BID | 0.40 | 0.427 | 1:8 | 8.411 | 0.142 | QS to about 285 mOsm | 6 |

*QS = quantity sufficient for achieving the osmolality

In some embodiments, the formulation of Formula II or Compound-I is administered to one eye or both eyes of a subject. For example, about 0.2%-about 1.0% (w/v) of the compound of Formula II or about 0.1%-1.2% (w/v) of Compound-I comprising formulation of the current disclosure is administered once a day (QD) or twice a day (BID) to one eye or both eyes of a subject for between 1 and 90 days or for longer than 90 days (e.g., 4 months, 6 months, 8 months, or 12 months). In some embodiments, Formula II compound or Compound-I is complexed with a complexing agent, e.g., cyclodextrin (e.g., KLEPTOSE® HPB (%)) in ratio of about 1:8, in which about 2%-13% (w/v) cyclodextrin (e.g., KLEPTOSE® HPB (%)) is added to the formulation. The formulation further comprises about 0.1%-about 0.2% buffer, e.g., 10 mM phosphate buffer. The desired osmolality of the formulation is about 200-about 300 mOsm, achieved by adding quantity sufficient to achieve the osmolality with a salt, e.g., sodium chloride. The pH of the formulation is about 6.0 at or under about 40° C. The dosage regimen for between 1 and 90 days or for longer than 90 days (e.g., 4 months, 6 months, 8 months, or 12 months) may be any of the regimens involving consecutive or alternate days described in the paragraph above.

In some embodiments, the Formula II compound or Compound-I formulation further comprises a second active agent. In some embodiment, Formula II compound or Compound-I formulation is administered with a second active agent. The second active agent, e.g., nicotinic acid, nicotinamide, or vitamin K or a combination thereof, at a specific dose modulates (e.g., activates) directly or indirectly, ErbB receptor tyrosine kinase (RTK) including, EGFR, HER2, HER3, and HER4. The modulation (e.g., activation) of one or more ErbB RTKs by the formulation of the present application, at a specific dose, simultaneous and has a synergistic effect, and is effective in the prevention or treatment of corneal disruptions or diseases, (e.g., corneal ulcers, corneal epithelial defects, keratitis, etc.) in the anterior segment of the eye.

The methods of the present application are combined with the standard of care, including but not limited to laser treatment and treatment with injectable anti-neovascular agents.

Particle Compositions and Formulations Comprising the Particle Compositions

The present application relates to a pharmaceutical composition comprising particles of an active agent of the present application (e.g., a first active agent (e.g., Formula II or Compound-I) and/or a second active agent), or a pharmaceutically acceptable salt thereof, wherein the particles have a mean diameter of between 100 nm and 100 μm. In some embodiments, the particles have a mean diameter of between 20 μm and 90 μm. In some embodiments, the particles have a mean diameter of between 20 μm and 80 μm. In some embodiments, the particles have a mean diameter of between 20 μm and 70 μm. In some embodiments, the particles have a mean diameter of between 30 μm and 70 μm. In some embodiments, the particles have a mean diameter of between 30 μm and 60 μm. In some embodiments, the particles have a mean diameter of between 30 μm and 50 μm. In some embodiments, the particles have a mean diameter of between 30 μm and 40 μm. In some embodiments, the particles have a mean diameter of between 50 μm and 70 μm. In some embodiments, the particles have a mean diameter of between 50 μm and 60 μm. In some embodiments, the particles have a mean diameter of at least 30 μm. In some embodiments, the particles have a mean diameter of about 30 μm, about 35 μm, about 40 μm, about 45 μm, about 50 μm, about 55 μm, about 60 μm, about 65 μm, or about 70 μm. In some embodiments, the particles have a mean diameter of about 30 μm, about 35 μm, about 50 μm, or about 60 μm. In some embodiments, the particles have a mean diameter of between 100 nm and 8 μm. In some embodiments, the particles have a mean diameter of between 100 nm and 200 nm. In some embodiments, the particles have a mean diameter of at most 150 nm. In some embodiments, the particles have a mean diameter of about 150 nm, about 140 nm, about 130 nm, about 120 nm, about 110 nm, or about 100 nm. In other embodiments, the particles have a mean diameter of between 1 μm and 5 μm. In some embodiments, the particles have a mean diameter of between 2 μm and 4 μm. In some embodiments, the particles have a mean diameter of about 1 μm, about 2 μm, about 3 μm, about 4 μm, or about 5 μm. In some embodiments, the particles have a mean diameter of about 3 μm.

In some embodiments, at least 90% of the particles have a diameter of 70 μm or less. In some embodiments, at least 90% of the particles have a diameter of 60 μm or less. In some embodiments, at least 90% of the particles have a diameter of 10 μm or less. In some embodiments, at least 90% of the particles have a diameter of 9 μm or less. In some embodiments, at least 90% of the particles have a diameter of 8 μm or less. In some embodiments, at least 90% of the particles have a diameter of 7 μm or less. In some embodiments, at least 90% of the particles have a diameter of 6 μm or less. In some embodiments, at least 90% of the particles have a diameter of 5 μm or less. In some embodiments, at least 90% of the particles have a diameter of 4 μm or less. In some embodiments, at least 90% of the particles have a diameter of 300 nm or less. In some embodiments, at least 90% of the particles have a diameter of 200 nm or less.

In some embodiments, the pharmaceutical composition comprises particles of a first active agent (e.g., a first active agent (e.g., Formula II or Compound-I)) and particles of a second active agent (e.g., nicotinic acid, nicotinamide, vitamin K, or a combination thereof). In some embodiments, the pharmaceutical composition comprises particles of a first active agent (e.g., a first active agent (e.g., Formula II or Compound-I)) and particles of vitamin K (e.g., menadione).

In some embodiments, a first active agent (e.g., Formula II or Compound-I) and a second active agent (e.g., nicotinic acid, nicotinamide, vitamin K, or a combination thereof) are roller milled together to form particles comprising the first active agent and the second active agent. In some embodiments, the first active agent and the second active agent are roller milled separately, and the particles comprising the first active agent and the particles comprising the second active agent are then mixed or roller milled together. In some embodiments, the first active agent or the second active agent is roller milled first, and the particles are then added to the other active agent for further roller milling.

In some embodiments, the pharmaceutical composition comprising particles of an active agent of the present application (e.g., a first active agent or a second active agent) further comprises one or more excipients. The excipient can be selected from any suitable excipient known in the art, for example, for preparing an ophthalmic formulation. In some embodiments, the excipient is selected from Polysorbate (Tween) 80, Poloxamer (Pluronic) F-127, Hypromellose (Hydroxypropyl Methylcellulose or HPMC), Povidone (PVP K-29/32 or K-30), and Tyloxapol, and a combination thereof. In some embodiments, the excipient is selected from HPMC, Tween 80, Pluronic F-127, and Tyloxapol, and a combination thereof.

In some embodiments, the particles comprising a first active agent (e.g., Formula II or Compound-I) and the particles comprising a second active agent (e.g., nicotinic acid, nicotinamide, vitamin K, or a combination thereof) comprise the same excipient(s).

In some embodiments, the pharmaceutical composition comprising particles of an active agent of the present application (e.g., a first active agent or a second active agent) further comprises a surfactant, such as benzalkonium chloride (BAC).

In some embodiments, the pharmaceutical composition comprising particles of an active agent of the present application (e.g., a first active agent or a second active agent) further comprises an excipient (e.g., for enhancing bioavailability of the active agent). In some embodiments, the excipient is hydroxyethyl cellulose (HEC). In some embodiments, the HEC is present in an amount of about 0.1%-about 1%, about 0.1%-about 0.9%, about 0.1%-about 0.8%, about 0.1%-about 0.7%, about 0.1%-about 0.6%, about 0.1%-about 0.5%, about 0.1%-about 0.4%, or about 0.1%-about 0.3%. In some embodiments, the HEC is present in an amount of about 0.2% or about 0.3%.

In some embodiments, the particles of the present application comprise Formula II (i.e., free base of Compound-I). In other embodiments, the particles of the present application comprises Compound-I.

In some embodiments, the particles of the present application are prepared by roller milling. Factors that may affect the size of the particles include, but are not limited to, the use of the free base or a salt of the active agent (e.g., Compound-I vs. Formula II), the addition of an excipient, the speed of the roller during milling, the size of the milling media, and duration of the milling.

In some embodiments, the particles of the present application are prepared without roller milling.

In some embodiments, the particles of an active agent of the present application (e.g., a first active agent (e.g., Formula II or Compound-I) and/or a second active agent) are sterilized. In some embodiments, the sterilization is conducted with gamma irradiation. In some embodiments, the particles of an active agent of the present application (e.g., a first active agent (e.g., Formula II or Compound-I) and/or a second active agent) are stable after the sterilization (e.g., remaining substantially pure of any impurities or degradation products as a result of the sterilization).

The present application relates to a suspension formulation comprising a pharmaceutical composition, wherein the pharmaceutical composition comprises particles of an active agent of the present application (e.g., a first active agent (e.g., Formula II or Compound-I) and/or a second active agent), or a pharmaceutically acceptable salt thereof, as described herein.

In some embodiments, the suspension formulation comprises particles of a first active agent (e.g., Formula II or Compound-I), wherein the first active agent is at a concentration of about 0.1 mg/mL-about 10 mg/mL. In some embodiments, the first active agent is at a concentration of about 0.2 mg/mL-about 10 mg/mL, about 0.5 mg/mL-about 10 mg/mL, about 1 mg/mL-about 10 mg/mL, about 2 mg/mL-about 9 mg/mL, about 2 mg/mL-about 8 mg/mL, about 3 mg/mL-about 8 mg/mL, about 3 mg/mL-about 7 mg/mL, about 3 mg/mL-about 6 mg/mL, about 4 mg/mL-about 6 mg/mL, or about 4 mg/mL-about 5 mg/mL of a first active agent (e.g., Formula II or Compound-I). In some embodiments, the first active agent is at a concentration of about 0.1 mg/mL, 0.3 mg/mL, 0.5 mg/mL, about 1 mg/mL, about 2 mg/mL, about 3 mg/mL, about 4 mg/mL, about 6 mg/mL, or about 10 mg/mL. In some embodiments, the first active agent is at a concentration of about 1 mg/mL-about 4 mg/mL or about 2 mg/mL-about 4 mg/mL. In some embodiments, the first active agent is at a concentration of about 2 mg/mL or about 4 mg/mL.

In some embodiments, the suspension formulation comprising particles of a first active agent (e.g., Formula II or Compound-I) further comprises a second active agent (e.g., nicotinic acid, nicotinamide, vitamin K, or a combination thereof). In some embodiments, the second active agent is vitamin K (e.g., menadione). In some embodiments, the second active agent is present in an amount of less than 10 µM. In some embodiments, the second active agent is present in an amount of about 0.5 µM, about 0.6 µM, about 0.7 µM, about 0.8 µM, about 0.9 µM, about 1 µM, about 2 µM, about 3 µM, about 4 µM, about 5 µM, about 6 µM, about 7 µM, about 8 µM, or about 9 µM. In some embodiments, the second active agent is present in an amount of about 1 µM.

In some embodiments, the suspension formulation comprising particles of a first active agent (e.g., Formula II or Compound-I) further comprises an excipient selected from Polysorbate (Tween) 80, Poloxamer (Pluronic) F-127, Hypromellose (Hydroxypropyl Methylcellulose or HPMC), Povidone (PVP K-29/32 or K-30), and Tyloxapol, and a combination thereof. In some embodiments, the excipient is Pluronic F-127, Tween 80, HPMC, or Tyloxapol, or a combination thereof. In some embodiments, the excipient is present in a concentration of about 0.01%-about 0.2%, about 0.01%-about 0.15%, about 0.01%-about 0.12%, about 0.01%-about 0.1%, about 0.01%-about 0.09%, about 0.02%-about 0.09%, about 0.03%-about 0.09%, about 0.04%-about 0.09%, or about 0.04%-about 0.08%. In some embodiments, the suspension formulation comprises about 0.08% or about 0.04% Pluronic F-127. In some embodiments, the suspension formulation comprises about 0.08% HPMC. In other embodiments, the suspension formulation comprises about 0.04% Tyloxapol.

In some embodiments, the suspension formulation comprising particles of a first active agent (e.g., Formula II or Compound-I) further comprises a buffering agent. In some embodiments, the buffering agent is selected from phosphate buffers, borate buffers, citrate buffers, tartrate buffers, acetate buffers, amino acids, sodium acetate, sodium citrate, Tris buffers, and the like. In some embodiments, the buffering agent is Tris. In some embodiments, the buffering agent is present in a concentration of about 0.1%-about 2%, about 0.2%-about 1.8%, about 0.3%-about 1.6%, about 0.4%-about 1.4%, about 0.4%-about 1.2%, about 0.4%-about 1%, about 0.4%-about 0.8%, about 0.4%-about 0.7%, or about 0.5%-about 0.7%. In some embodiments, the suspension formulation comprises about 0.6% Tris.

In some embodiments, the suspension formulation comprising particles of a first active agent (e.g., Formula II or Compound-I) further comprises an osmolality adjusting reagent. In some embodiments, the osmolality adjusting reagent is glycerol. In some embodiments, the osmolality adjusting reagent is present in an amount of about 1%-about 10%, about 2%-about 10%, about 3%-about 10%, about 4%-about 10%, about 5%-about 10%, about 2%-about 9%, about 2%-about 8%, about 2%-about 7%, about 2%-about 6%, about 2%-about 5%, about 2%-about 4%, or about 2%-about 3%. In some embodiments, the suspension formulation comprises about 2% or about 2.5% glycerol.

In some embodiments, the suspension formulation comprising particles of a first active agent (e.g., Formula II or Compound-I) has a pH of less than 7.5. In some embodiments the pH is between about 6.0-about 7.0. In some embodiments the pH is about 6.0 or about 7.0.

In some embodiments, the suspension formulation comprising particles of a first active agent (e.g., Formula II or Compound-I) further comprises hydroxyethyl cellulose (HEC). In some embodiments, the HEC is present in an amount of about 0.1%-about 1%, about 0.1%-about 0.9%, about 0.1%-about 0.8%, about 0.1%-about 0.7%, about 0.1%-about 0.6%, about 0.1%-about 0.5%, about 0.1%-about 0.4%, or about 0.1%-about 0.3%. In some embodiments, the HEC is present in an amount of about 0.2% or about 0.3%.

One of a first active agent, a second active agent, and one or more excipients described in the present application can be present at any concentration or level described herein in combination with the remainder of the first active agent, the second active agent, and one or more excipients described in the present application at any concentration or level described herein.

In some embodiments, the formulation of the present application comprises a first active agent at about 0.1% to about 1.2% (or any range in between as described herein), Tris at about 0.4%-about 0.8% (or any range in between as described herein), glycerol at about 2%-about 4% (or any range in between as described herein), HEC at about 0.1%-about 0.3% (or any range in between as described herein), and HPMC at about 0.04%-about 0.09% (or any range in between as described herein). In some embodiments, the first active agent is Formula II or Compound-I. In some embodiments, the formulation of the present application comprises Formula II or Compound-I at about 0.4%, Tris at about 0.6%, glycerol at about 2%, HEC at about 0.2%, and HPMC at about 0.08%. In some embodiments, the formulation comprises particles of the first active agent wherein the particles have a mean diameter of between 30 μm and 60 μm. In some embodiments, the formulation comprises particles of the first active agent wherein the particles have a mean diameter of between 50 m and 60 μm. In some embodiments, the formulation comprises particles of the first active agent wherein the particles have a mean diameter of about 50 μm or 60 μm. In some embodiments, the formulation has a pH of less than 7.0. In some embodiments, the formulation has a pH of about 6.

In some embodiments, the formulation of the present application comprises a first active agent at about 0.1% to about 1.2% (or any range in between as described herein), a second active agent at about 0.00001%-about 0.0001% (or any range in between as described herein), Tris at about 0.4%-about 0.8% (or any range in between as described herein), glycerol at about 2%-about 4% (or any range in between as described herein), HEC at about 0.1%-about 0.3% (or any range in between as described herein), and HPMC at about 0.04%-about 0.09% (or any range in between as described herein). In some embodiments, the first active agent is Formula II or Compound-I. In some embodiments, the second active agent is vitamin $K_3$ (e.g., menadione). In some embodiments, the formulation of the present application comprises Formula II or Compound-I at about 0.4%, vitamin $K_3$ at about 0.000086%, Tris at about 0.6%, glycerol at about 2%, HEC at about 0.2%, and HPMC at about 0.08%. In some embodiments, the formulation comprises particles of the first active agent wherein the particles have a mean diameter of between 30 μm and 60 μm. In some embodiments, the formulation comprises particles of the first active agent wherein the particles have a mean diameter of between 50 μm and 60 μm. In some embodiments, the formulation comprises particles of the first active agent wherein the particles have a mean diameter of about 50 μm or 60 μm. In some embodiments, the particle also comprises the second active agent. In some embodiments, the formulation has a pH of less than 7.0. In some embodiments, the formulation has a pH of about 6.

Indications and Methods of Treatment

Disclosed are methods for the treatment of diseases or conditions of the eye. The disclosed methods relate to treating, preventing, or controlling ocular neovascularization (NV), or treating a disease or condition that is related to the onset of NV by administering to a subject one or more of the disclosed compounds (e.g., a first active agent (e.g., a compound of Formula I or II), and optionally a second active agent), and formulations thereof.

One aspect of the disclosed method relates to treating or preventing NV by administering to a subject an effective amount of one or more of the disclosed compounds of Formula I or II, or pharmaceutically acceptable salts, and optionally a second active agent (e.g., vitamin K, nicotinic acid, or nicotinamide, or a combination thereof), and/or formulations thereof. One embodiment of this aspect relates to a method for treating NV by administering to a subject a composition of: a) an effective amount of one or more of the disclosed compounds of Formula I or II, or pharmaceutically acceptable salts, and optionally a second active agent (e.g., vitamin K, nicotinic acid, or nicotinamide, or a combination thereof), and/or formulations thereof, and optionally b) one or more carriers or compatible excipients.

The disclosed methods relate to preventing or controlling pathologic ocular neovascularization (NV), or treating a disease or condition that is related to the onset of NV by administering to a subject one or more of the disclosed compounds of Formula I or II, and optionally a second active agent (e.g., vitamin K, nicotinic acid, or nicotinamide, or a combination thereof), and formulations thereof.

The current embodiments provide use of a formulation of Compound-I or its free base (Formula II), and optionally a second active agent (e.g., vitamin K, nicotinic acid, or nicotinamide, or a combination thereof), for the manufacture of a medicament for treating a subject with a posterior segment disease vasculopathic or inflammatory disease of the eye. These include for example, diabetic retinopathy (including background diabetic retinopathy, proliferative diabetic retinopathy and diabetic macular edema); age-related macular degeneration (AMD) (including neovascular (wet/exudative) AMD, dry AMD, and Geographic Atrophy); pathologic choroidal neovascularization (CNV) from any mechanism (i.e. high myopia, trauma, sickle cell disease; ocular histoplasmosis, angioid streaks, traumatic choroidal rupture, drusen of the optic nerve, and some retinal dystrophies); pathologic retinal neovascularization from any mechanism (i.e., sickle cell retinopathy, Eales disease, ocular ischemic syndrome, carotid cavernous fistula, familial exudative vitreoretinopathy, hyperviscosity syndrome, idiopathic occlusive arteriolitis; birdshot retinochoroidopathy, retinal vasculitis, sarcoidosis, or toxoplasmosis); uveitis; retinal vein occlusion (central or branch); ocular trauma; surgery induced edema; surgery induced neovascularization; cystoid macular edema; ocular ischemia; retinopathy of prematurity; Coat's disease; sickle cell retinopathy and/or neovascular glaucoma. In one embodiment, the disease of the eye is AMD. In one embodiment, the diseases of the eye arise from or are exacerbated by ocular angiogenesis and/or neovascularization.

In one aspect of the present application the formulation is used in the treatment of age-related macular degeneration (AMD) (including neovascular (wet/exudative) AMD, dry AMD, and Geographic Atrophy). The solutions or suspensions are used in the treatment of neovascular (exudative or wet) AMD. In another embodiment, the solutions or suspensions are used to treat dry AMD. In yet another embodiment, the solutions or suspensions are used to treat Geographic Atrophy.

The formulation of the present application prevents, delays, or treats the onset of pathologic choroidal neovascularization (CNV) from any mechanism (i.e. high myopia, trauma, sickle cell disease; ocular histoplasmosis, angioid streaks, traumatic choroidal rupture, drusen of the optic nerve, and some retinal dystrophies) in subjects.

The formulation of the present application delays onset, prevents progression, or treats formation of pathological choroidal neovascularization (CNV) below the neurosensory retina. The formulation of the present application is effective in treating CNV.

One aspect of this method relates to treating or preventing ocular neovascularization by administering to a subject an effective amount of one or more of the disclosed compounds of Formula I or II, or pharmaceutically acceptable salts thereof, and optionally a second active agent (e.g., vitamin K, nicotinic acid, or nicotinamide, or a combination thereof). One embodiment of this aspect relates to a method for treating ocular edema and neovascularization by administering to a subject a composition of: a) an effective amount of one or more of the disclosed compounds of Formula I or II, or pharmaceutically acceptable salts, and optionally a second active agent (e.g., vitamin K, nicotinic acid, or nicotinamide, or a combination thereof), and/or formulations thereof, and optionally b) one or more carriers or compatible excipients.

The disclosed methods also relate to preventing or controlling ocular edema or treating a disease or condition that is related to the onset of ocular edema by administering to a subject one or more or the disclosed compounds of Formula I or II and optionally a second active agent (e.g., vitamin K, nicotinic acid, or nicotinamide, or a combination thereof).

One aspect of this method relates to treating or preventing ocular edema by administering to a subject an effective amount of one or more of the disclosed compounds of Formula I or II, or pharmaceutically acceptable salts thereof, and optionally a second active agent (e.g., vitamin K, nicotinic acid, or nicotinamide, or a combination thereof). One embodiment of this aspect relates to a method for treating ocular edema by administering to a subject a composition of: a) an effective amount of one or more of the disclosed compounds of Formula I or II, or pharmaceutically acceptable salts, and optionally a second active agent (e.g., vitamin K, nicotinic acid, or nicotinamide, or a combination thereof), and/or formulations thereof, and optionally b) one or more carriers or compatible excipients.

Another disclosed method relates to preventing or controlling retinal edema or retinal neovascularization or treating a disease or condition that is related to the onset of retinal edema or retinal neovascularization by administering to a subject one or more or the disclosed compounds of Formula I or II and optionally a second active agent (e.g., vitamin K, nicotinic acid, or nicotinamide, or a combination thereof). One aspect of this method relates to treating or preventing retinal edema or retinal neovascularization by administering to a subject an effective amount of one or more of the disclosed compounds of Formula I or II, or pharmaceutically acceptable salts thereof, and optionally a second active agent (e.g., vitamin K, nicotinic acid, or nicotinamide, or a combination thereof). One embodiment of this aspect relates to a method for treating retinal edema or retinal neovascularization by administering to a subject a composition of: a) an effective amount of one or more of the disclosed compounds of Formula I or II, or pharmaceutically acceptable salts, and optionally a second active agent (e.g., vitamin K, nicotinic acid, or nicotinamide, or a combination thereof), and/or formulations thereof, and optionally b) one or more carriers or compatible excipients.

Another embodiment of this aspect relates to a method for delaying or preventing progression of non-proliferative retinopathy to proliferative retinopathy by administering to a subject a composition of: a) an effective amount of one or more of the disclosed compounds of Formula I or II, or pharmaceutically acceptable salts, and optionally a second active agent (e.g., vitamin K, nicotinic acid, or nicotinamide, or a combination thereof), and/or formulations thereof, and optionally b) one or more carriers or compatible excipients.

One aspect of the disclosed methods relates to diseases that are a direct or indirect result of diabetes, inter alia, diabetic macular edema and diabetic retinopathy. The ocular vasculature of the diabetic becomes unstable over time leading to conditions such as non-proliferative retinopathy, macular edema, and proliferative retinopathy. As fluid leaks into the center of the macula, the part of the eye where sharp, straight-ahead vision occurs, the buildup of fluid and the associated protein begin to deposit on or under the macula. This results in swelling that causes the subject's central vision to gradually become distorted. This condition is referred to as "macular edema." Another condition that may occur is non-proliferative retinopathy in which vascular changes, such as microaneurysms, outside the macular region of the eye may be observed. During proliferative DR, pathologic new blood vessels grow in and up from the retina into to the vitreous body, where these abnormal vessels may alter retinal morphology in the macula, and/or hemorrhage into the vitreous and obscure the visual axis.

A further disclosed method relates to treating, preventing or controlling diabetic retinopathy or treating a disease or condition that is related to the onset of diabetic retinopathy by administering to a subject one or more or the disclosed compounds of Formula I or II, and optionally a second active agent (e.g., vitamin K, nicotinic acid, or nicotinamide, or a combination thereof).

One aspect of the disclosed method relates to treating or preventing diabetic retinopathy by administering to a subject an effective amount of one or more of the disclosed compounds of Formula I or II, or pharmaceutically acceptable salts thereof, and optionally a second active agent (e.g., vitamin K, nicotinic acid, or nicotinamide, or a combination thereof). One embodiment of this aspect relates to a method for treating diabetic retinopathy by administering to a subject a composition of: a) an effective amount of one or more of the disclosed compounds of Formula I or II, or pharmaceutically acceptable salts, and optionally a second active agent (e.g., vitamin K, nicotinic acid, or nicotinamide, or a combination thereof), and/or formulations thereof, and optionally b) one or more carriers or compatible excipients.

Diabetic proliferative retinopathy is characterized by neovascularization. The new blood vessels are fragile and are susceptible to bleeding. The result is scarring of the retina, as well as occlusion or total blockage of the light pathway through the eye due to the abnormal formation of new blood vessels. Typically subjects having diabetic macular edema are suffering from the non-proliferative stage of diabetic retinopathy; however, it is not uncommon for subjects to only begin manifesting macular edema at the onset of the proliferative stage.

Yet a further disclosed method relates to preventing or controlling diabetic macular edema or treating a disease or condition that is related to the onset of diabetic macular edema by administering to a subject one or more or the disclosed compounds of Formula I or II and optionally a second active agent (e.g., vitamin K, nicotinic acid, or nicotinamide, or a combination thereof).

One aspect of this method relates to treating or preventing diabetic macular edema by administering to a subject an effective amount of one or more of the disclosed compounds of Formula I or II, or pharmaceutically acceptable salts, and optionally a second active agent (e.g., vitamin K, nicotinic acid, or nicotinamide, or a combination thereof), or formulations thereof. One embodiment of this aspect relates to a method for treating diabetic macular edema by administering to a subject a composition of: a) an effective amount of one or more of the disclosed compounds of Formula I or II, or pharmaceutically acceptable salts, and optionally a second active agent (e.g., vitamin K, nicotinic acid, or nicotinamide, or a combination thereof), and/or formulations thereof, and b) one or more carriers or compatible excipients.

Another aspect of the disclosed method relates to treating or preventing NV and treating and/or preventing corneal disruptions or diseases by administering to a subject an effective amount of one or more of the disclosed compounds of Formula I or II, or pharmaceutically acceptable salts, a second active agent, and/or formulations thereof. One embodiment of this aspect relates to a method for treating NV and treating and/or preventing corneal disruptions or diseases by administering to a subject a composition of: a) an effective amount of one or more of the disclosed compounds of Formula I or II, or pharmaceutically acceptable salts, and/or formulations thereof, b) a second active agent, and optionally c) one or more carriers or compatible excipients. In one embodiment, the corneal disruption or disease is caused by a compound of Formula I or II.

Kits

Also disclosed are kits of the disclosed compounds and compositions for drug delivery into a human, mammal, or cell. The kits can comprise one or more packaged unit doses of a composition comprising one or more compounds of Formula I or II and one or more packaged unit doses of a second active agent to be delivered into a human, mammal, or cell. The unit dosage ampoules or multi-dose containers, in which the compounds of Formula I or II or the second active agent to be delivered are packaged prior to use, can comprise a hermetically sealed container enclosing an amount of the active agent or pharmaceutically acceptable salt, or formulation thereof, suitable for a pharmaceutically effective dose thereof, or multiples of an effective dose. The compounds can be packaged as a sterile formulation, and the hermetically sealed container is designed to preserve sterility of the formulation until use.

The kit of the present application has a single-use eye drop dispenser bottle for delivery of ophthalmic formulation. In an alternative embodiment, the kit of the present application has a multi-use eye-drop dispenser bottle. The multi-dose dispenser bottle has appropriate amount of anti-infective and/or preservative agent, for example without being limited to, 0.005% BAK. The ophthalmic dispenser of the present application has a top and a cap. The container of the present application has a semi-transparent LDPE ophthalmic dispenser bottle with a LDPE dropper tip and HDPE cap. The container may be of other type and form as needed and/or as used in the art.

The following examples are illustrative, but not limiting, of the methods and compositions of the present application. Other suitable modifications and adaptations of the variety of conditions and parameters normally encountered in therapy and that are obvious to those skilled in the art are within the spirit and scope of the embodiments.

General Methodology

Roller Mill

The horizontal roller mill consists of multiple motor driven rollers contained within a metal housing. Individual containers placed between the rollers will rotate at an rpm determined by the speed of the rollers and the diameter of the container. Drug slurry consisting of API, and optionally stabilizers, water, and/or milling media are added to the container before being placed between the rollers. The media used are beads of various sizes, e.g., from 800 microns to 3000 microns, and can be made with Yttria Zirconium. After milling, the dispersion is separated from the media by transferring the contents to a centrifuge tube insert fitted with a screen mesh. After centrifugation, e.g., at approximately 300×G for approximately 5 minutes, the dispersion is collected below the mesh (which retained the media).

Optical Microscopy (OM)

The morphology and size distribution of the particle compositions can be assessed by optical microscopy, and photomicrographs of particles can be taken, for example, using an Olympus BX51 system equipped with an oil immersion 100× objective (1000× magnification). A calibration bar (from 1 um to 100 um) can be set as a comparator on each photomicrograph.

Particle Size Distribution (PSD)

Particle size distribution can be analyzed using laser diffraction light scattering, e.g., with a Horiba LA-950 V2. Generic assumptions are made in setting conditions and the refractive index value. The distributions are volume based. Sample density is adjusted to a generic range of percent transmission on the blue LED light source. A small sample cell (filled with water) can be used rather than the flow through cell, to minimize sample quantity.

Calculation

The following equation was used to determine the volume of diluent (50:50 methanol:water) required in order to prepare choroid, retina, and cornea samples at a specified tissue concentration.

$$\text{Vol.}_{Diluent} = (\text{Mass}_{Tissue}/\text{Conc.}_{Tissue}) - \text{Vol.}_{Tissue} \qquad \text{Equation 1}$$

Where: $\text{Conc.}_{Tissue}$=Desired tissue concentration (mg/mL)
$\text{Mass}_{Tissue}$=Mass of tissue (mg)
$\text{Vol.}_{Diluent}$=Volume of diluent (50:50 methanol:water) (mL)
$\text{Vol.}_{Tissue}$=Volume of tissue (mL), assuming density of 1.0 g/mL To calculate the concentration in ng/g (ng of drug/g of tissue), the following equation was used:

$$\text{Conc.}_{ng/g} = \text{Conc.}_{ng/mL} \times (\text{Vol.}_{Total}/\text{Mass}_{Tissue}) \qquad \text{Equation 2}$$

Where: $\text{Conc.}_{ng}/g$=Calculated concentration (ng of drug/g of tissue)
$\text{Conc.}_{ng/mL}$=Calculated concentration (ng of drug/mL of homogenate)
$\text{Vol.}_{Total}$=Total volume of tissue homogenate (mL)
$\text{Mass}_{Tissue}$=Mass of tissue (g)

To then calculate concentration of drug in tissue* in µM (µmol of drug/volume of tissue), the following equation was used, assuming a tissue density of 1 g/mL:

*Tissue=choroid, retina, or cornea $$\text{Conc.}_{\mu M} = \text{Conc.}_{ng/g}/MW \qquad \text{Equation 3}$$

Where: $\text{Conc.}_{\mu M}$=Calculated concentration (µmol of drug/volume of tissue)
$\text{Conc.}_{ng/g}$=Calculated concentration (ng of drug/g of tissue)
MW=Molecular weight (g/mole)

To calculate concentration of drug in fluid** in M (µmol of drug/volume of fluid), the following equation was used:

**Fluid=plasma $$\text{Conc.}_{\mu M} = \text{Conc.}_{ng/mL}/MW \qquad \text{Equation 4}$$

Where: $\text{Conc.}_{\mu M}$=Calculated concentration (µmol of drug/volume of fluid)
$\text{Conc.}_{ng/mL}$=Calculated concentration (ng of drug/mL of fluid)
MW=Molecular weight (g/mole)

Note: any sample concentrations <LLOQ within the body of this report were dropped or excluded for the calculation of the statistical values reported (average, standard deviation, and percent coefficient of variance).

Draize Eye Irritation Scoring System for Cornea, Iris, and Conjunctiva

| Cornea | | |
|---|---|---|
| A. | Opacity - Degree of density (area which is most dense is taken for reading) | |
| | Scattered or diffuse area - details of iris clearly visible | 1 |
| | Easily discernible translucent areas, details of iris slightly obscured | 2 |
| | Opalescent areas, no details of iris visible, size of pupil barely discernible | 3 |
| | Opaque, iris invisible | 4 |
| B. | Area of cornea involved | |
| | One quarter (or less) but not zero | 1 |
| | Greater than one quarter but less than one-half | 2 |
| | Greater than one-half but less than three quarters | 3 |
| | Greater than three quarters up to whole area | 4 |
| Score equals A × B × 5 Total maximum = 80 | | |
| Iris | | |
| A. | Values | |
| | Folds above normal, congestion, swelling, circumcorneal injection (any one or all of these or combination of any thereof), iris still reacting to light (sluggish reaction is positive) | 1 |
| | No reaction to light, hemorrhage; gross destruction (any one or all of these) | 2 |
| Score equals A × 5 Total possible maximum = 10 | | |
| Conjunctiva | | |
| A. | Redness (refers to palpebral conjunctiva only) | |
| | Vessels definitely injected above normal | 1 |
| | More diffuse, deeper crimson red, individual vessels not easily discernible | 2 |
| | Diffuse beefy red | 3 |
| B. | Chemosis | |
| | Any swelling above normal (includes nictitating membrane) | 1 |
| | Obvious swelling with partial eversion of the lids | 2 |
| | Swelling with lids about half closed | 3 |
| | Swelling with lids about half closed to completely closed | 4 |
| C. | Discharge | |
| | Any amount different from normal (does not include small amount observed in inner canthus of normal rabbits) | 1 |
| | Discharge with moistening of the lids and hairs just adjacent to the lids | 2 |
| | Discharge with moistening of the lids and considerable area around the eye | 3 |
| Score equals (A + B + C) × 2 Total maximum = 20 | | |

Draize et al. (1944) Methods for the study of irritation and toxicity of substances applied topically to the skin and mucous membranes
Scores of 0 are assigned for each parameter if the cornea, iris, or conjunctiva, are normal.

EXAMPLES

Compound-I is a potent and selective small molecule inhibitor of VEGFR-2, along with other proangiogenic RTKs such as the FGF receptors (FGFR-1-3), Tie-2, and the ephrin receptor B4 (EPHB-4). Compound-I was shown to inhibit phosphorylation of specific RTKs, endothelial cell proliferation, and pathologic angiogenesis following systemic administration in murine cornea and rat growth plate models, as well as the growth of human tumor xenografts in athymic mice. Regarding potential ophthalmic indications, the Examples of the present application described below demonstrated that topical ocular delivery of Compound-I provided significant inhibition of pathologic retinal and choroidal neovascularization in clinically-relevant rodent models. A summary of these data follows.

The following studies were conducted to measure the effect of the disclosed compounds on vascular leak and neovascularization of retina tissue.

Example 1

Primary Pharmacodynamics

In Vitro Efficacy Pharmacology of Compound-I.

Compound-I potently inhibits the tyrosine kinase activity of vascular endothelial growth factor receptor-2 (VEGF-2), as well as a select subset of other proangiogenic RTKs, during various in vitro assays. Specifically, Compound-I compound blocked VEGF-stimulated VEGFR-2 phosphorylation in whole cells along with the proliferation of cultured endothelial cells. Compound-I inhibited recombinant tyrosine kinase activity of VEGFR-2 and FGFR-2 with a 50% inhibitory concentration ($IC_{50}$) of 10.55 nM (6 ng/mL) and 8.79 nM (5 ng/mL), respectively; and inhibited VEGFR-2 autophosphorylation in intact cells with an $IC_{50}$=5.27 nM (3 ng/mL). This inhibition was selective versus many other tyrosine kinases, e.g., the VEGFR-2 $IC_{50}$ was approximately 500× and 1000× lower than those for epidermal growth factor receptor (EGFR) and the insulin receptor (IR) tyrosine kinases, respectively (see Table 2).

When using a 10-point titration curve that ranged from 257 to 5000 nM (146-2845 ng/mL), Compound-I exhibited potent inhibition of tyrosine kinase activity for several proangiogenic growth factor receptors, as evidenced by an $IC_{50}$<100 nM (56.89 ng/mL) (see Table 3). The $IC_{50s}$ for this select group of kinases were as follows: recombinant KDR (human isoform of VEGFR-2)=1.27 nM (0.72 ng/mL), Tie-2=10.10 nM (5.75 ng/mL), and FGFRs 1-3=8.50 nM (4.84 ng/mL), 3.08 nM (1.75 ng/mL), and 33.9 nM (19.29 ng/mL), respectively. The compound also blocked the other high-affinity VEGF receptor, VEGFR-1/Flt-1, but with lower potency: $IC_{50}$=122 nM (69.41 ng/mL).

Although VEGFR inhibition appears to be essential for reducing vascular permeability and preventing further neovascular growth, the simultaneous inhibition of VEGF signaling with inhibition of other growth factor signaling pathways (e.g., PDGF and angiopoietins/Tie2) may be linked to unique therapeutic outcomes. The therapeutic outcomes of a broader inhibition of signaling pathways may contribute to the regression of newly established pathologic vessels in the posterior segment of the eye.

300 nM (170.67 ng/mL) of Compound-I completely inhibited VEGFR-2 kinase function (see Table 4) and provided substantial blockade of a similar set of proangiogenic growth factor receptors, including FGFRs-1-3, Tie-2, and EphB-4. An unexpected finding was that the 300 nM concentration was able to completely inhibit the VEGFR-2 kinase function. This concentration falls within the typical range found in the central choroid and retina following five days of topical ocular delivery in rabbits and dogs.

Overview of Drug Substance and Drug Product

Drug Substance: The active pharmaceutical ingredient (API), Formula II Hydrochloride (Compound-I, CP-547, 632-01), is a small molecule of a single polymorph. The API substance is consistently manufactured in purity exceeding 99.7%. Any impurity in drug substance ≥0.15% is suitably qualified in toxicology studies and the current specification for new unknown individual impurities is set to NMT 0.2%. The final drug substance and drug product are analyzed using standard methods.

Drug Product: Compound-I ophthalmic formulations for clinical studies was manufactured in dosage strengths between 0.05%-1.0% (as Compound-I). The strengths used for the GLP batches are 0% (placebo), 0.05%, 0.1%, 0.2%, 0.3%, 0.4%, 0.6%, 0.8%, and 1.0% Compound-I. Compound-I ophthalmic formulations (solutions or suspensions) are used for daily, single use, topical administration to the eye in the clinical trial. In addition to the active ingredient, the drug product may further contain 0.005% BAK as a preservative, purified water as vehicle, and is pH-adjusted with sodium hydroxide to pH 6.0.

Example 2

Sodium Phosphate-Based Gel Drop

The ophthalmic benefits of Compound-I in a sodium phosphate-based formulation (listed in Table 6) results from the self-gelling properties of the API in buffers, such as sodium phosphate. Spontaneous formation of a self-forming, thixotropic gel of Compound-I from a clear solution was formed by increasing API concentration in sodium phosphate. This gel initially appeared clear and then demonstrated increased thickness/viscosity at higher API concentrations, as well as becoming increasingly more opaque, i.e., turbid. Once the API concentration in the phosphate buffer reached super-saturated state, insoluble particulates of Compound-I also were observed within the gel.

Application of a gel with increased viscosity to the surface of the eye increases corneal residence time. Increased corneal residence time in turn facilitates ocular drug absorption. As a result, the intraocular drug concentrations of viscous gels increase in comparison to non-viscous formulations, such as water-like solutions. One way to increase viscosity is to use various viscosity-enhancing excipients, e.g., carboxymethylcellulose, which in effect achieves increased intraocular absorption of different drug substances following topical ocular administration. In this study, however, a thixotropic gel of Compound-I was unexpectedly formed in the absence of any viscosity-enhancing excipients. For example, when Compound-I was dissolved into a simple buffer, such as sodium phosphate, a thixotropic gel was formed. The thixotropic gel, which was formed without any viscosity-enhancing excipients, was formulated as a Gel Drop in this Example.

The Gel Drop of Compound-I was applied to eyes of Dutch-belted rabbits. Gel Drops of Compound-I were administered to Dutch-Belted rabbits for 4 or 5 consecutive days, with three times daily dosing. The concentrations of Compound-I at the target tissues were measured at 1 hour following the last administered dose. Delivery of Compound-I to the posterior segment tissues was dose-dependent and dose-frequency dependent.

The Gel Drop formulations (listed in Table 6) differed in several aspects, such as API concentration, sodium phosphate concentration, presence or absence of tonicity (glycerin) or preservative (benzalkoniumchloride/BAK) agents, solubilizing surfactants (polysorbate 80, tyloxapol, and/or poloxamer), and pH.

Example 3

Tromethamine-Based Suspension

Compound-I (about 1 mg/mL to about 10 mg/mL) in a tromethamine-based formulation formed a suspension. The suspension of Compound-I in a tromethamine-based formulation had >95% of the active drug substance in an insoluble form. This characteristic is distinguishable from the soluble or semi-soluble state of Compound-I in the Gel Drop (the Gel Drop (gel) is not an entirely soluble state as concentration of the active agent increases) or in a Cyclodextrin-based formulation. Tromethamine-based formulations of Compound-I showed increased turbidity with increasing active agent concentration. Administering a topical drop of Compound-I suspension to the eye (which is a combination of soluble and insoluble active agent components) was expected to provide unique benefits relevant to both safety/tolerability and efficacy.

Tromethamine-based suspension of Compound-I was administered to Dutch-Belted rabbits for 4 or 5 consecutive days with three times daily dosing. Ocular tissue and plasma concentrations of Compound-I were measured at 1 hour following the last administered dose. Compound-I in the tromethamine-based suspension delivered concentrations to the target tissues between 10-1000× of its cellular $IC_{50}$ for the various pro-angiogenic RTKs. See Table 7.

The corneal safety and tolerability of topical Compound-I was a direct consequence of the amount of soluble (as opposed to insoluble) active agent applied to the corneal surface, and the resultant corneal tissue concentration. Animals that received topical ocular administration of the tromethamine-based suspension were able to tolerate up to higher level of the active agent concentration in the formulation, as compared to equimolar formulations of the sodium phosphate-based Gel Drop. Results obtained from both Dutch-belted rabbits and beagle dogs suggested that ocular side effects, such as discomfort and inflammation and in some cases, corneal thinning, were more consistently observed when the cornea concentration of Compound-I exceeded 100 µM.

Administration of the tromethamine-based suspension had the unexpected effect on the ocular bioavailability of Compound-I in the posterior segment. The ocular bioavailability of Compound-I in the posterior segment was observed to be directly proportional to the total amount of drug administered (insoluble plus soluble, see Table 7). Although the insoluble drug particulates were not readily available to anterior segment tissues; the inherent and unique physicochemical properties of Compound-I allowed both insoluble and soluble components to gain entry to posterior segment tissues, such as the choroid and retina. Consequently, even higher drug concentrations than those achieved with Gel Drop formulations containing equivalent amounts of the active agent were achieved with the tromethamine-based suspension. Thus, tromethamine-based suspension provided: a) improved corneal tolerability and b) increased bioavailability to the posterior segment, particularly to the choroid, the primary target tissue for treating neovascular (wet) AMD.

Example 4

Cyclodextrin-Based Solution

Cyclodextrins, which are cyclic oligosaccharides made up of six to eight dextrose units (α-, β-, and γ-CDs) joined through one to four bonds, are well-known for their ability to act as a solubilizing agent for relatively insoluble drugs. See Stella & He, Cyclodextrins, *Toxicol. Pathol.*, 36: 30-42 (2008).

A clinical formulation of Compound-I or its free base ophthalmic Solution in 2-hydroxypropyl-β-cyclodextrin (HP-β-CD, KLEPTOSE® HPB) at equal to or more than 1:6 molar ratio or Sulfobutylether-β-cyclodextrin (SBE-β-CD, CAPTISOL®) at P at equal to or more than 1:2 ratio provided solubility with clinical dose strengths of 0.1-1.0% Compound-I.

Cyclodextrin-based solutions of Compound-I or its free base not only improved solubility of the active agent into a uniform solution, but, upon topical ocular administration, also had a novel and previously unobserved characteristic of significantly increased therapeutic index of the active agent at the posterior segment of the eye. The solution reduced anterior segment exposure, thereby providing increased concentration of the active in the solution and increased delivery frequency, which maintained high posterior segment concentrations. Both of these beneficial characteristics are related to the known property of cyclodextrin to form hydrophilic complexes with hydrophobic drugs. See Stella & He, Cyclodextrins, *Toxicol. Pathol.*, 36: 30-42 (2008). When formulated with Compound-I or its free base, cyclodextrin formed a clear, colorless solution and exhibited water-like viscosity. Following topical ocular administration, the Compound-I/cyclodextrin complex had the appearance of being pharmacologically inactive and metabolically inert. The Compound-I/cyclodextrin complex conferred corneal tolerability until cyclodextrin spontaneously dissociated from the active agent, thus making available high concentration of Compound-I at its intended site of action in the posterior segment of the eye, e.g., choroid and retina.

During topical ocular dosing studies lasting from 1 to 30 days in Dutch-belted rabbits, cyclodextrin-based solutions of Compound-I demonstrated dramatically lowered corneal exposures compared to Gel Drop formulations (see Example 2) at similar drug concentrations. The use of cyclodextrin-based solutions of Compound-I provided an approximate 10× reduction in corneal concentrations, as compared to dosing with equimolar formulations of the Gel Drop. Consequently, after 30 days of topical ocular dosing of 0.6% Compound-I as a cyclodextrin-based solution, no untoward findings were attributed to test-article or vehicle. The cyclodextrin-based solution of Compound-I also achieved equal or significantly higher concentrations of drug within the posterior segment target tissues, such as at the central choroid and the central retina. The combined effects of decreasing corneal drug exposure so as to avoid poor ocular tolerability, while increasing posterior segment bioavailability so as to increase RTK inhibition, may significantly increase the therapeutic index and corresponding benefit(s) experienced by patients.

For both suspension-based formulations (see Example 3) and the cyclodextrin formulations, the therapeutic window is expanded due to significantly reduced exposure (10-100× or 1-2 log reduction). The reduced exposure improves corneal safety/tolerability, which allows higher concentrations or frequency of dosing of Compound-I to be administered topically. The higher concentrations enables the drug to achieve higher back of the eye target tissue concentrations, which improves the therapeutic efficacy of Compound-I.

This study demonstrated that in rabbits and dogs, topical ocular dosing of ophthalmic gel drops, was associated with high corneal tissue exposure (≥100 uM) and corresponding untoward observations in the anterior segment, such as discomfort, corneal and conjunctival inflammation, corneal epithelial erosion and/or thinning and degeneration. In contrast, repeated topical ocular dosing of Compound-I ophthalmic solution produced corneal exposure that are roughly 5 to 10-fold lower than an equimolar dose of ophthalmic gel drops, and are free of untoward clinical or histopathologic findings. Furthermore, topical ocular dosing with Compound-I ophthalmic solution achieved equal or higher target therapeutic exposure in the central choroid in comparison to an equimolar dose of the ophthalmic gel drop. Overall, the combination of decreased corneal exposure and corresponding improved ocular tolerability, while simultaneously maintaining or promoting drug delivery to the posterior segment target tissues, along with improved physicochemical stability, will provide greater benefit to patients compared to the ophthalmic Gel Drop formulation.

Example 5

1- to 5-Day PK Results with Topical Ocular Compound-I in Cyclodextrin-Based Solutions Following topical ocular dose administration of various formulations and dosage regimens of Compound-I in Dutch Belted rabbits, ocular pharmacokinetics was investigated. Nine (9) different topical ocular formulations having three doses of Compound-I were administered either once per day (q.d.) or twice per day (b.i.d.) for 1, 4, or 5 consecutive days. The study design (see Tables 10A-B) consisted of seventy-two (72) rabbits each receiving a 30 µL bilateral topical ocular dose of one of three (3) Compound-I formulations, or vehicle formulation, using a positive displacement pipette.

The composition of each Compound-I formulation is described in Table 8A. All doses were administered within ±1 hour of the scheduled dose time. On day 1, Groups 1, 2, 4-6, 8, 10, 11, 13, 15, and 17 received one dose (q.d.) for either one (1) or four (4) days. On days 1 through 4, Groups 3, 7, 9, 12, 14, and 16 received b.i.d. dosing approximately 8 hours apart at 7:00 µM and 3:00 µM for four (4) days. Animals in Groups 18 and 19 received b.i.d dosing of vehicle only formulations for five (5) consecutive days.

Ocular sampling occurred for Group 1 at 0.5, 1, 2, 4, 8, or 24 hours post-dose relative to the day 1 dose. Ocular sampling occurred for Groups 2 and 6 at 1, 8, and 24 hours post-dose relative to the day 5 morning dose. Ocular sampling for Groups 3, 7, 8, 11, and 13 occurred at 1 and 24 hours post-dose relative to the day 5 morning dose. Ocular sampling for Groups 4, 9, 10, 12, 14, 15, 16, and 17 occurred at 1 hour post-dose relative to the day 5 morning dose. Group 5 ocular sampling occurred at 0.5, 1, 2, 4, 8, and 24 hours post-dose relative to the day 1 dose. Animals in Groups 18 and 19 were followed only by clinical observations for five (5) days.

Aqueous humor, cornea, central and peripheral retina, and central and peripheral choroid samples were collected. Aqueous humor, cornea, central retina, and central choroid samples were then assayed. Peripheral retina and peripheral choroid samples were assayed only for Groups 1-8, 12, 14, and 16 per study protocol.

Rabbit aqueous humor, cornea, central and peripheral retina, and central and peripheral choroid samples were analyzed. Calibration curves were prepared in control matrix to determine the concentration of Compound-I in the various tissues.

Example 6

5-Day PK Results with Topical Ocular Compound-I in Cyclodextrin-Based Solutions

Following ocular dose administration of various dose regimens of topical ocular solutions of Compound-I containing hydroxypropyl-β-cyclodextrin ("HDβCD") in Dutch-Belted rabbits, the ocular pharmacokinetics was calculated. Nine (9) different topical ocular solutions having four different doses of Compound-I were administered either once per day (q.d.) or twice per day (b.i.d.) for either 4 or 5 consecutive days. The study design consisted of forty (40) rabbits each receiving a 30 µL bilateral topical ocular dose of one of four (4) Compound-I dosage strengths, using a positive displacement pipette.

All doses were administered with ±1 hour of the scheduled dose time, except on day 1 for Groups 1, 4, and 10. The first dose on day 1 was administered at 12:00 μM, and the second dose (for Groups 1 and 10) was administered approximately 4 hours after. This was due to delayed arrival of formulations. All other dosing for these groups was as scheduled. On day 1, Groups 4-8, and 11-12 received one dose (q.d.) for four (4) days. On days 1 through 4, Groups 1-3, and 9-10 received b.i.d. dosing approximately 8 hours apart for four (4) days.

Ocular sampling occurred one hour following the first daily dose on day 5 for all groups, except Groups 5b and 6b, where ocular sampling occurred 24 hours after the first daily dose on day 4.

Blood samples for plasma collection were obtained just prior to scheduled euthanasia for all animals. Aqueous humor, cornea, central and peripheral retina, and central and peripheral choroid samples were collected. Cornea, central retina, and central choroid samples from groups 1-12 were assayed. Aqueous humor, peripheral retina, and peripheral choroid samples were not assayed.

Example 7

Concentrations of Compound-I (in μM) in Various Ocular Fluids and Tissues

The ocular solution of Compound-I comprising cyclodextrin was prepared and tested in different groups of animals. Upon topical ocular administration of a solution of 0.4% (4 mg/mL) Compound-I and cyclodextrin, the concentration of the active agent was measured in various tissues and fluids of the eye. Average concentration of Compound-I was measured in the central choroid, central retina, aqueous humor, and cornea. Compound-I was in a solution (0.4% or 4 mg/mL) with 8.41% KLEPTOSE® and 0.142% phosphate buffer; 8.9% KLEPTOSE® HPB and 0.142% phosphate; 4.88% CAPTISOL® and 0.142% phosphate; or 4.88% CAPTISOL® and 0.122% phosphate. See Table 10A-B.

The central choroid concentration of Compound-I was between 0.259 μM and 0.769 μM. See Table 10A. The central retina concentration of Compound-I was between 0.0531 μM-0.124 μM. See Table 10A. The aqueous humor concentration of Compound-I was between 0.00313 μM-0.00656 μM. See Table 10A. And the corneal concentration of Compound-I was 6.49 μM-30 μM. See Table 10A. The cyclodextrins used to prepare the solutions were KLEPTOSE® HPB or CAPTISOL®. See Table 10B.

Example 8

Ocular Toxicology Studies

Dose-limiting ocular toxicity was characterized by corneal and conjunctival findings in Dutch-Belted rabbits and beagle dogs. These ocular findings from repeat-dose toxicology studies with Compound-I ophthalmic gel drops were based upon clinical ophthalmic and histopathologic evaluations and limited to conjunctival hyperemia, chemosis, congestion, and discharge, corneal opacification and epithelial erosion, and keratoconjunctivitis. No untoward alterations involving deeper structures of the eye (iris, lens, ciliary body, retina, choroid, sclera) or the optic nerve were observed. Retinal function was normal in all test article and vehicle treated groups during full-field electroretinograms performed in rabbits.

The objectives for the exploratory ocular toxicology studies were to identify: a) a topical ocular formulation that was well tolerated and b) one that could achieve the targeted therapeutic concentrations of Compound-I in the central choroid.

Mean Compound-I ocular tissue concentrations following twice daily topical dosing with 0.3% Compound-I ophthalmic gel drop formulations with and without benzylalkonium chloride were highest in the cornea (236-260 μM)>>peripheral choroid (2.79-4.10 μM), central choroid (0.340-0.496 μM), peripheral retina (0.150-0.309 μM) and aqueous humor (0.0197-0.0395 μM) in Dutch-Belted rabbits.

Tris-based suspension formulations were well tolerated, where clinical ophthalmic examinations revealed a notable absence of corneal findings with only a few sporadic incidences of mild conjunctivitis in Dutch-Belted rabbits. Moreover, the eyes from animals that had received 0.3% w/v Compound-I Tris-based suspension twice daily for 30 days were considered normal during microscopic evaluations. Mean Compound-I ocular tissue concentrations, assessed at 1 hour±15 minutes after the first daily topical ocular dose on day 30 for the twice daily topical dosing with 0.3% Compound-I Tris-based suspensions with and without benzylalkonium chloride, were highest in the cornea (2.69-3.10 μM)>>peripheral choroid (0.781-1.21 μM), central choroid (0.303-0.319 μM), peripheral retina (0.0819-0.0868 μM), central retina (0.0495-0.0592 μM), and aqueous humor (0.00127-0.00145 μM).

Cyclodextrin-based solutions, using hydroxypropyl-beta-cyclodextrin (HP-β-CD, KLEPTOSE® HPB), were well tolerated when administered topically for 30 days, twice daily at 0.1% Compound-I (2.1% HP-β-CD), twice daily at 0.2% Compound-I (4.21% HP-β-CD), once or twice daily at 0.4% Compound-I (8.41% HP-β-CD), and once or twice daily at 0.6% Compound-I (up to 12.62% HP-β-CD) in Dutch-Belted rabbits. Moreover, in a similar repeat dosing study, cyclodextrin-based solutions of 0.4% w/v Compound-I in KLEPTOSE® HPB, KLEPTOSE® HP, or CAPTISOL® were well-tolerated when dosed twice daily for 24 days. No overt ocular toxicity related to Compound-I or vehicle treatment was found during clinical ophthalmic or microscopic examinations in either study.

In the 24-day study, ocular tissue concentrations from eyes treated with cyclodextrin-based solutions of Compound-I were assessed at 1 hour±15 minutes after the first daily topical ocular dose on day 24 were in descending order highest in the cornea (6.49-30 μM)>>center-punch choroid (0.212-0.769 μM)>center-punch retina (0.0531-0.124)>aqueous humor (0.002-0.007).

In summary, dose-limiting corneal toxicity was observed with Compound-I ophthalmic Gel Drop formulations. The ophthalmic Gel Drop renders five-fold to fifteen-fold higher corneal concentrations of Compound-I compared to cyclodextrin based solution, and fifty-fold to hundred-fold higher corneal concentrations of Compound-I compared to Tris-based suspensions. Compound-I Tris-based suspensions and cyclodextrin-based solutions were well tolerated with no evidence of overt ocular toxicity. Dose levels that were well tolerated for the cyclodextrin-based solutions or Tris-based suspensions of Compound-I when administered once or twice daily ranged from about 0.005% to about 5.0% w/v for at least 30 days. Cyclodextrin-based solutions also provided the highest central choroid concentrations of Compound-I when using equimolar doses of the three formulations, and met or exceeded target therapeutic concentrations.

Example 9

Phase I Protocol for Dose-Escalation Study in Patients with Neovascular AMD

The Phase I study is a twelve-week, open-label, dose-escalating, multi-center trial designed to evaluate the safety, tolerability, and pharmacokinetics following topical ocular administration of Compound-I in patients with neovascular age-related macular degeneration (AMD). Up to 60 patients total are treated one to two times daily with topical ocular dosing of Compound-I ophthalmic solution for three months, where three dose-escalating monotherapy arms and one adjunct therapy arm using a single intravitreal injection of LUCENTIS® plus the maximally-tolerated monotherapy dose are planned (15 patients per treatment arm). Patients that meet pre-specified vision and CNV lesion criteria confirmed by an independent reading center are allowed to simultaneously discontinue topical ocular dosing and receive treatment with standard-of-care.

Compound-I ophthalmic solution for clinical studies is manufactured in at least 3 dosage strengths, ranging from 0.1% to 1.0% (as Compound-I). The strengths for the GLP batches are 0% (placebo), 0.1%, 0.3%, 0.6%, and 1.0% Compound-I HCl. Up to 2- to 3-fold incremental doses (approximately ½ log unit steps) are administered to succeeding cohorts.

Example 10

A "non-gel," "non-viscous," homogeneous ophthalmic solution topical formulation that is both physically and chemically stable over the drug strengths of 0.1-1.0% (1 to 10 mg/ml) was prepared by measuring the Compound-I concentration, cyclodextrin complexing agent concentration, pH, and tonicity, on Compound-I solubility and stability. A suitable buffering system prevents pH drift on stability at concentrations less than 1 mg/mL. Both phosphate and Trometamol (Tris) were evaluated as buffering agents. Sodium chloride was used to adjust tonicity.

The product quality attributes are shown in Table 14.

TABLE 14

| Product Quality Attributes | |
|---|---|
| Solvent | Solubility (mg/mL) |
| Color Appearance of formulation | Clear colorless with no visually apparent |
| pH | pH 5.5-7.0 |
| Turbidity | Clear |
| Viscosity | Free flowing, water-like and filterable |
| Tonicity | Isotonic |
| Sedimentation | None |
| Mixing end point | Clear colorless with no visually apparent |
| Solubility | Solubility ≥6 mg/ml |

Formulation Preparation

The formulations outlined in Tables 12 and 13 were prepared using the general procedure listed.

The formulation was made up to volume with water for injection and stirred for 30 minutes at 500 rpm. Final pH was checked and adjusted with either, NaOH or HCl to the target range. Approximately 5 ml aliquots is directly filtered into semi-transparent 5 ml LDPE bottles while continuously stirring at constant speed with the aid of Watson Marlow Pumpsil D tubing, fitted to a Flexicon filler and attached to 0.2 micron PVDF capsule filter. Samples are stored at 2-8° C. until all sample preparation is complete. All samples will then be submitted to analytical for storage and testing.

Example 11

EGFR Tyrosine Phosphorylation Assay in Corneal Epithelial Cells (hTCEpi Cells) to Determine EGFR Activity of Compounds of Formula I or II An EGFR tyrosine assay in corneal epithelial cells was performed to determine whether higher concentrations of EGF can overcome inhibition of EGFR kinase activity by a compound of Formula I or II.

35 mm dishes of hTCEpi cells were serum starved and then were pre-treated with different concentrations of a compound of Formula I or II, e.g., Compound-I, or a control, AG1478 (an EGFR kinase inhibitor), for 30 minutes, followed by treatment with EGF (10, 50, 100 ng/ml) for 15 minutes. Six concentrations of a compound of Formula I or II, e.g., 0, 1 µM, 3 µM, 10 µM, 30 µM, 100 µM, or 1 µM AG1478 as a control, were used for each EGF concentration (10, 50, 100 ng/ml). Additional controls run were no compound of Formula I or II or no EGF. All experiments were repeated three times. Cells were then harvested and immunoblotted for determination of phosphorylated EGFR (tyrosine 1068 and tyrosine 1045) and total EGFR.

Figure 1:
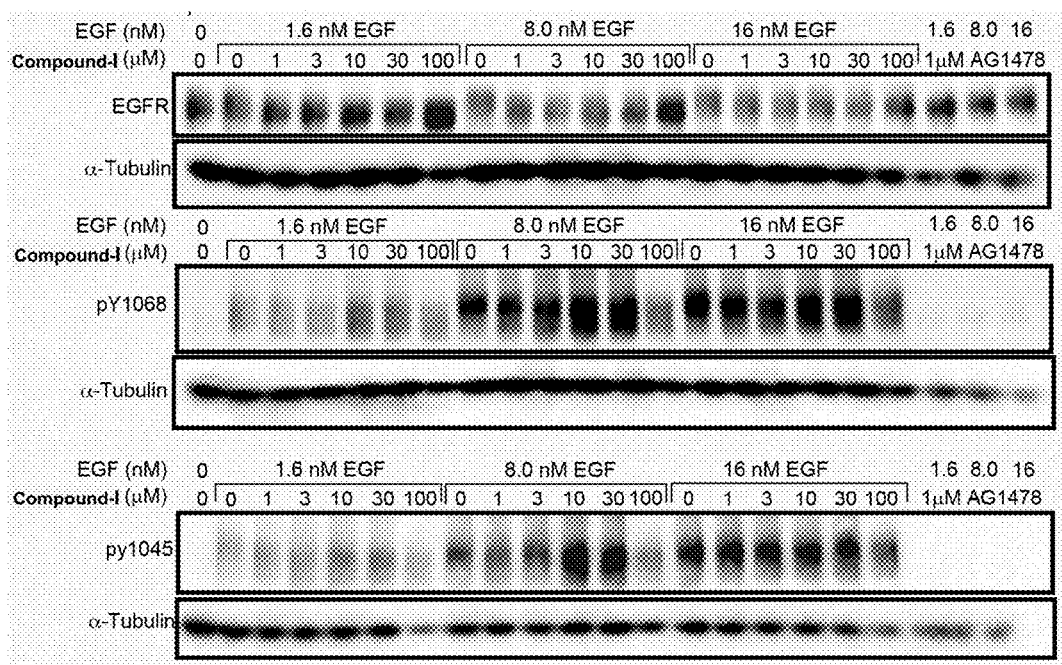
FIG. 1 is a series of immunoblots of EGFR phosphorylation in immortalized corneal epithelial cells (hTCEpi cells) treated with varying concentrations of a first active agent of the present application or a control (AG1478, an EGFR kinase inhibitor) and of EGF (top panels: immunoblotting of total EGFR, middle panels: immunoblotting showing phosphorylation of tyrosine 1068 of EGFR, bottom panels: immunoblotting showing phosphorylation of tyrosine 1045 of EGFR).

EGFR phosphorylation serves as a readout of receptor activity. As shown in FIG. 1, high concentrations of a compound of Formula I or II were able to inhibit ligand-stimulated EGFR tyrosine phosphorylation, and increasing concentrations of a compound of Formula I or II decreased EGFR tyrosine phosphorylation at both sites. Increasing concentrations of EGF overcome the EGFR inhibition and corneal adversity due to the compound of Formula I or II (FIG. 1). The EGFR-specific inhibitor, AG1478, has an $IC_{50}$=3 nM, and at 1 µM AG1478 completely blocked EGFR phosphorylation. It is estimated that 100 µM of a compound of Formula I or II inhibits EGFR phosphorylation ~75-80%.

Example 12

EGFR Tyrosinephosphorylation Assay in Corneal Epithelial Cells (hTCEpi Cells) with Compounds of Formula I or II, and a Second Active Agent An EGFR tyrosine assay in corneal epithelial cells was performed to determine if vitamin K, nicotinic acid, or nicotinamide can prevent compounds of Formula I or II from inhibiting EGFR and if there is an increase in EGFR activity.

Figure 2:
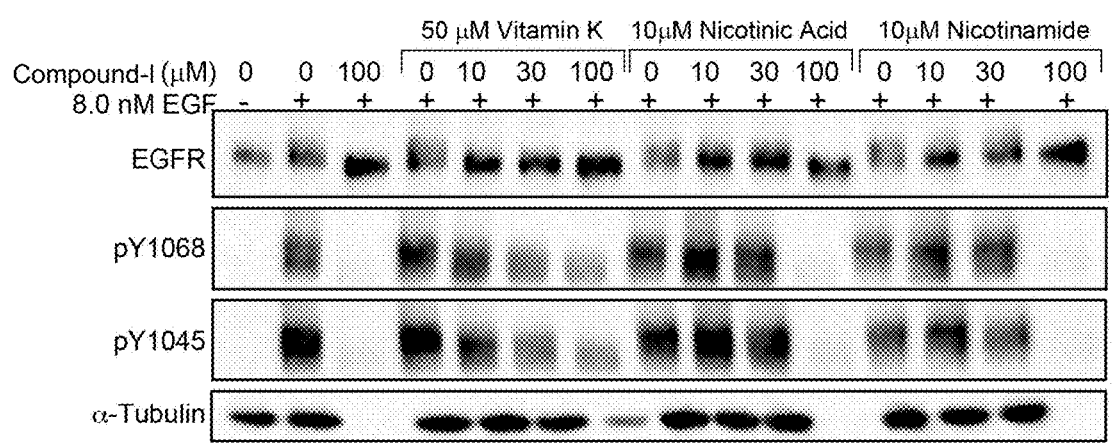
FIG. 2 is a series of immunoblots of EGFR phosphorylation in immortalized corneal epithelial cells (hTCEpi cells)

35 mm dishes of hTCEpi cells were serum starved and then were pre-treated with vitamin K (50 µM), nicotinic acid (10 µM), or nicotinamide (10 µM) for 4 hours, followed by treatment with different concentrations of a compound of Formula I or II, e.g., Compound-I, for 30 minutes. The cells were then incubated with EGF (50 ng/ml) for 15 minutes. Cells were harvested and cell lysates were immunoblotted for determination of phosphorylated EGFR (tyrosine 1068 and tyrosine 1045) and total EGFR concentration. As shown in FIG. 2, vitamin K, nicotinic acid, or nicotinamide overcome Formula I or II compound-mediated corneal adversity (EGFR inhibition). In addition, FIG. 2 shows that vitamin $K_3$ (menadione) most effectively attenuated Formula I or II compound-mediated inhibition of EGFR tyrosine phosphorylation.

Example 13

Determination of Cell Migration/Proliferation (In Vitro Wound Healing) in Corneal Epithelial Cells (hTCEpi Cells): Effects of Compounds of Formula I or II and EGF Determination of cell migration/proliferation in corneal epithelial cells was performed to determine cell migration/proliferation in the presence of varying concentrations of a compound of Formula I or II and EGF.

hTCEpi cells were plated with silicone plugs. The cells were then serum starved and pre-treated with varying concentrations of a compound of Formula I or II or a control compound, AG1478, for 30 minutes. The silicone plugs were then removed to create the acellular area. The cells were photographed and then treated with EGF (10, 50, or 100 ng/ml) or VEGF (10 ng/ml) together with a compound of Formula I or II or AG1478 for 16 hours. The cells were again photographed and cell migration was quantified from the micrographs. All experiments were repeated three times.

Four concentrations of a compound of Formula I or II (0, 3 µM, 10 µM, 30 µM) or 3.2 µM AG1478 (an EGFR kinase inhibitor), were used for each EGF concentration or VEGF. Additional controls run included no compound of Formula I or II and no EGF.

The data allows determination of whether a compound of Formula I or II prevents the in vitro measures of corneal epithelial wound healing (cell migration and proliferation) and if higher levels of EGF overcome receptor tyrosine kinase inhibition. As shown in FIGS. 3A and 3B, a compound of Formula I or II caused a dose-dependent inhibition of EGFR-mediated hTCEpi cell in vitro "wound healing".

Example 14

Determination of Cell Migration/Proliferation (In Vitro Wound Healing) in Corneal Epithelial Cells (hTCEpi Cells): Effects of Compounds of Formula I or II and a Second Active Agent Determination of cell migration/proliferation in corneal epithelial cells was performed to determine cell migration/proliferation in the presence of varying concentrations of a compound of Formula I or II alone or together with vitamin K, nicotinic acid, or nicotinamide.

hTCEpi cells were plated with silicone plugs. The cells were then serum starved and pre-treated with varying concentrations of vitamin $K_3$ analog, menadione, for 4 hours and supplemented with the varying concentrations of a compound of Formula I or II for 30 minutes. The plugs were removed. The cells were photographed and then treated with various concentrations of vitamin K, EGF, and/or a compound of Formula I or II. The cells were again photographed and cell migration was quantified from the micrographs. Additional controls run included no compound of Formula I or II and no EGF. All experiments were repeated three times.

As shown in FIGS. 4A and 4B, the inhibitory effects of a compound of Formula I or II on in vitro wound healing can be reversed by the addition of 0.3 µM menadione. There was a statistically significant difference in in vitro wound healing when 0.3 µM of a compound of Formula I or II was combined with 0.3 µM menadione versus 0.3 µM of a compound of Formula I or II alone.

Example 15

Determination of Basal and EGF-Mediated Corneal Wound Healing In Vivo: Effects of Compounds of Formula I or II Determination of the effects of a compound of Formula I or II on basal and ligand stimulated rates of corneal wound healing was determined in C57/Bl mice.

Corneas of 8 week old C57/Bl mice were wounded (1.5 mm superficial epithelial wound) and then pre-treated with a compound of Formula I or II (0, 1.0 µM, 10 µM, 30 µM, or 50 µM), followed by addition of EGF (0, 10, 100 ng/ml). As a control, AG1478 (an EGFR kinase inhibitor) was used in the absence and presence of 100 ng/ml EGF. Wound size was monitored by fluorescein staining and fluorescent photography over the course of 40 hours. Wound closure was quantified using Image J software.

As shown in FIGS. 5A, 5B, 5C, and 5D, in vivo corneal epithelial wound healing was reduced in the presence of a compound of Formula I or II in a dose dependent manner. Maximal inhibition of wound healing was observed with a compound of Formula I or II concentrations that were five times greater than those of AG1478. Pre-treatment with a compound of Formula I or II for 48 hours before making the wound to the cornea inhibited corneal epithelial wound healing at a lower concentration of a compound of Formula I or II than without the pre-treatment.

Example 16

Determination of Basal and EGF-Mediated Corneal Wound Healing In Vivo: Effects of Compound of Formula I or II and a Second Active Agent Determination of the effects of a compound of Formula I or II and/or a second active agent on corneal wound healing was determined in C57/Bl mice.

Corneas of 8 week old C57/Bl mice were pre-treated with topical administration of vehicle, 0.3 µM menadione, 10 µM of a compound of Formula I or II, 0.3 µM menadione and 10 µM of a compound of Formula I or II 48 hours before the corneas were wounded (1.5 mm superficial epithelial wound). Wound size was monitored by fluorescein staining and fluorescent photography. Wound closure was monitored over the course of 40 hours.

As shown in FIGS. 6A, 6B, and 6C, menadione (0.3 µM) reversed the effects of a compound of Formula I or II (10 µM) pre-treatment on corneal epithelial wound healing.

Example 17

Effect of Menadione on Inhibition of VEGFR by Compounds of Formula I or II

Human retinal endothelial cells were treated with 0, 0.3, or 3 µM menadione for 4 hours, followed by 30 minutes of treatment with varying concentrations of a compound of Formula I or II (1 nM, 10 nM, 100 nM, or 1 µM) in menadione. The cells were then stimulated with 0.5 nM (10 ng/ml) VEGF. The cells were lysed. The lysates were resolved by 7.5% SDS-PAGE, transferred to nitrocellulose, and immunoblotted for phosphorylated VEGFR2, total VEGFR2, or α-tubulin as a loading control. As shown in FIG. 7A, menadione did not change the $IC_{50}$ of inhibition of VEGFR2 phosphorylation mediated by a compound of Formula I or II.

Example 18

Effect of Menadione on the Proliferation of Primary Human Retinal Microvascular Endothelial Cells Human retinal endothelial cells were pretreated with menadione for 4 hours, then with the indicated concentration of a compound of Formula I or II for 30 minutes, and supplemented with 0.5 nM (10 ng/ml) VEGF overnight. Viable cells were quantified by Alamar Blue Assay (Thermo Fisher). Data were plated as the fold growth relative to cells treated with no VEGF or a compound of Formula I or II, and are shown as the average±S.E.M. in FIG. 7B. As shown in FIG. 7B, menadione did not change the $IC_{50}$ of inhibition of VEGF-mediated retinal endothelial cell proliferation mediated by a compound of Formula I or II.

Example 19

Determination of Mechanism by which Menadione Enhances EGFR Activity hTCEpi cells were pretreated with menadione (0, 0.3, or 3.0 μM) for 4 hours. Cells were then incubated with 8.0 nM (50 ng/ml) EGF for 0-3 hours. The cells were lysed and the lysates were resolved by SDS-PAGE, and immunoblotted for phosphorylated EGFR (pY1068), total EGFR, or α-tubulin. As shown in FIG. 8, menadione treatment did not change basal EGFR phosphorylation or slow EGFR dephosphorylation. 0.3 mM menadione slowed the kinetics of EGFR degradation, indicating that menadione may sustain EGFR receptor signaling by slowing the kinetics of receptor degradation or increasing the rate of new receptor synthesis.

Example 20-1

Ocular Pharmacokinetics of Formulations of the Application in Dutch Belted Rabbits A non-GLP study was conducted to assess the ocular pharmacokinetics of a first active agent of the present application (e.g., Formula II or Compound-I), in suspension or solution, when administered once or twice daily, as a topical instillation, to both eyes of Dutch Belted rabbits for four days. The study design (Table 15-1) consisted of forty-five (45) Dutch Belted rabbits, each receiving a 30 μL bilateral topical ocular dose. The administration was conducted according to the dosing regimen in Table 15-1.

TABLE 15-1

Study design

| Group | | No. of Rabbits | Test Article Formulation | Conc. | Dose Volume | Dosing Frequency and Duration[a] | Sample Time Points |
|---|---|---|---|---|---|---|---|
| 1 | A | 3 | 0.4% Formula II; 0.08% Pluronic F-127; 2.5% Glycerol; Large Particles in suspension | 4 mg/mL | 30 μL/ eye/dose | QD for 4 Days | 1 hr post dose on Day 5 |
| 2 | B | 3 | 0.4% Formula II; 0.08% Pluronic F-127; 2.5% Glycerol; Nano Particles in suspension | 4 mg/mL | 30 μL/ eye/dose | QD for 4 Days | 1 hr post dose on Day 5 |
| 3 | C | 3 | 0.2% Formula II; 0.04% Pluronic F-127; 2.5% Glycerol; Large Particles in suspension | 2 mg/mL | 30 μL/ eye/dose | QD for 4 Days | 1 hr post dose on Day 5 |
| 4 | D | 3 | 0.2% Formula II; 0.04% Pluronic F-127; 2.5% Glycerol; Nano Particles in suspension | 2 mg/mL | 30 μL/ eye/dose | QD for 4 Days | 1 hr post dose on Day 5 |
| 5 | E | 3 | Compound-I Ophthalmic solution | 4 mg/mL | 30 μL/ eye/dose | QD for 4 Days | 1 hr post dose on Day 5 |
| 6 | F | 3 | Compound-I Ophthalmic solution | 2 mg/mL | 30 μL/ eye/dose | QD for 4 Days | 1 hr post dose on Day 5 |
| 7 | G | 3 | Compound-I Ophthalmic solution | 1 mg/mL | 30 μL/ eye/dose | QD for 4 Days | 1 hr post dose on Day 5 |
| 8 | H | 3 | Compound-I Ophthalmic solution | 0.1 mg/mL | 30 μL/ eye/dose | QD for 4 Days | 1 hr post dose on Day 5 |
| 9 | I | 3 | 0.4% Formula II; 0.08% Pluronic F-127; 2.5% Glycerol; Large Particles in suspension | 4 mg/mL | 30 μL/ eye/dose | BID for 4 Days | 1 hr post dose on Day 5 |
| 10 | J | 3 | 0.4% Formula II; 0.08% Pluronic F-127; 2.5% Glycerol; Nano Particles in suspension | 4 mg/mL | 30 μL/ eye/dose | BID for 4 Days | 1 hr post dose on Day 5 |
| 11 | K | 3 | 0.2% Formula II; 0.04% Pluronic F-127; 2.5% Glycerol; Large Particles in suspension | 2 mg/mL | 30 μL/ eye/dose | BID for 4 Days | 1 hr post dose on Day 5 |
| 12 | L | 3 | 0.2% Formula II; 0.04% Pluronic F-127; 2.5% Glycerol; Nano Particles in suspension | 2 mg/mL | 30 μL/ eye/dose | BID for 4 Days | 1 hr post dose on Day 5 |
| 13 | M | 3 | Formula II Ophthalmic solution | 2 mg/mL | 30 μL/ eye/dose | BID for 4 Days | 1 hr post dose on Day 5 |
| 14 | N | 3 | Formula II Ophthalmic solution | 1 mg/mL | 30 μL/ eye/dose | BID for 4 Days | 1 hr post dose on Day 5 |

TABLE 15-1-continued

Study design

| Group | No. of Rabbits | Test Article Formulation | Conc. | Dose Volume | Dosing Frequency and Duration[a] | Sample Time Points |
|---|---|---|---|---|---|---|
| 15 O | 3 | Formula II Ophthalmic solution | 0.1 mg/mL | 30 µL/ eye/dose | BID for 4 Days | 1 hr post dose on Day 5 |

[a] A single dose will be administered on Day 5.
OQ - once daily;
BID - twice daily Ocular sampling occurred one hour following the first daily dose on Day 5 for all groups. Whole blood samples using $K_2$EDTA as an anticoagulant were collected from all animals on Day 5, 1 hour post dose. The whole blood was placed on ice until samples were spun in a centrifuge to separate the plasma. Aqueous humor, conjunctiva, cornea, central retina, peripheral retina, central choroid, and peripheral choroid samples were collected following necropsy. Samples were then frozen at −70° C. or lower. All Groups 1-15 plasma, central retina, central choroid, and cornea samples were assayed.

For all dose groups, ocular tissue concentrations of Formula II or Compound-I assessed on Day 5 were in descending order: highest in the cornea>>central choroid>central retina (Table 15-2). The highest cornea concentrations of Formula II or Compound-I were seen in Group 10. The lowest cornea concentrations of Formula II or Compound-I were seen in Group 8. In general, higher central retina and central choroid concentrations were associated with higher cornea concentrations of Formula II or Compound-I. No advantage of other formulations over ophthalmic solutions of Formula II or Compound-I was seen with respect to a reduction in cornea concentrations or an increase in central retina or central choroid concentrations of Formula II or Compound-I.

TABLE 15-2

| Group | Plasma* (µM) | Central Retina (µM) | Central Choroid (µM) | Cornea (µM) |
|---|---|---|---|---|
| 1 | 0.00500 | 0.0560 | 0.152 | 22.1 |
| 2 | 0.00487 | 0.0620 | 0.117 | 34.0 |
| 3 | 0.00238 | 0.0312 | 0.127 | 9.25 |
| 4 | 0.00294 | 0.0353 | 0.108 | 21.4 |
| 5 | 0.00424 | 0.0551 | 0.116 | 11.9 |
| 6 | 0.00319 | 0.0413 | 0.101 | 9.60 |
| 7 | 0.00234 | 0.0258 | 0.0941 | 6.98 |
| 8 | <LLOQ | <LLOQ | <LLOQ | 0.783 |
| 9 | 0.00350 | 0.0707 | 0.155 | 29.0 |
| 10 | 0.00391 | 0.0920 | 0.336 | 62.2 |
| 11 | 0.00226 | 0.0412 | 0.162 | 16.0 |
| 12 | 0.00308 | 0.0709 | 0.111 | 28.8 |
| 13 | 0.00256 | 0.0472 | 0.149 | 16.1 |
| 14 | 0.00214 | 0.0316 | 0.108 | 6.63 |
| 15 | <LLOQ | 0.00926 | <LLOQ | 0.925 |

*Average based on n = 3
Plasma LLOQ = 0.00188 µM
Central Retina LLOQ = 0.00751 µM
Central Choroid LLOQ = 0.0563 µM
Cornea LLOQ = 0.0376 µM Gross ocular examinations using the Draize scale for scoring ocular irritation were performed on all animals prior to the first dose on each day during the study. All formulations were well tolerated. In addition, animals were observed for general health pre-study, during dosing, and at necropsy. All animals assigned to study were normal. Necropsy evaluations consisted of observations in addition to those already noted on Draize Score sheets and Ophthalmologic Exam forms. For all formulations, dosing observations were assessed using the Draize ocular irritation scoring system. No abnormal observations were noted except for the following: prior to necropsy on Day 5, Redness Level 1 in both eyes was noted in one animal in Group I and one animal in Group M.

Example 20-2

Ocular Pharmacokinetics of Formulations of the Application in Dutch Belted Rabbits A non-GLP study was conducted to assess the ocular pharmacokinetics of a first active agent of the present application (e.g., Formula II or Compound-I), in suspension or solution, when administered one, three, or four times daily, as a topical instillation, to both eyes of Dutch Belted rabbits for four days. The study design (Table 16-1) consisted of thirty-nine (39) Dutch Belted rabbits, each receiving a 30 µL bilateral topical ocular dose. The administration was conducted according to the dosing regimen in Table 16-1.

TABLE 16-1

Study design

| Group | | No. of Rabbits | Test Article Formulation | Conc. | Dose Volume | Dosing Frequency and Duration[a] | Sample Time Points |
|---|---|---|---|---|---|---|---|
| 1 | A | 3 | Compound-I Ophthalmic Solution (Control) | 4 mg/mL | 30 µL/ eye/dose | QD for 4 Days | 1 hr post dose on Day 5 |
| 2 | B | 3 | Compound-I Ophthalmic Solution (Control) | 2 mg/mL | 30 µL/ eye/dose | QD for 4 Days | 1 hr post dose on Day 5 |
| 3 | C | 3 | Compound-I Ophthalmic Solution | 0.1 mg/mL | 30 µL/ eye/dose | QD for 4 Days | 1 hr post dose on Day 5 |

TABLE 16-1-continued

Study design

| Group | | No. of Rabbits | Test Article Formulation | Conc. | Dose Volume | Dosing Frequency and Duration[a] | Sample Time Points |
|---|---|---|---|---|---|---|---|
| 4 | D | 3 | Compound-I Ophthalmic Solution | 0.1 mg/mL | 30 μL/ eye/dose | TID for 4 Days | 1 hr post dose on Day 5 |
| 5 | E | 3 | 0.4% Formula II; Large 3 μm particles in suspension | 4 mg/mL | 30 μL/ eye/dose | QD for 4 Days | 1 hr post dose on Day 5 |
| 6 | F | 3 | 0.4% Formula II; Large Particles, 3 μm + HPBCD in suspension | 4 mg/mL | 30 μL/ eye/dose | QD for 4 Days | 1 hr post dose on Day 5 |
| 7 | G | 3 | 0.4% Formula II; Extra-large 35 μm particles in suspension | 4 mg/mL | 30 μL/ eye/dose | QD for 4 Days | 1 hr post dose on Day 5 |
| 8 | H | 3 | 0.2% Formula II; Extra-large 35 μm particles in suspension | 2 mg/mL | 30 μL/ eye/dose | QD for 4 Days | 1 hr post dose on Day 5 |
| 9 | I | 3 | 0.4% Formula II; Extra-large 35 μm + HPBCD in suspension | 4 mg/mL | 30 μL/ eye/dose | QD for 4 Days | 1 hr post dose on Day 5 |
| 10 | J | 3 | 0.3% Compound-I; Tris; Particles in suspension | 3 mg/mL | 30 μL/ eye/dose | QD for 4 Days | 1 hr post dose on Day 5 |
| 11 | K | 3 | 0.3% Compound-I; Tris + HPBCD; Particles in suspension | 3 mg/mL | 30 μL/ eye/dose | QD for 4 Days | 1 hr post dose on Day 5 |
| 12 | L | 3 | 0.4% Formula II; HPMC; 0.3 μM Vit K3; Extra-large particles in suspension | 4 mg/mL | 30 μL/ eye/dose | QD for 4 Days | 1 hr post dose on Day 5 |
| 13 | M | 3 | 0.4% Formula II; HPMC; 1.0 μM Vit K3; Extra-large particles in suspension | 4 mg/mL | 30 μL/ eye/dose | QD for 4 Days | 1 hr post dose on Day 5 |

[a]A single dose will be administered on Day 5.
QD - Once daily,
TID - Three times daily,
QID - Four times daily Ocular sampling occurred one hour following the first daily dose on Day 5 for all groups. Whole blood samples using $K_2$EDTA as an anticoagulant were collected from all animals on Day 5, 1 hour post dose. The whole blood was placed on ice until samples were spun in a centrifuge to separate the plasma. Aqueous humor, conjunctiva, cornea, central retina, peripheral retina, central choroid, and peripheral choroid samples were collected following necropsy. Samples were then frozen at −70° C. or lower. All Groups 1-13 plasma, central retina, central choroid, and cornea samples were assayed.

For all dosing groups, ocular tissue concentrations of Formula II or Compound-I assessed on Day 5 were in descending order highest: in the cornea>>central choroid>central retina (Table 16-2). The highest cornea concentrations of Formula II or Compound-I were seen in Group 1. The lowest cornea concentrations of Formula II or Compound-I were seen in Group 3. In general, higher central retina and central choroid concentrations were associated with higher cornea concentrations of Formula II or Compound-I. No advantage of other formulations over Formula II or Compound-I ophthalmic solution was seen with respect to a reduction in cornea concentrations or an increase in central retina or central choroid concentrations of Formula II or Compound-I.

TABLE 16-2

| Group | Plasma* (μM) | Central Retina (μM) | Central Choroid (μM) | Cornea (μM) |
|---|---|---|---|---|
| 1 | 0.00792 | 0.0858 | 0.170 | 16.4 |
| 2 | 0.00284 | 0.0387 | 0.0757 | 11.9 |
| 3 | <LLOQ | 0.00868 | 0.0299 | 1.01 |
| 4 | <LLOQ | 0.00934 | <LLOQ | 1.18 |
| 5 | 0.00257 | 0.0346 | 0.0787 | 16.1 |
| 6 | 0.00451 | 0.0481 | 0.118 | 8.25 |
| 7 | 0.00223 | 0.0570 | 0.108 | 3.38 |
| 8 | <LLOQ | 0.0208 | 0.0598 | 2.09 |
| 9 | 0.00280 | 0.0217 | 0.0581 | 3.43 |
| 10 | 0.00271 | 0.0597 | 0.195 | 3.90 |
| 11 | 0.00440 | 0.0532 | 0.145 | 3.98 |
| 12 | 0.00202 | 0.0204 | 0.0582 | 3.79 |
| 13 | 0.00193 | 0.0248 | 0.0700 | 3.08 |

*Average based on n = 3
Plasma LLOQ = 0.00188 μM
Central Retina LLOQ = 0.00751 μM
Central Choroid LLOQ = 0.0282 μM
Cornea LLOQ = 0.0376 μM Gross ocular examinations using the Draize scale for scoring ocular irritation were performed on all animals prior to the first dose on each day during the study. All formulations were well tolerated. In addition, animals were observed for general health pre-study, during dosing, and at necropsy. All animals assigned to study were normal. Necropsy evaluations consisted of observations in addition to those already noted on Draize Score sheets and Ophthalmologic Exam forms. For all formulations, dosing observations were assessed using the Draize ocular irritation scoring system. The following abnormal observations were noted throughout the duration of the study: animals in Groups 7, 9, 10, 11, 12, and 13 experienced increased blinking following dosing throughout various days of the study; one animal in Group 11 exhibited Discharge Level 1 on Day 3.

Example 20-3

Ocular Pharmacokinetics of Formulations of the Application in Dutch Belted Rabbits A non-GLP study was conducted to assess the ocular pharmacokinetics of a first active agent of the present application (e.g., Formula II or Compound-I), in suspension, when administered one, two, or three times daily, as a topical instillation, to both eyes of Dutch Belted rabbits for four days. The study design (Table 17-1) consisted of thirty-nine (39) Dutch Belted rabbits, each receiving a 30 μL bilateral topical ocular dose. Various suspension formulations of the present application were evaluated and compared against two control formulations: a) a cyclodextrin-based eye drops solution (Control Group 13, Table 17-1), and b) a pilot suspension formulation used in previous rabbit pharmacokinetic studies, (Group 10, Table 17-1). A comparison of the formulation variables for each suspension listed in Table 17-1 is provided in Table 17-2. Formula II or Compound-I was used in the test suspensions, whereas the Eye Drops solution formulation is derived with the Compound-I.

TABLE 17-1

Study design

| Group | | No. of Rabbits | Test Article Formulation | Conc. | Dose Volume | Dosing Frequency and Duration[a] | Sample Time Points |
|---|---|---|---|---|---|---|---|
| 1 | A | 3 | Formula II; Pluronic; 35 μm particles | 0.3 mg/mL | 30 μL/ eye/dose | BID for 4 Days | 1 hr post dose on Day 5 |
| 2 | B | 3 | Formula II; Pluronic; 35 μm particles | 0.3 mg/mL | 30 μL/ eye/dose | TID for 4 Days | 1 hr post dose on Day 5 |
| 3 | C | 3 | Formula II; HPMC; 35 μm particles | 4 mg/mL | 30 μL/ eye/dose | QD for 4 Days | 1 hr post dose on Day 5 |
| 4 | D | 3 | Formula II; Pluronic; 35 μm particles (Control) | 4 mg/mL | 30 μL/ eye/dose | QD for 4 Days | 1 hr post dose on Day 5 |
| 5 | E | 3 | Formula II; HPMC; 50-60 μm particles | 4 mg/mL | 30 μL/ eye/dose | QD for 4 Days | 1 hr post dose on Day 5 |
| 6 | F | 3 | Formula II; Pluronic; 50-60 μm particles | 4 mg/mL | 30 μL/ eye/dose | QD for 4 Days | 1 hr post dose on Day 5 |
| 7 | G | 3 | Formula II; PVP; 50-60 μm particles | 4 mg/mL | 30 μL/ eye/dose | QD for 4 Days | 1 hr post dose on Day 5 |
| 8 | H | 3 | Formula II; HPMC; 1.0 μM Vit K3; 50-60 μm particles | 4 mg/mL | 30 μL/ eye/dose | QD for 4 Days | 1 hr post dose on Day 5 |
| 9 | I | 3 | Formula II; Pluronic; 1.0 μM Vit K3; 50-60 μm particles | 4 mg/mL | 30 μL/ eye/dose | QD for 4 Days | 1 hr post dose on Day 5 |
| 10 | J | 3 | Compound-I; Tris; 50-60 μm particles (Control) | 4 mg/mL | 30 μL/ eye/dose | QD for 4 Days | 1 hr post dose on Day 5 |
| 11 | K | 3 | Compound-I; Tris + Tween80; 50-60 μm particles | 4 mg/mL | 30 μL/ eye/dose | QD for 4 Days | 1 hr post dose on Day 5 |
| 12 | L | 3 | Compound-I; Tris + HPMC; 50-60 μm particles | 4 mg/mL | 30 μL/ eye/dose | QD for 4 Days | 1 hr post dose on Day 5 |
| 13 | M | 3 | Compound-I; Ophthalmic Solution | 4 mg/mL | 30 μL/ eye/dose | QD for 4 Days | 1 hr post dose on Day 5 |

[a]A single dose will be administered on Day 5.
QD - Once daily,
BID - Twice daily,
TID - Three times daily

TABLE 17-2

| Group # | 1 and 2 | 3 | 4 | 5 | 6 | 7 | 8 | 9 | 10 | 11 | 12 |
|---|---|---|---|---|---|---|---|---|---|---|---|
| Dose-strength | 0.3 mg/mL | 4 mg/mL | 4 mg/mL | 4 mg/mL | 4 mg/mL | 4 mg/mL | 4 mg/mL | 4 mg/mL | 4* mg/mL | 4* mg/mL | 4* mg/mL |
| API Form | Free Base | Free Base | Free Base | Free Base | Free Base | Free Base | Free Base | Free Base | HCl Salt | HCl Salt | HCl Salt |
| Particle size (μm) | 35 | 35 | 35 | 50-60 | 50-60 | 50-60 | 35 | 35 | 50-60 | 50-60 | 50-60 |
| Stabilizer | Pluronic | HPMC | Pluronic | HPMC | Pluronic | PVP | HPMC | Pluronic | Tris | Tris + Tween 80 | Tris + HPMC |
| Vitamin K3 (μM) | — | — | — | — | — | — | 1 | 1 | — | — | — |
| NOTES | 2X volume for BID & TID dosing frequencies | QD | QD (control) | QD | QD | QD | QD | QD | QD (control) | QD | QD |

*Note:
requires 4.3 mg/mL of HCl salt to provide 4 mg/mL of Free Base

Ocular sampling occurred one hour following the first daily dose on Day 5 for all groups. Whole blood samples using K$_2$EDTA as an anticoagulant were collected from all animals on Day 5, 1 hour post dose. The whole blood was placed on ice until samples were spun in a centrifuge to separate the plasma. Aqueous humor, conjunctiva, cornea, central retina, peripheral retina, central choroid, and peripheral choroid samples were collected following necropsy. Samples were then frozen at −70° C. or lower. For all Groups 1-13, plasma, central retina, central choroid, and cornea samples were assayed.

Ocular tissue concentrations of Formula II or Compound-I assessed on Day 5 were in descending order: highest in the cornea>>central choroid>central retina. Corneal concentrations of Formula II or Compound-I ranged from 1.5 to 14.7 μM with the highest concentrations being observed in Group 13 and the lowest in Group 1. All suspension formulations, Groups 1-12, provided lower average corneal concentrations as compared to the Eye Drops solution control, Group 13. These observations did not seem to be influenced by the presence or absence of Vitamin K$_3$/menadione in the suspension formulation. Central choroid concentrations ranged from <0.028 to 0.27 μM with the highest concentrations seen in Groups 11 and the lowest in Group 2. Central retina concentrations ranged from 0.009 to 0.069 μM; Group 11 had the highest central retina concentrations and Group 1 had the lowest central retina concentrations. Plasma concentrations of Formula II or Compound-I were very low being approximately 10-fold and 100-fold lower than those in the central retina and central choroid, respectively. See Table 17-3.

TABLE 17-3

| Group | Plasma* (μM) | Central Retina (μM) | Central Choroid (μM) | Cornea (μM) |
|---|---|---|---|---|
| 1 | <LLOQ | 0.00881 | 0.0319 | 1.50 |
| 2 | <LLOQ | 0.00884 | <LLOQ | 1.73 |
| 3 | 0.00205 | 0.0228 | 0.0767 | 4.38 |
| 4 | 0.00220 | 0.0305 | 0.0684 | 5.08 |
| 5 | <LLOQ | 0.0221 | 0.0558 | 3.31 |
| 6 | <LLOQ | 0.0279 | 0.101 | 4.82 |
| 7 | 0.00331 | 0.0282 | 0.0876 | 5.23 |
| 8 | 0.00257 | 0.0540 | 0.0844 | 4.05 |
| 9 | 0.00256 | 0.0344 | 0.0828 | 5.64 |
| 10 | 0.00623 | 0.0632 | 0.191 | 6.20 |
| 11 | 0.00410 | 0.0691 | 0.265 | 8.67 |
| 12 | 0.00470 | 0.0482 | 0.116 | 5.82 |
| 13 | 0.00416 | 0.0570 | 0.112 | 14.7 |

TABLE 17-3-continued

| Group | Plasma* (μM) | Central Retina (μM) | Central Choroid (μM) | Cornea (μM) |
|---|---|---|---|---|

*Average based on n = 3
Plasma LLOQ = 0.00188 μM
Central Retina LLOQ = 0.00751 μM
Central Choroid LLOQ = 0.0282 μM
Cornea LLOQ = 0.0376 μM Additionally, Vitamin K3 concentrations were determined in plasma, central retina, central choroid, and cornea samples for animals from Groups 8 and 9. A calibration curve prepared in control matrix was used to determine the concentration of Vitamin K3. See Table 17-4.

TABLE 17-4

| Group | Plasma* (μM) | Central Retina (μM) | Central Choroid (μM) | Cornea (μM) |
|---|---|---|---|---|
| 8 | <LLOQ | 15.4 | <LLOQ | <LLOQ |
| 9 | 0.465 | <LLOQ | <LLOQ | <LLOQ |

*Average based on n = 3
Plasma LLOQ = 0.291 μM
Central Retina LLOQ = 11.6 μM
Central Choroid LLOQ = 43.6 μM
Cornea LLOQ = 2.91 μM Gross ocular examinations using the Draize scale for scoring ocular irritation were performed on all animals prior to the first dose on each day during the study. All formulations were well tolerated, with the exception that for one animal in Group 11 on Day 4 of dosing, where conjunctival chemosis was noted, and for one animal in Group 12 on Day 4 of dosing, where conjunctival redness was noted. In addition, animals were observed for general health pre-study, during dosing, and at necropsy. All animals assigned to study were normal. Necropsy evaluations consisted of observations in addition to those already noted on Draize Score sheets. For all formulations, dosing observations were assessed using the Draize ocular irritation scoring system. The following abnormal observations were noted throughout the duration of the study: animals in Groups 4, 6, 7, 8, 9, and 11 experienced increased blinking following dosing throughout various days of the study; one animal in Group 4 exhibited Redness Level 1 in both eyes and Chemosis Level 1 in the left eye prior to necropsy on Day 5; and one animal in Group 5 exhibited Chemosis Level 1 in the right eye prior to necropsy on Day 5.

Example 20-5

Ocular Pharmacokinetics of Formulations of the Application in Dutch Belted Rabbits A non-GLP study was conducted to assess the ocular pharmacokinetics of a first active agent of the present application (e.g., Formula II or Compound-I), in suspension, when administered one or two times daily, as a topical instillation, to both eyes of Dutch Belted rabbits for four days. The study design (Table 18-1) consisted of forty-nine (49) Dutch Belted rabbits, each receiving a 30 μL bilateral topical ocular dose. Various suspension formulations of the present application were evaluated and compared against a cyclodextrin-based eye drops solution (Control Groups 2 and 3, Table 18-1). A comparison of the formulation variables for each suspension listed in Table 18-1 is provided in Table 18-2. Formula II or Compound-I was used in the test suspensions, whereas the Eye Drops solution formulation is derived with Compound-I.

TABLE 18-1

| Group | | No. of Rabbits | Test Article Formulation | Conc. | Dose Volume | Dosing Frequency and Duration[a] | Sample Time Points |
|---|---|---|---|---|---|---|---|
| 1 | A | 3 | Compound-I; Ophthalmic Solution, pH 6 | 0.3 mg/mL | 30 μL/eye/dose | BID for 4 Days | 1 hr post dose on Day 5 |
| 2 | B | 4 | Compound-I; Ophthalmic Solution, pH 6 (Control) | 1 mg/mL | 30 μL/eye/dose | QD for 4 Days | 1 hr post dose on Day 5 |
| 3 | C | 3 | Compound-I; Ophthalmic Solution, pH 6 (Control) | 4 mg/mL | 30 μL/eye/dose | QD for 4 Days | 1 hr post dose on Day 5 |
| 4 | D | 3 | Formula II; 0.08% HPMC + 2.5% Glycerol + 0.2% HEC; 1.0 uM Vit K3; 30 μm particles, pH ~7.5 | 4 mg/mL | 30 μL/eye/dose | QD for 4 Days | 1 hr post dose on Day 5 |
| 5 | E | 3 | Formula II; 0.08% HPMC + 2.5% Glycerol + 0.2% HEC; 1.0 uM Vit K3; 30 μm particles, pH 6 | 6 mg/mL | 30 μL/eye/dose | QD for 4 Days | 1 hr post dose on Day 5 |
| 6 | F | 3 | Compound-I; 0.6% TRIS + 0.08% HPMC + 2.0% Glycerol + 0.2% HEC; 1.0 uM Vit K3; 30 μm particles, pH ~7.5 | 6 mg/mL | 30 μL/eye/dose | QD for 4 Days | 1 hr post dose on Day 5 |
| 7 | G | 3 | Compound-I; 0.6% Tris + 2.0% Glycerol + 0.3% HEC + 0.04% Tylox; 1.0 uM Vit K3; 30 μm particles, pH 6 | 4.3 mg/mL | 30 μL/eye/dose | QD for 4 Days | 1 hr post dose on Day 5 |
| 8 | H | 3 | Compound-I; 0.6% Tris + 2.0% Glycerol + 0.2% HEC + 0.04% Tylox; 1.0 uM Vit K3; 30 μm particles, pH 6 | 4.3 mg/mL | 30 μL/eye/dose | QD for 4 Days | 1 hr post dose on Day 5 |
| 9 | I | 3 | Compound-I; 0.6% Tris + 2.0% Glycerol + 0.3% HEC + 0.04% Tylox; 1.0 uM Vit K3; 30 μm particles, pH 7 | 4.3 mg/mL | 30 μL/eye/dose | QD for 4 Days | 1 hr post dose on Day 5 |
| 10 | J | 3 | Compound-I; 0.6% Tris + 2.0% Glycerol + 0.2% HEC + 0.04% Tylox; 1.0 uM Vit K3; 30 μm particles, pH 7 | 4.3 mg/mL | 30 μL/eye/dose | QD for 4 Days | 1 hr post dose on Day 5 |
| 11 | K | 3 | Compound-I; 0.6% Tris + 2.0% Glycerol + 0.3% HEC + 0.08% HPMC; 1.0 uM Vit K3; 30 μm particles, pH 6 | 4.3 mg/mL | 30 μL/eye/dose | QD for 4 Days | 1 hr post dose on Day 5 |
| 12 | L | 3 | Compound-I; 0.6% Tris + 2.0% Glycerol + 0.2% HEC + 0.08% HPMC; 1.0 uM Vit K3; 30 μm particles, pH 6 | 4.3 mg/mL | 30 μL/eye/dose | QD for 4 Days | 1 hr post dose on Day 5 |

TABLE 18-1-continued

| Group | | No. of Rabbits | Test Article Formulation | Conc. | Dose Volume | Dosing Frequency and Duration[a] | Sample Time Points |
|---|---|---|---|---|---|---|---|
| 13 | M | 3 | Compound-I; 0.6% Tris + 2.0% Glycerol + 0.2% HEC + 0.08% HPMC; 1.0 uM Vit K3; Native (~50 μm), pH 6 (Control) | 4.3 mg/mL | 30 μL/ eye/dose | QD for 4 Days | 1 hr post dose on Day 5 |
| 14 | N | 3 | Compound-I; 0.6% Tris + 2.0% Glycerol + 0.2% HEC + 0.08% HPMC; 1.0 uM Vit K3; 3 μm particles, pH 6 | 4.3 mg/mL | 30 μL/ eye/dose | QD for 4 Days | 1 hr post dose on Day 5 |
| 15 | O | 3 | Compound-I; 0.6% Tris + 2.0% Glycerol + 0.3% HEC + 0.08% HPMC; 1.0 uM Vit K3; 30 μm particles, pH 7 | 4.3 mg/mL | 30 μL/ eye/dose | QD for 4 Days | 1 hr post dose on Day 5 |
| 16 | P | 3 | Compound-I; 0.6% Tris + 2.0% Glycerol + 0.2% HEC + 0.08% HPMC; 1.0 uM Vit K3; 30 μm particles, pH 7 | 4.3 mg/mL | 30 μL/ eye/dose | QD for 4 Days | 1 hr post dose on Day 5 |

[a] A single dose will be administer on Day 5;
QD - Once daily,
BID - Twice daily

TABLE 18-2

| Group # | 1 | 2 | 3 | 4 | 5 | 6 | 7 | 8 | 9 |
|---|---|---|---|---|---|---|---|---|---|
| Dose strength (mg/mL) | 0.3 | 1 | 4 | 4 | 6 | 6 | 4* | 4* | 4* |
| API Form | Salt | Salt | Salt | FB | FB | Salt | Salt | Salt | Salt |
| Approx. PSD (μm) | — | — | — | 30/XL | 30/XL | 30/XL | 30/XL | 30/XL | 30/XL |
| % Stabilizer | — | — | — | HPMC 0.08% | HPMC 0.08% | TRIS 0.60% | TRIS 0.60% | TRIS 0.60% | TRIS 0.60% |
| % Glycerol | — | — | — | 2.5 | 2.5 | 2 | 2 | 2 | 2 |
| % HEC | — | — | — | 0.2 | 0.2 | 0.2 | 0.3 | 0.2 | 0.3 |
| Add'l Excipient | — | — | — | — | — | HPMC 0.08% | Tylox 0.04% | Tylox 0.04% | Tylox 0.04% |
| VitK3 (μM) | — | — | — | 1 | 1 | 1 | 1 | 1 | 1 |
| pH | 6 | 6 | 6 | ≈7.5 | ≈7.5 | 6 | 6 | 6 | 7 |
| Frequency | BID | QD | QD Control | QD | QD | QD | QD | QD | QD |

| Group # | 10 | 11 | 12 | 13 | 14 | 15 | 16 |
|---|---|---|---|---|---|---|---|
| Dose strength (mg/mL) | 4* | 4* | 4* | 4* | 4* | 4* | 4* |
| API Form | Salt | Salt | Salt | Salt | Salt | Salt | Salt |
| Approx. PSD (μm) | 30/XL | 30/XL | 30/XL | Native (≈50)/XXL | 3/Large | 30/XL | 30/XL |
| % Stabilizer | TRIS 0.60% | TRIS 0.60% | TRIS 0.60% | TRIS 0.60% | TRIS 0.60% | TRIS 0.60% | TRIS 0.60% |
| % Glycerol | 2 | 2 | 2 | 2 | 2 | 2 | 2 |
| % HEC | 0.2 | 0.3 | 0.2 | 0.2 | 0.2 | 0.3 | 0.2 |
| Add'l Excipient | Tylox 0.04% | HPMC 0.08% | HPMC 0.08% | HPMC 0.08% | HPMC 0.08% | HPMC 0.08% | HPMC 0.08% |
| VitK3 (μM) | 1 | 1 | 1 | 1 | 1 | 1 | 1 |
| pH | 7 | 6 | 6 | 6 | 6 | 7 | 7 |
| Frequency | QD | QD | QD | QD Control Suspension | QD | QD | QD |

Ocular sampling occurred one hour following the first daily dose on Day 5 for all groups. Whole blood samples using K₂EDTA as an anticoagulant were collected from all animals on Day 5, 1 hour post dose. The whole blood was placed on ice until samples were spun in a centrifuge to separate the plasma. Aqueous humor, conjunctiva, cornea, central retina, peripheral retina, central choroid, and peripheral choroid samples were collected following necropsy. Samples were then frozen at −70° C. or lower. For all Groups 1-16, plasma, central retina, central choroid, and cornea samples were assayed for PAN-90806.

Ocular tissue concentrations of Formula II or Compound-I assessed on Day 5 were in descending order: highest in the cornea>>central choroid>central retina. Corneal concentrations of Formula II or Compound-I ranged from 3 to 34 µM with the highest concentrations being observed in Group 9 and the lowest in Group 1. Central choroid concentrations ranged from <0.056 to 0.24 µM with the highest concentrations seen in Groups 6 and 14 and the lowest in Group 1. Central retina concentrations ranged from 0.02 to 0.14 µM; Group 6 had the highest central retina concentrations and Group 1 had the lowest central retina concentrations. Plasma concentrations of Formula II or Compound-I were very low being approximately 5 to 10-fold and 100-fold lower than those in the central retina and central choroid, respectively. See Table 18-3.

TABLE 18-3

| Group | Plasma (µM) | Central Retina (µM) | Central Choroid (µM) | Cornea (µM) |
|---|---|---|---|---|
| 1 | <LLOQ | 0.0163 | <LLOQ | 3.33 |
| 2 | 0.00267 | 0.0347 | 0.106 | 7.06 |
| 3 | 0.00450 | 0.0837 | 0.181 | 15.9 |
| 4 | 0.00327 | 0.0384 | 0.203 | 21.3 |
| 5 | 0.00391 | 0.0479 | 0.203 | 23.8 |
| 6 | 0.00998 | 0.136 | 0.243 | 14.4 |
| 7 | 0.00556 | 0.0697 | 0.142 | 9.68 |
| 8 | 0.00662 | 0.0901 | 0.152 | 11.3 |
| 9 | 0.00738 | 0.102 | 0.224 | 34.4 |
| 10 | 0.00528 | 0.0502 | 0.166 | 11.1 |
| 11 | 0.00465 | 0.0796 | 0.154 | 12.8 |
| 12 | 0.00366 | 0.0490 | 0.137 | 7.05 |
| 13 | 0.00524 | 0.0677 | 0.234 | 7.82 |
| 14 | 0.00499 | 0.0992 | 0.241 | 20.7 |
| 15 | 0.00325 | 0.0532 | 0.200 | 18.2 |
| 16 | 0.00523 | 0.0744 | 0.208 | 14.7 |

Plasma LLOQ = 0.00188 µM
Central Retina LLOQ = 0.00751 µM
Central Choroid LLOQ = 0.0563 µM
Cornea LLOQ = 0.0188 µM Gross ocular examinations using the Draize scale for scoring ocular irritation were performed on all animals prior to the first dose on each day during the study. All formulations were well tolerated. In addition, animals were observed for general health pre-study, during dosing, and at necropsy. All animals assigned to study were normal. Necropsy evaluations consisted of observations in addition to those already noted on Draize Score sheets. For all formulations, dosing observations were assessed using the Draize ocular irritation scoring system and are summarized below. No abnormal observations were noted.

Example 20-4

Ocular Pharmacokinetics of Formulations of the Application in Dutch Belted Rabbits A non-GLP study was conducted to assess the ocular pharmacokinetics of a first active agent of the present application (e.g., Formula II or Compound-I), in suspension, when administered one or two times daily, as a topical instillation, to both eyes of Dutch Belted rabbits for four days. The study design (Table 19-1) consisted of forty-seven (47) Dutch Belted rabbits, each receiving a 30 µL bilateral topical ocular dose. Various suspension formulations of the present application were evaluated and compared against a cyclodextrin-based eye drops solution (Control Group 1, Table 19-1). A comparison of the formulation variables for each suspension listed in Table 19-1 is provided in Table 19-2. Formula II or Compound-I was used in the test suspensions as well as the Eye Drops solution. However, different batches of Compound-I were tested in certain suspensions (Groups 13, 14, and 15, Table 19-1).

TABLE 19-1

| Group | | No. of Rabbits | Test Article Formulation | Conc. | Dose Volume | Dosing Frequency and Duration[a] | Sample Time Points |
|---|---|---|---|---|---|---|---|
| 1 | A | 3 | Compound-I; Ophthalmic Solution, pH 6 (Control) | 4 mg/mL | 30 µL/ eye/dose | QD for 4 days | 1 hr post dose on Day 5 |
| 2 | B | 4 | Compound-I; HPMC; 30 µm particles | 4 mg/mL | 30 µL/ eye/dose | QD for 4 days | 1 hr post dose on Day 5 |
| 3 | C | 3 | Compound-I; HPMC; 3 µm particles | 4 mg/mL | 30 µL/ eye/dose | QD for 4 days | 1 hr post dose on Day 5 |
| 4 | D | 4 | Compound-I; HPMC; 50 µm particles (Control) | 4 mg/mL | 30 µL/ eye/dose | QD for 4 days | 1 hr post dose on Day 5 |
| 5* | E | 3 | Compound-I; HPMC; 30 µm particles (Control)* | 4 mg/mL | 30 µL/ eye/dose | QD for 4 days | 1 hr post dose on Day 5 |
| 6 | F | 3 | Compound-I; HPMC; 50 µm particles | 4 mg/mL | 30 µL/ eye/dose | BID for 4 days | 1 hr post dose on Day 5 |
| 7 | G | 3 | Compound-I; HPMC; 50 µm particles | 1 mg/mL | 30 µL/ eye/dose | QD for 4 days | 1 hr post dose on Day 5 |

TABLE 19-1-continued

| Group | | No. of Rabbits | Test Article Formulation | Conc. | Dose Volume | Dosing Frequency and Duration[a] | Sample Time Points |
|---|---|---|---|---|---|---|---|
| 8 | H | 3 | Compound-I; HPMC; 50 μm particles | 1 mg/mL | 30 μL/ eye/dose | BID for 4 days | 1 hr post dose on Day 5 |
| 9 | I | 3 | Compound-I; HPMC; 50 μm particles | 2 mg/mL | 30 μL/ eye/dose | QD for 4 days | 1 hr post dose on Day 5 |
| 10 | J | 3 | Compound-I; HPMC; 50 μm particles | 2 mg/mL | 30 μL/ eye/dose | BID for 4 days | 1 hr post dose on Day 5 |
| 11 | K | 3 | Compound-I; HPMC; 50 μm particles | 6 mg/mL | 30 μL/ eye/dose | QD for 4 days | 1 hr post dose on Day 5 |
| 12 | L | 3 | Compound-I; HPMC; 50 μm particles | 10 mg/mL | 30 μL/ eye/dose | QD for 4 days | 1 hr post dose on Day 5 |
| 13 | M | 3 | Compound-I; HPMC; 50 μm particles | 4 mg/mL | 30 μL/ eye/dose | QD for 4 days | 1 hr post dose on Day 5 |
| 14 | N | 3 | Compound-I; HPMC; 50 μm particles | 4 mg/mL | 30 μL/ eye/dose | QD for 4 days | 1 hr post dose on Day 5 |
| 15 | O | 3 | Compound-I; HPMC; 50 μm particles | 4 mg/mL | 30 μL/ eye/dose | QD for 4 days | 1 hr post dose on Day 5 |

[a] A single dose will be administer on Day 5
*Sampled analyzed for Vitamin K3
QD - Once daily,
BID - Twice daily

TABLE 19-2

| Group # | 1 | 2 | 3 | 4 | 5 | 6 | 7 |
|---|---|---|---|---|---|---|---|
| N | 3 | 4 | 2 | 4 | 3 | 3 | 3 |
| Dose strength (mg/mL) | 4 | 4* | 4* | 4* | 4* | 4* | 1 |
| Approx. PSD (μm) | — | 30 | 3 | Native (≈50) | Native (≈50) | Native (≈50) | Native (≈50) |
| % Stabilizer | — | TRIS 0.60% | TRIS 0.60% | TRIS 0.60% | TRIS 0.60% | TRIS 0.60% | TRIS 0.60% |
| % Glycerol | — | 2 | 2 | 2 | 2 | 2 | 2 |
| % HEC | — | 0.2 | 0.2 | 0.2 | 0.2 | 0.2 | 0.2 |
| Add'l Excip. | — | HPMC 0.08% | HPMC 0.08% | HPMC 0.08% | HPMC 0.08% | HPMC 0.08% | HPMC 0.08% |
| Vitamin K3 (μM) | — | 1 | 1 | 1 | 1 | 1 | 1 |
| pH | 6 | 6 | 6 | 6 | 6 | 6 | 6 |
| Dose Freq. | QD Control | QD | QD | QD Suspension control | QD Suspension control | BID | QD |

| Group # | 8 | 9 | 10 | 11 | 12 | 13 | 14 | 15 |
|---|---|---|---|---|---|---|---|---|
| N | 3 | 3 | 3 | 3 | 3 | 3 | 3 | 3 |
| Dose strength (mg/mL) | 1 | 2 | 2 | 6 | 10 | 4* | 4* | 4* |
| Approx. PSD (μm) | Native (≈50) | Native (≈50) | Native (≈50) | Native (≈50) | Native (≈50) | Native (≈50) | Native (≈50) | Native (≈50) |
| % Stabilizer | TRIS 0.60% | TRIS 0.60% | TRIS 0.60% | TRIS 0.60% | TRIS 0.60% | TRIS 0.60% | TRIS 0.60% | TRIS 0.60% |
| % Glycerol | 2 | 2 | 2 | 2 | 2 | 2 | 2 | 2 |
| % HEC | 0.2 | 0.2 | 0.2 | 0.2 | 0.2 | 0.2 | 0.2 | 0.2 |

TABLE 19-2-continued

| Add'l Excip. | HPMC 0.08% | HPMC 0.08% | HPMC 0.08% | HPMC 0.08% | HPMC 0.08% | HPMC 0.08% | HPMC 0.08% | HPMC 0.08% |
|---|---|---|---|---|---|---|---|---|
| Vitamin K3 (µM) | 1 | 1 | 1 | 1 | 1 | 1 | 1 | 1 |
| pH | 6 | 6 | 6 | 6 | 6 | 6 | 6 | 6 |
| Dose Freq. | BID | QD | BID | QD | QD | QD | QD | QD |

*4 mg/mL = 0.43% in salt form

Ocular sampling occurred one hour following the first daily dose on Day 5 for all groups. Whole blood samples using $K_2$EDTA as an anticoagulant were collected from all animals on Day 5, 1 hour post dose. The whole blood was placed on ice until samples were spun in a centrifuge to separate the plasma. Aqueous humor, conjunctiva, cornea, central retina, peripheral retina, central choroid, and peripheral choroid samples were collected following necropsy. Samples were then frozen at −70° C. or lower. For all Groups 1-15, plasma, central retina, central choroid, and cornea samples were assayed. For Group 5 only, samples were analyzed for Vitamin K3.

Ocular tissue concentrations of Formula II or Compound-I assessed on Day 5 1 hour after the first dose were in descending order: highest in the cornea>>central choroid>central retina. Corneal concentrations of Formula II or Compound-I ranged from 1 to 25 µM with the highest concentrations being observed in Group 12 and the lowest in Group 7. Central choroid concentrations ranged from 0.06 to 0.2 µM with the highest concentrations seen in Groups 12 and 14 and the lowest in Group 7. Central retina concentrations ranged from 0.03 to 0.1 µM; Group 12 had the highest central retina concentrations and Group 7 had the lowest central retina concentrations. Plasma concentrations of Formula II or Compound-I were very low being approximately 10-fold and 100-fold lower than those in the central retina and central choroid, respectively. See Table 19-3.

TABLE 19-3

| Group | Plasma (µM) | Central Retina (µM) | Central Choroid (µM) | Cornea (µM) |
|---|---|---|---|---|
| 1 | 0.00428 | 0.0551 | 0.129 | 14.3 |
| 2 | 0.00464 | 0.0506 | 0.135 | 7.48 |
| 3 | 0.00704 | 0.0928 | 0.159 | 10.2 |
| 4 | 0.00598 | 0.0735 | 0.128 | 3.93 |
| 5 | 0.00626 | 0.0442 | 0.129 | 4.47 |
| 6 | 0.00415 | 0.0441 | 0.199 | 6.41 |
| 7 | 0.00218 | 0.0256 | 0.0590 | 1.24 |
| 8 | 0.00211 | 0.0342 | 0.0708 | 1.72 |
| 9 | 0.00405 | 0.0634 | 0.0908 | 2.28 |
| 10 | 0.00376 | 0.0507 | 0.116 | 5.00 |
| 11 | 0.00772 | 0.0915 | 0.148 | 7.07 |
| 12 | 0.00861 | 0.114 | 0.199 | 24.7 |
| 13 | 0.00709 | 0.0766 | 0.151 | 8.55 |
| 14 | 0.00268 | 0.0384 | 0.203 | 3.88 |
| 15 | 0.00469 | 0.0630 | 0.196 | 4.23 |

Plasma LLOQ = 0.00188 µM
Central Retina LLOQ = 0.00751 µM
Central Choroid LLOQ = 0.0563 µM
Cornea LLOQ = 0.0376 µM An analytical method for the analysis of Vitamin K3 was determined in plasma, central retina, central choroid, and cornea samples from Group 5 animals. A calibration curve prepared in control vitreous humor was used to determine the concentration of Vitamin K3. Internal standard (IS) responses were inconsistent for the central choroid and plasma samples. Thus, positive plasma results were likely due to the reduced IS response. The Vitamin K3 response in plasma was similar to background levels. Central choroid samples had a positive Vitamin K3 response, but the reduced IS response made quantitative results suspect. Central retina and cornea samples had a normal IS response and no quantitative results for Vitamin K3. See Table 19-4.

TABLE 19-4

| Group | Plasma (µM) | Central Retina (µM) | Central Choroid (µM) | Cornea (µM) |
|---|---|---|---|---|
| 5 | 0.0923 | <LLOQ | 12.4 | <LLOQ |

Plasma LLOQ = 0.0145 µM
Central Retina LLOQ = 0.581 µM
Central Choroid LLOQ = 2.18 µM
Cornea LLOQ = 0.145 µM Gross ocular examinations using the Draize scale for scoring ocular irritation were performed on all animals prior to the first dose on each day during the study. In general, formulations were well tolerated, with the exception of two animals in Group 6 on Day 4 of dosing, where conjunctival chemosis was noted, one animal in Group 8 on Day 3, where conjunctival discharge was noted, one animal in Group 10 on Day 5 of dosing, where conjunctival chemosis and discharge were noted, one animal in Group 13, and one animal in Group 14 on Day 5 of dosing, where conjunctival chemosis was noted. In addition, animals were observed for general health pre-study, during dosing, and at necropsy. All animals assigned to study were normal. Necropsy evaluations consisted of observations in addition to those already noted on Draize Score sheets. For all formulations, dosing observations were assessed using the Draize ocular irritation scoring system. The following clinical observations were noted throughout the study: one animal in Group 8 exhibited discharge in the left eye during the dose on Day 3. Animals in Group 12 exhibited chemosis in both eyes at the time of necropsy.

Example 21

Preparation of Particles Comprising Formula II

The suspension formulations comprising particles of Formula II were prepared by roller milling. Large particles were produced using larger milling media (e.g., 3 mm in diameter) for a short period of time at low roller speed (FIG. 9B). Nanoparticles were produced using smaller media (e.g., 0.8 mm in diameter) for a longer period of time at a high roller speed (FIG. 9A). The two concentrations of Formula II (i.e., 0.4% and 0.2%) were diluted from a 5% API stock with a glycerol solution to obtain the proper tonicity. Best clean precautions included autoclaving of product contact parts, filtration of excipient solutions and transfers using prepackaged sterile supplies. In addition, all transfers were within a laminar flow hood in a Clean Room area.

Additional examples of particles comprising Formula II or Compound-I is shown in Tables 21 and 22.

TABLE 21

| Form. II or Cmpd-I Conc. | API Form | Formulation Method | Description | PSD |
|---|---|---|---|---|
| 4 mg/mL | Freebase | Milled | 0.08% HPMC, 2.5% Glycerol, 0.2% HEC, 1.0 uM Vitamin K3, pH 7.5 | 30 um |
| 6 mg/mL | Freebase | Milled | 0.08% HPMC, 2.5% Glycerol, 0.2% HEC, 1.0 uM Vitamin K3, pH 7.5 | 30 um |
| 6 mg/mL | HCl Salt | Milled | 0.6% Tris, 0.08% HPMC, 2.0% Glycerol, 0.2% HEC, 1.0 uM Vitamin K3, pH 6.0 | 30 um |
| 4.3 mg/mL | HCl Salt | Milled | 0.6% Tris, 2.0% Glycerol, 0.3% HEC, 0.04% Tyloxapol, 1.0 uM Vitamin K3, pH 6.0 | 30 um |
| 4.3 mg/mL | HCl Salt | Milled | 0.6% Tris, 2.0% Glycerol, 0.2% HEC, 0.04% Tyloxapol, 1.0 uM Vitamin K3, pH 6.0 | 30 um |
| 4.3 mg/mL | HCl Salt | Milled | 0.6% Tris, 2.0% Glycerol, 0.3% HEC, 0.04% Tyloxapol, 1.0 uM Vitamin K3, pH 7.0 | 30 um |
| 4.3 mg/mL | HCl Salt | Milled | 0.6% Tris, 2.0% Glycerol, 0.2% HEC, 0.04% Tyloxapol, 1.0 uM Vitamin K3, pH 7.0 | 30 um |
| 4.3 mg/mL | HCl Salt | Milled | 0.6% Tris, 2.0% Glycerol, 0.3% HEC, 0.08% HPMC, 1.0 uM Vitamin K3, pH 6.0 | 30 um |
| 4.3 mg/mL | HCl Salt | Milled | 0.6% Tris, 2.0% Glycerol, 0.2% HEC, 0.08% HPMC, 1.0 uM Vitamin K3, pH 6.0 | 30 um |
| 4.3 mg/mL | HCl Salt | Un-milled | 0.6% Tris, 2.0% Glycerol, 0.2% HEC, 0.08% HPMC, 1.0 uM Vitamin K3, pH 6.0 | Native ~50 um |
| 4.3 mg/mL | HCl Salt | Milled | 0.6% Tris, 2.0% Glycerol, 0.2% HEC, 0.08% HPMC, 1.0 uM Vitamin K3, pH 6.0 | 30 um |
| 4.3 mg/mL | HCl Salt | Milled | 0.6% Tris, 2.0% Glycerol, 0.3% HEC, 0.08% HPMC, 1.0 uM Vitamin K3, pH 7.0 | 30 um |
| 4.3 mg/mL | HCl Salt | Milled | 0.6% Tris, 2.0% Glycerol, 0.2% HEC, 0.08% HPMC, 1.0 uM Vitamin K3, pH 7.0 | 30 um |

TABLE 22

| API Form | Excipient | Roller speed | Milling media size | PSD (Particle Size Distribution) | | | Particles under Storage |
|---|---|---|---|---|---|---|---|
| | | | | Median (nm) | Mean (nm) | D90 (nm) | |
| Freebase | Tween 80 | | | ~300 | ~2000 | ~5400 | |
| Freebase | Pluronic F-127 | | | ~4700 | ~5600 | ~9000 | |
| Freebase | Pluronic F-127 | | | ~230 | ~1000 | ~2800 | |
| HCl salt | Tyloxapol | | | ~110 | ~110 | ~160 | |
| Freebase | Tween 80 | low | 3 mm | ~5500 | ~8400 | ~11000 | |
| Freebase | Tween 80 | low | 3 mm | ~3900 | ~4100 | ~6800 | |
| Freebase | Tween 80 | low | 3 mm | ~3700 | ~4000 | ~7000 | |
| Freebase | Tween 80 | low | 3 mm | ~3500 | ~4000 | ~7600 | |
| Freebase | Pluronic F-127 | low | 3 mm | ~6200 | ~8100 | ~12000 | |
| Freebase | Pluronic F-127 | low | 3 mm | ~4400 | ~4700 | ~8100 | |
| Freebase | Pluronic F-127 | | | ~2500 | ~3100 | ~5800 | 6 days, 40° C. |
| HCl salt | Tyloxapol | low | 3 mm | ~6700 | ~8500 | ~16000 | |
| Freebase | Pluronic F-127 | high | 0.8 mm | ~120 | ~130 | ~180 | 3 days, RT |
| HCl salt | Pluronic F-127 | high | 0.8 mm | ~100 | ~100 | ~140 | |
| HCl salt | Tyloxapol | high | 0.8 mm | ~110 | ~120 | ~170 | 6 days, 40° C. |
| Freebase | PVP K-29/32 | high | 0.8 mm | ~150 | ~210 | ~290 | 1 day, RT |
| Freebase | PVP K-29/32 | high | 0.8 mm | ~130 | ~170 | ~230 | 15 days, RT |
| HCl salt | HPMC | low | 3 mm | ~170 | ~450 | ~1200 | 21 days, RT |
| Freebase | Tween 80 | high | 0.8 mm | ~160 | ~370 | ~1000 | 28 days, RT |
| Freebase | Pluronic F-127 | | | ~3400 | ~3700 | ~6600 | |

Example 22

Preparation of Compound-I/Tris Formulation

A non-milled suspension of the Compound-I was prepared. The formulation consisted of: 3% Compound-I; 0.6% Tris-HCl pH 6; 2% Glycerol. Compound-I was added to the solution directly and mixed without milling and characterized (FIG. 9C).

Example 23

Particles Comprising Formula II and Vitamin K3

Addition of Vitamin $K_3$ (menadione) to the suspension formulation may have a beneficial in-vivo effect. Menadione was added to the formulation as a milled suspension. Menadione was initially milled exactly as the Formula II was milled; a 5% suspension with Pluronic F-127 as the stabilizer. This suspension was then added to Formula II before milling (large and nanoparticle formulations). The milled 5% suspensions (containing menadione suspension) were then diluted to 0.4% of Formula II (in glycerol, as previously described).

Menadione did not appear to affect any physical characteristics of the milled particles of Formula II (FIG. 9D). However, at the highest concentration of menadione added (10 μM), it was detected particles of vitamin $K_3$ that were increasing in size. Additionally, there was a small population of very large particles outside the range of the free base, which was presumably the vitamin $K_3$. It was concluded that the vitamin $K_3$ could not be homogeneously distributed as well as the other particles in the suspension, as they were growing at a faster rate than the Formula II.

Example 24

Preparation of Particles Comprising Menadione

Formulation of menadione/Formula II may form larger crystals over time. An optimized formulation was required to be able to add the menadione as a suspension. Formulations containing 5% menadione were screened using a roller mill in the same way as when screening the Formula II formulations. An HPMC formulation produced a fine, homogeneous suspension that demonstrated short term stability at 40° C. (FIG. 10).

Example 25

Preparation of Particles Comprising Formula II

The HPMC formulation for menadione was used with Formula II to provide a formulation in which the menadione could be added as a suspension. It was found that an X-large (30-40 micron) particle size using HPMC could be milled in a shorter time than when using Pluronic F-127 as the stabilizer (FIGS. 11A and 11B). The suspension could then be diluted with a menadione/HPMC suspension.

Example 25

Stability of Menadione in Formulations of the Present Application

The menadione concentration was 20 μM in the stability study. The menadione was formulated as follows: 0.43% w/v Compound-I (unmilled, 50 μm), 0.6% Tris/HCl, pH 6, 2% Glycerol, 0.2% HEC, 0.08% HPMC and 20 μM menadione. From this formulation, ten test formulations were prepared:
1. minus glycerin (no $N_2$)
2. control formulation; (no $N_2$)
3. control formulation; $N_2$ sparged
4. +0.3% Na thiosulfate (pentahydrate), $N_2$ sparged*
5. +0.1% Na2 EDTA, $N_2$ sparged
6. +0.5% TPGS Vitamin E, $N_2$ sparged
7. +0.05% propyl gallate, $N_2$ sparged
8. +0.02% BHT, $N_2$ sparged
9. +menadione/HPb-cyclodextrin complex, $N_2$ sparged
10. +anti-oxidant complex (#5-#9), $N_2$ sparged 7 mL of each formulation was added to an amber 40 ml vial (under amber lighting). Filtered nitrogen gas was slowly bubbled into the bottom of the vial until the generated foam began to exit the top of the vial, which was then quickly capped. Menadione/HPb-Cyclodextrin complex (#9) was prepared by mixing approximately equimolar concentrated solutions of cyclodextrin and menadione before addition (approximately 2 hours) to the formulation.

Example 26

Methods for Roller Milling and Characterization of the Particles of the Present Application Roller Mill The horizontal roller mill (US Stoneware, model 755) consists of four, motor driven 12" rubber rollers contained within a metal housing. Individual bottles placed between the rollers will rotate at an rpm determined by the speed of the rollers and the diameter of the bottle. Drug slurry consisting of API, stabilizers, water and milling media was added to the bottle and the cap tightly sealed before placing between the rollers. The media used was an extremely dense Yttria Zirconium bead that varies in diameter from 800 microns to 3000 microns. After milling, the dispersion was separated from the media by transferring the contents to a centrifuge tube insert fitted with a screen mesh. The small insert was placed into a centrifuge tube. The centrifuge was then run at approximately 300×G for approximately 5 minutes. The dispersion collected below the mesh (which retained the media) into the tube.

Optical Microscopy (OM)

Optical microscopy photomicrographs of nanoparticles were taken using an Olympus BX51 system equipped with an oil immersion 100× objective (1000× magnification). A calibration bar (from 1 um to 100 um) was set as a comparator on each photomicrograph. (The calibration bar effectively serves to size larger particles at lower magnifications, as well.)

Particle Size Distribution (PSD)

Particle size distribution was analyzed using laser diffraction light scattering with a Horiba LA-950 V2. Generic assumptions were made in setting conditions and the refractive index value. The distributions were volume based. Sample density was adjusted to a generic range of percent transmission on the blue LED light source. A small sample cell (filled with water) was used rather than the flow through cell, to minimize sample quantity.

INCORPORATION BY REFERENCE

The entire disclosure of each of the patent documents and scientific articles referred to herein is incorporated by reference for all purposes. In the present application the host document is identified with sufficient particularity and materials that are relevant to the disclosure are construed based on the context of the reference. Citation of publications and patent documents is not intended as an admission that any is pertinent prior art, nor does it constitute any admission as to the contents or date of the same. The application having now been described by way of written description, those of skill in the art will recognize that the application can be practiced in a variety of embodiments and the foregoing description and examples are for purposes of illustration and not limitation of the claims that follow.

EQUIVALENTS

The application can be embodies in other specific forms without departing from the spirit or essential characteristics thereof. The foregoing embodiments are therefore to be considered in all respects illustrative rather than limiting on the application described herein. Scope of the application is thus indicated by the appended claims rather than by the foregoing description, and all changes that come within the meaning and range of equivalency of the claims are intended to be embraced therein.

The invention claimed is:

1. A topical, ocular, suspension formulation, comprising:
   a. a first active agent of Formula II:

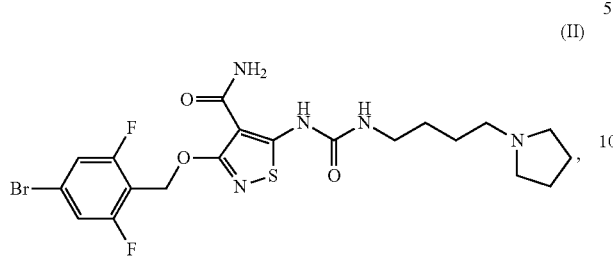

(II)

or a pharmaceutically acceptable salt thereof;
   b. a second active agent, or a pharmaceutically acceptable salt thereof, wherein the second active agent is nicotinic acid, nicotinamide, or vitamin K, or a combination thereof; and
   c. a pharmaceutically acceptable excipient;
wherein the first active agent or the pharmaceutically acceptable salt thereof is present in about 0.1% to about 2.0% w/v.

2. The formulation of claim 1, comprising Compound-I:

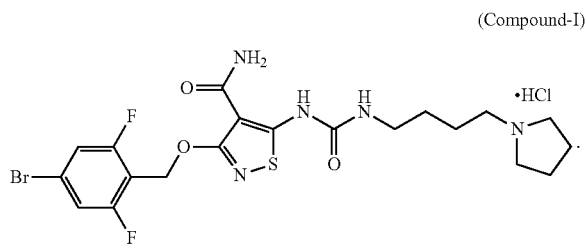 [SMILES: NC(=O)c1c(OCc2c(F)cc(Br)cc2F)nsc1NC(=O)NCCCCN1CCCC1 ; Cl]

(Compound-I)

3. The formulation of claim 1, comprising about 0.1%, about 0.2%, about 0.3%, or about 0.4% w/v of the compound of Formula II or a pharmaceutically acceptable salt thereof.

4. The formulation of claim 1, wherein the second active agent is vitamin K.

5. The formulation of claim 1, comprising particles of the first active agent, or a pharmaceutically acceptable salt thereof, wherein the particles have a mean diameter of between 100 nm and 100 μm.

6. The formulation of claim 5, wherein the particles have a mean diameter of between 30 μm and 60 μm.

7. The formulation of claim 5, wherein the particles have a mean diameter of between 1 μm and 5 μm.

8. The formulation of claim 5, wherein the particles have a mean diameter of at most 150 nm.

9. The formulation of claim 5, wherein the particles have a mean diameter of about 3 μm, about 30 μm, about 35 μm, or about 50 μm.

10. The formulation of claim 1, wherein the second active agent is present in an amount of less than 10 μM.

11. The formulation of claim 10, wherein the second active agent is present in an amount of about 1 μM.

12. The formulation of claim 1, further comprising one or more excipients selected from Polysorbate (Tween) 80, Poloxamer (Pluronic) F-127, Hypromellose (Hydroxypropyl Methylcellulose or HPMC), Povidone (PVP K-29/32 or K-30), and Tyloxapol, and a combination thereof.

13. The formulation of claim 1, comprising about 0.1% to about 1.0% (w/v) of the compound of Formula II or a pharmaceutically acceptable salt thereof.

14. The formulation of claim 1, comprising about 0.2% to about 1.0% (w/v) of the compound of Formula II or a pharmaceutically acceptable salt thereof.

15. The formulation of claim 1, comprising about 0.2%, about 0.3%, about 0.4%, about 0.5%, about 0.6%, about 0.7%, about 0.8%, about 0.9%, or about 1.0% (w/v) of the compound of Formula II or a pharmaceutically acceptable salt thereof.

16. The formulation of claim 1, wherein the second active agent is present in an amount of about 1 μM, about 2 μM, about 3 μM, about 4 μM, or about 5 μM.

17. The formulation of claim 1, further comprising a stabilizer for the second active agent.

18. The formulation of claim 1, wherein the formulation has a pH of about 6.

* * * * *